US012648967B2

(12) United States Patent
Almeida-Porada et al.

(10) Patent No.: US 12,648,967 B2
(45) Date of Patent: Jun. 9, 2026

(54) POST-NATAL TRANSPLANTATION OF FACTOR VIII-EXPRESSING CELLS FOR TREATMENT OF HEMOPHILIA

(71) Applicants: Wake Forest University Health Sciences, Winston-Salem, NC (US); Emory University, Atlanta, GA (US); Children's Healthcare of Atlanta, Inc., Atlanta, GA (US)

(72) Inventors: Maria Graca N.D. Almeida-Porada, Winston-Salem, NC (US); Christopher D. Porada, Winston-Salem, NC (US); Anthony Atala, Winston-Salem, NC (US); Christopher B. Doering, Atlanta, GA (US); H. Trent Spencer, Marietta, GA (US)

(73) Assignees: Wake Forest University Health Sciences, Winston-Salem, NC (US); Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 18/129,398

(22) Filed: Mar. 31, 2023

(65) Prior Publication Data

US 2024/0139253 A1 May 2, 2024

Related U.S. Application Data

(63) Continuation of application No. 16/638,379, filed as application No. PCT/US2018/047747 on Aug. 23, 2018, now abandoned.

(60) Provisional application No. 62/549,280, filed on Aug. 23, 2017.

(51) Int. Cl.
| | |
|---|---|
| *A61K 35/28* | (2015.01) |
| *A61K 38/37* | (2006.01) |
| *C12N 5/0775* | (2010.01) |

(52) U.S. Cl.
CPC .............. *A61K 35/28* (2013.01); *A61K 38/37* (2013.01); *C12N 5/0663* (2013.01); *C12N 5/0668* (2013.01); *C12N 2510/00* (2013.01)

(58) Field of Classification Search
CPC ...... A61K 35/28; A61K 38/37; C12N 5/0668; C12N 5/06; C07K 14/755
See application file for complete search history.

(56) References Cited

U.S. PATENT DOCUMENTS

| | | | |
|---|---|---|---|
| 7,635,763 | B2 | 12/2009 | Lollar |
| 7,968,336 | B2 | 6/2011 | Atala et al. |
| 8,021,876 | B2 | 9/2011 | Atala et al. |
| 2010/0183556 | A1 | 7/2010 | Choi et al. |
| 2010/0233119 | A1 | 9/2010 | Josephson |
| 2010/0311659 | A1 | 12/2010 | Saboulard et al. |

FOREIGN PATENT DOCUMENTS

| | | |
|---|---|---|
| WO | 9853063 A3 | 3/1999 |
| WO | 0029002 A2 | 5/2000 |
| WO | 2011102890 A1 | 8/2011 |
| WO | 2016168128 A2 | 10/2016 |
| WO | 2016183593 A2 | 11/2016 |

OTHER PUBLICATIONS

Rosner et al. Multipotent fetal stem cells in reproductive biology research. Stem Cell Research & Therapy (2023) 14:157, p. 1-26 (Year: 2023).*
Dominici et al. Minimal criteria for defining multipotent mesenchymal stromal cells. The International Society for Cellular Therapy position statement. Cytotherapy (2006) vol. 8, No. 4, 315-317 (Year: 2006).*
Castrechini et al. Mesenchymal stem cells in human placental chorionic villi reside in a vascular Niche. Placenta 31 (2010) 203-212 (Year: 2010).*
Matsui et al. Immune-Modulatory Effects of Mesenchymal Stromal Cell Infusions for the Treatment of Factor VIII Inhibitor in Hemophilia A. Blood (2009) 114 (22) : 1299 (Year: 1299).*
Ramachandra et al. In utero therapy for congenital disorders using amniotic fluid stem cells. Front. Pharmacol. 5:270, p. 1-12 (Year: 2014).*
Waddington et al. Fetal and neonatal gene therapy: benefits and pitfalls. Gene Therapy vol. 11, pp. S92-S97 (Year: 2004).*
Sick et al. CD47 update: a multifaceted actor in the tumour microenvironment of potential therapeutic interest. British Journal of Pharmacology (2012) 167 1415-1430 (Year: 2012).*
Application No. PCT/US2018/047747, International Search Report and Written Opinion, mailed Oct. 30, 2018, 13 pages.
Application No. PCT/US2018/047751, International Search Report and Written Opinion, mailed Dec. 21, 2018, 13 pages.
Abo, "Extrathymic Pathways of T-Cell Differentiation: A Primitive and Fundamental Immune System", Microbiology and Immunology, vol. 37, No. 4, Apr. 1993, pp. 247-258.
Abrahamsen et al., "Targeting B Cell Leukemia with Highly Specific Allogeneic T Cells with a Public Recognition Motif", Leukemia, vol. 24, No. 11, Nov. 2010, pp. 1901-1909.
Aggarwal et al., "Human Mesenchymal Stem Cells Modulate Allogeneic Immune Cell Responses", Blood, vol. 105, No. 4, Feb. 15, 2005, pp. 1815-1822.
Aiuti et al., "Correction of ADA-SCID by Stem Cell Gene Therapy Combined with Nonmyeloablative Conditioning", Science, vol. 296, No. 5577, Jun. 28, 2002, pp. 2410-2413.

(Continued)

*Primary Examiner* — Taeyoon Kim
(74) *Attorney, Agent, or Firm* — Kilpatrick Townsend & Stockton LLP

(57) ABSTRACT

Disclosed herein are method of treating hemophilia A in a subject comprising injecting the subject with mesenchymal stromal/stem cells (MSC) modified to express high levels of Factor VIII protein. The MSC are isolated prenatally, at birth, or after the subject's birth. The modified MSC may also express high levels von Willebrand factor protein.

19 Claims, 9 Drawing Sheets

Specification includes a Sequence Listing.

(56)            References Cited

OTHER PUBLICATIONS

Aiuti et al., "Ten Years of Gene Therapy for Primary Immune Deficiencies", American Society of Hematology, Newer Progress in Gene Therapy, vol. 2009, No. 1, Jan. 1, 2009, pp. 682-689.

Algiman et al., "Natural Antibodies to Factor VIII (Anti-Hemophilic Factor) in Healthy Individuals", Proceedings of the National Academy of Sciences of the United States of America, vol. 89, No. 9, May 1, 1992, pp. 3795-3799.

Alhajjat et al., "NK Cell Tolerance as the Final Endorsement of Prenatal Tolerance After in Utero Hematopoietic Cellular Transplantation", Frontiers in Pharmacology, vol. 6, Article 51, Mar. 18, 2015, 7 pages.

Alhajjat et al., "Prenatal Allospecific NK Cell Tolerance Hinges on Instructive Allorecognition Through the Activating Receptor During Development", Journal of Immunology, vol. 195, No. 4, Aug. 15, 2015, pp. 1506-1516.

Alhajjat et al., "Regulation of the Earliest Immune Response to in Utero Hematopoietic Cellular Transplantation", Chimerism, vol. 1, No. 2, Oct.-Dec. 2010, pp. 1-3.

Allacher et al., "Stimulation and Inhibition of FVIII-Specific Memory B-Cell Responses by CpG-B (ODN 1826), a Ligand for Toll-Like Receptor 9", Thrombosis and Hemostasis, Blood, vol. 117, No. 1, Jan. 6, 2011, pp. 259-267.

Almeda-Porada et al., "Transplantation of Fetal Recipients with Placental Cells Engineered to Express FVIII Leads to Corrective Plasma Levels after Birth", American Society of Gene and Cell Therapy 21st Annual Meeting, Apr. 30, 2018, 3 pages.

Almeida-Porada et al., "A Large Animal Noninjury Model for Study of Human Stem Cell Plasticity", Blood Cells, Molecules and Diseases, vol. 32, No. 1, Jan.-Feb. 2004, pp. 77-81.

Almeida-Porada et al., "Bone Marrow Stem Cells and Liver Regeneration", Experimental Hematology, vol. 38, No. 7, Jul. 2010, pp. 574-580.

Almeida-Porada et al., "Cotransplantation of Stroma Results in Enhancement of Engraftment and Early Expression of Donor Hematopoietic Stem Cells in Utero", Experimental Hematology, vol. 27, No. 10, Oct. 1999, pp. 1569-1575.

Almeida-Porada et al., "Differentiative Potential of Human Metanephric Mesenchymal Cells", Experimental Hematology, vol. 30, No. 12, Dec. 2002, pp. 1454-1462.

Almeida-Porada et al., "Formation of Human Hepatocytes by Human Hematopoietic Stem Cells in Sheep", Blood, vol. 104, No. 8, Oct. 15, 2004, pp. 2582-2590.

Almeida-Porada et al., "In Utero Stem Cell Transplantation and Gene Therapy: Rationale, History, and Recent Advances Toward Clinical Application", Molecular Therapy—Methods & Clinical Development, vol. 5, No. 16020, Jan. 1, 2016, pp. 1-17.

Almeida-Porada et al., "In Vivo Haematopoietic Potential of Human Neural Stem Cells", British Journal of Haematology, vol. 130, No. 2, Jul. 2005, pp. 276-283.

Almeida-Porada et al., "Plasticity of Human Stem Cells in the Fetal Sheep Model of Human Stem Cell Transplantation", International Journal of Hematology, vol. 79, No. 1, Jan. 2004, pp. 1-6.

Almeida-Porada et al., "Prenatal Transplantation of Placental Cells Engineered to Express FVIII Leads to Corrective Plasma Levels of FVIII after Birth", Blood, vol. 130, No. 1, Dec. 7, 2017, 4 pages.

Almeida-Porada et al., "The Role of Sheep Stroma in Human Haemopoiesis in the Human/Sheep Chimaeras", British Journal of Haematology, vol. 93, No. 4, Jun. 1996, pp. 795-802.

Altanerova et al., "Genotoxic Damage of Human Adipose-Tissue Derived Mesenchymal Stem Cells Triggers Their Terminal Differentiation", Neoplasma, vol. 56, No. 6, Feb. 2009, pp. 542-547.

Ananyeva et al., "Inhibitors in Hemophilia A: Mechanisms of Inhibition, Management and Perspectives", Blood Coagulation & Fibrinolysis, vol. 15, No. 2, Mar. 2004, pp. 109-124.

Anumanthan et al., "Directed Differentiation of Bone Marrow Derived Mesenchymal Stem Cells Into Bladder Urothelium", The Journal of Urology, vol. 180, No. 4, Aug. 2008, pp. 1778-1783.

Arnold, "Parenchymal Cells in Immune and Tolerance Induction", Immunology Letters, vol. 89, No. 2-3, Oct. 31, 2003, pp. 225-228.

Astermark et al., "Current European Practice in Immune Tolerance Induction Therapy in Patients with Haemophilia and Inhibitors", Haemophilia, vol. 12, No. 4, Jul. 2006, pp. 363-371.

Astermark et al., "Non-Genetic Risk Factors and the Development of Inhibitors in Haemophilia: A Comprehensive Review and Consensus Report", Haemophilia, vol. 16, No. 5, Sep. 1, 2010, pp. 747-766.

Athale et al., "Immune Tolerance Induction for Treating Inhibitors in People with Congenital Haemophilia A or B", Cochrane Database of Systematic Reviews, vol. 24, No. 4, Apr. 24, 2014, 44 pages.

Backfisch et al., "Carrier Detection of Ovine Hemophilia a Using an RFLP Marker, and Mapping of the Factor VIII Gene on the Ovine X-Chromosome", Journal of Heredity, vol. 85, No. 6, Nov.-Dec. 1994, pp. 474-478.

Baharvand et al., "Concise Review: Trends in Stem Cell Proteomics", Stem Cells, vol. 25, No. 8, Aug. 2007, pp. 1888-1903.

Balak et al., "Prenatal Diagnosis for Haemophilia: A Nationwide Survey Among Female Carriers in the Netherlands", Haemophilia, vol. 18, No. 4, Jul. 2012, pp. 584-592.

Batten et al., "Human Mesenchymal Stem Cells Induce T Cell Anergy and Downregulate T Cell Allo-responses via the Th2 Pathway: Relevance to Tissue Engineering Human Heart Valves", Tissue Engineering, vol. 12, No. 8, Aug. 2006, pp. 2263-2273.

Bauer et al., "In Vivo Biosafety Model to Assess the Risk of Adverse Events From Retroviral and Lentiviral Vectors", Molecular Therapy, vol. 16, No. 7, Aug. 2008, pp. 1308-1315.

Beagles et al., "Cyclosporine Inhibits the Development of Green Fluorescent Protein (GFP)-Specific Immune Responses after Transplantation of GFP-Expressing Hematopoietic Repopulating Cells in Dogs", Human Gene Therapy, vol. 16, No. 6, Jun. 2005, pp. 725-733.

Becker et al., "Confocal Microscopy Analysis of Native, Full Length and B-Domain Deleted Coagulation Factor Viii Trafficking in Mammalian Cells", Journal of Thrombosis and Haemostasis, vol. 92, No. 1, Jul. 2004, pp. 23-35.

Behrmann et al., "Von Willebrand Factor Modulates Factor VIII Immunogenicity: Comparative Study of Different Factor VIII Concentrates in a Haemophilia A Mouse Model", Thrombosis and Haemostasis, vol. 88, No. 2, Aug. 2002, pp. 221-229.

Bernardo et al., "Human Bone Marrow Derived Mesenchymal Stem Cells do not Undergo Transformation After Long-Term in Vitro Culture and do not Exhibit Telomere Maintenance Mechanisms", Cancer Research, vol. 67, No. 19, Oct. 1, 2007, pp. 9142-9149.

Berrios et al., "The Molecular Basis for the Cytokine-Induced Defect in Homing and Engraftment of Hematopoietic Stem Cells", Experimental Hematology, vol. 29, No. 11, Nov. 2001, pp. 1326-1335.

Boura et al., "Evaluation of Gene Delivery Strategies to Efficiently Overexpress Functional HLA-G on Human Bone Marrow Stromal Cells", Molecular Therapy: Methods & Clinical Development, vol. 2014, No. 1, Sep. 2014, 10 pages.

Boursier et al., "Characterization of Cells of the B Lineage in the Human Adult Greater Omentum", Immunology, vol. 119, No. 1, Sep. 1, 2006, pp. 90-97.

Bowen et al., "Intrahepatic Immunity: A Tale of Two Sites?", Trends in Immunology, vol. 26, No. 10, Oct. 2005, pp. 512-517.

Brown et al., "A microRNA-regulated Lentiviral Vector Mediates Stable Correction of Hemophilia B Mice", Blood, vol. 110, No. 13, Dec. 15, 2007, pp. 4144-4152.

Brown et al., "Bioengineered Coagulation Factor VIII Enables Long-Term Correction of Murine Hemophilia a Following Liver-Directed Adeno-Associated Viral Vector Delivery", Molecular Therapy—Methods and Clinical Development, vol. 1, No. 14036, Aug. 6, 2014, pp. 1-10.

Brown et al., "Endogenous microRNA Regulation Suppresses Transgene Expression in Hematopoietic Lineages and Enables Stable Gene Transfer", Nature Medicine, vol. 12, No. 5, May 2006, pp. 585-591.

Brown et al., "Enhanced Biosynthesis of Coagulation Factor VIII Through Diminished Engagement of the Unfolded Protein Response", Journal of Biological Chemistry, vol. 286, No. 27, Jul. 8, 2011, pp. 24451-24457.

(56)　　　　　References Cited

OTHER PUBLICATIONS

Brown et al., "Target-Cell-Directed Bioengineering Approaches for Gene Therapy of Hemophilia A", Molecular Therapy Methods & Clinical Development, vol. 9, Jun. 2018, pp. 57-69.

Cao et al., "Induction and Role of Regulatory CD4+CD25+ T Cells in Tolerance to the Transgene Product Following Hepatic in Vivo Gene Transfer", Blood, vol. 110, No. 4, Aug. 15, 2007, pp. 1132-1140.

Caplan et al., "Mesenchymal Stem Cells as Trophic Mediators", Journal of Cellular Biochemistry, vol. 98, No. 5, Aug. 1, 2006, pp. 1076-1084.

Cavazzana-Calvo et al., "Gene Therapy of Human Severe Combined Immunodeficiency (SCID)-X1 Disease", Science, vol. 288, No. 5466, Apr. 28, 2000, pp. 669-672.

Cavazzana-Calvo et al., "Gene Therapy of Severe Combined Immunodeficiencies", Journal of Gene Medicine, vol. 3, No. 3, May-Jun. 2001, pp. 201-206.

Cerbini et al., "Transfection, Selection, and Colony-Picking of Human Induced Pluripotent Stem Cells TALEN-Targeted with a GFP Gene into the AAVS1 Safe Harbor", Journal of Visualized Experiments, vol. 96, No. 52504, Feb. 1, 2015, 9 pages.

Cesana et al., "Whole Transcriptome Characterization of Aberrant Splicing Events Induced by Lentiviral Vector Integrations", The Journal of Clinical Investigation, vol. 122, No. 5, May 2012, pp. 1667-1676.

Chalmers et al., "Guideline on the Management of Haemophilia in the Fetus and Neonate", British Journal of Haematology, vol. 154, No. 2, Jul. 2011, pp. 208-215.

Chamberlain et al., "Efficient Generation of Human Hepatocytes by the Intrahepatic Delivery of Clonal Human Mesenchymal Stem Cells in Fetal Sheep", Hepatology, vol. 46, No. 6, Dec. 2007, pp. 1935-1945.

Chan et al., "Prenatal Transplantation of Mesenchymal Stem Cells to Treat Osteogenesis Imperfecta", Frontiers Pharmacology, vol. 5, Oct. 2014, pp. 1-6.

Chapel et al., "Mesenchymal Stem Cells Home to Injured Tissues When Co-Infused with Hematopoietic Cells to Treat a Radiation-Induced Multi-Organ Failure Syndrome", Journal of Gene Medicine, vol. 5, No. 12, Dec. 2003, pp. 1028-1038.

Charan et al., "How to Calculate Sample Size in Animal Studies?", Journal of Pharmacology and Pharmacotherapeutics, vol. 4, No. 4, Oct.-Dec. 2013, pp. 303-306.

Chuah et al., "Bone Marrow Stromal Cells as Targets for Gene Therapy of Hemophilia A", Human Gene Therapy, vol. 9, No. 3, Feb. 10, 1998, pp. 353-365.

Chuah et al., "Long-Term Persistence of Human Bone Marrow Stromal Cells Transduced with Factor VIII-Retroviral Vectors and Transient Production of Therapeutic Levels of Human Factor VIII in Nonmyeloablated Immunodeficient Mice", Human Gene Therapy, vol. 11, No. 5, Mar. 20, 2000, pp. 729-738.

Cogan, "The Experimental Design/Statistics", Available online at https://eda.nc3rs.org.uk/, Accessed from Internet on Oct. 4, 2021, pp. 1-2.

Colletti et al., "Early Fetal Gene Delivery Utilizes Both Central and Peripheral Mechanisms of Tolerance Induction", Experimental Hematology, vol. 36, No. 7, Jul. 2008, pp. 816-822.

Colletti et al., "EphB2 Isolates a Human Marrow Stromal Cell Subpopulation with Enhanced Ability to Contribute to the Resident Intestinal Cellular Pool", The FASEB Journal, vol. 27, No. 6, Jun. 2013, pp. 2111-2121.

Colletti et al., "Generation of Tissue-Specific Cells from MSC Does not Require Fusion or Donor-to-Host Mitochondrial/Membrane Transfer", Stem Cell Research, vol. 2, No. 2, Mar. 2009, pp. 125-138.

Colletti et al., "Tales from the Crypt: Mesenchymal Stem Cells for Replenishing the Intestinal Stem Cell Pool", Blood, vol. 112, No. 11, Nov. 16, 2008, 2 pages.

Colletti et al., "The Time Course of Engraftment of Human Mesenchymal Stem Cells in Fetal Heart Demonstrates that Purkinje Fiber Aggregates Derive from a Single Cell and not Multi-Cell Homing", Experimental Hematology, vol. 34, No. 7, Jul. 2006, pp. 926-933.

Craig et al., "Cytokine Expression in Naive and Previously Infected Lambs After Challenge with Teladorsagia Circumcincta", Veterinary Immunology and Immunopathology, vol. 120, Issue 1-2, Nov. 15, 2007, pp. 47-54.

Crop et al., "Donor-Derived Mesenchymal Stem Cells Suppress Alloreactivity of Kidney Transplant Patients", Transplantation, vol. 87, No. 6, Mar. 27, 2009, pp. 896-906.

Crop et al., "Potential of Mesenchymal Stem Cells as Immune Therapy in Solid-Organ Transplantation", Transplant International, vol. 22, No. 4, Apr. 2009, pp. 365-376.

Cunningham et al., "LMAN1 Is a Molecular Chaperone for the Secretion of Coagulation Factor VIII", Journal of Thrombosis and Haemostasis, vol. 1, No. 11, Nov. 2003, pp. 2360-2367.

Dai et al., "The Status of Carrier and Prenatal Diagnosis of Haemophilia in China", Haemophilia, vol. 18, No. 2, Mar. 2012, pp. 235-240.

Dasgupta et al., "VWF Protects FVIII From Endocytosis by Dendritic Cells and Subsequent Presentation to Immune Effectors", Blood, vol. 109, No. 2, Jan. 15, 2007, pp. 610-612.

Davey et al., "Genetic Therapy for the Fetus: A Once in a Lifetime Opportunity", Human Gene Therapy, vol. 22, No. 4, Apr. 2011, pp. 383-385.

De Geest et al., "Humoral Immune Response in Mice against a Circulating Antigen Induced by Adenoviral Transfer is Strictly Dependent on Expression in Antigen-Presenting Cells", Blood, vol. 101, No. 7, Apr. 1, 2003, pp. 2551-2556.

De Meyer et al., "Phenotypic Correction of Von Willebrand Disease Type 3 Blood-Derived Endothelial Cells with Lentiviral Vectors Expressing Von Willebrand Factor", Hemostasis, Thrombosis, and Vascular Biology, Blood, vol. 107, No. 12, Jun. 15, 2006, pp. 4728-4736.

Deka et al., "Indications of 1342 Fetal Cord Blood Sampling Procedures Performed as an Integral Part of High Risk Pregnancy Care", Journal of Obstetrics and Gynaecology, vol. 62, No. 1, Feb. 2012, pp. 20-24.

Delignat et al., "Comparison of the Immunogenicity of Different Therapeutic Preparations of Human Factor VIII in the Murine Model of Hemophilia A", Haematologica, vol. 92, No. 10, Oct. 2007, pp. 1423-1426.

Delignat et al., "Immunoprotective Effect of Von Willebrand Factor Towards Therapeutic Factor VIII in Experimental Haemophilia A", Haemophilia, vol. 18, No. 2, Mar. 2012, pp. 248-254.

Delo et al., "Amniotic Fluid and Placental Stem Cells", Methods in Enzymology, vol. 419, 2006, pp. 426-438.

Deng, "Mesenchymal Stem Cells Express c-kit", Circulation Research, vol. 107, No. 10, Nov. 12, 2010, 1 page.

Derderian et al., "In Utero Hematopoietic Cell Transplantation for Hemoglobinopathies", Frontiers in Pharmacology, vol. 5, Article 278, Jan. 2015, pp. 1-4.

Dimichele et al., "International Workshop on Immune Tolerance Induction: Consensus Recommendations", Haemophilia, vol. 13, Jul. 2007, pp. 1-22.

Dobrzynski et al., "Induction of Antigen-Specific CD4+ T-cell Anergy And Deletion by in Vivo Viral Gene Transfer", Blood, vol. 104, No. 4, Aug. 15, 2004, pp. 969-977.

Dobrzynski et al., "Prevention of Cytotoxic T Lymphocyte Responses to Factor IX-Expressing Hepatocytes by Gene Transfer-Induced Regulatory T Cells", Proceedings of the National Academy of Sciences of the United States of America, vol. 103, No. 12, Mar. 21, 2006, pp. 4592-4597.

Doering et al., "Directed Engineering of a High-Expression Chimeric Transgene as a Strategy for Gene Therapy of Hemophilia A", Molecular Therapy, vol. 17, No. 7, Jul. 2009, pp. 1145-1154.

Doering et al., "Expression and Characterization of Recombinant Murine Factor VIII", Thromb Haemost, vol. 88, No. 3, Sep. 2002, pp. 450-458.

Doering et al., "Identification of Porcine Coagulation Factor VIII Domains Responsible for High Level Expression via Enhanced Secretion", The Journal of Biological Chemistry, vol. 279, No. 8, Feb. 20, 2004, pp. 6546-6552.

(56)  References Cited

OTHER PUBLICATIONS

Doering , "Retroviral Modification of Mesenchymal Stem Cells for Gene Therapy of Hemophilia", Gene Therapy Protocols, Methods in Molecular Biology, vol. 433, 2008, pp. 203-212.

Dooriss et al., "Comparison of Factor VIII Transgenes Bioengineered for Improved Expression in Gene Therapy of Hemophilia A", Human Gene Therapy, vol. 20, No. 5, May 1, 2009, pp. 465-478.

Dorner et al., "The Relationship of N-Linked Glycosylation and Heavy Chain-Binding Protein Association with the Secretion of Glycoproteins", The Journal of Cell Biology, vol. 105, No. 6, Dec. 1987, pp. 2665-2674.

Durkin et al., "Early Chimerism Threshold Predicts Sustained Engraftment and NK-Cell Tolerance in Prenatal Allogeneic Chimeras", Blood, vol. 112, No. 13, Dec. 15, 2008, pp. 5245-5253.

Eckhardt et al., "Inhibitor Development and Mortality in Non-Severe Hemophilia A", Journal of Thrombosis and Haemostasis, vol. 13, No. 7, Jul. 2015, pp. 1217-1225.

Eixarch et al., "Transgene Expression Levels Determine the Immunogenicity of Transduced Hematopoietic Grafts in Partially Myeloablated Mice", Molecular Therapy, vol. 17, No. 11, Nov. 2009, pp. 1904-1909.

El-Akabawy et al., "Defining the Optimal FVIII Transgene for Placental Cell-Based Gene Therapy to Treat Hemophilia A", American Society of Gene and Cell Therapy 21st Annual Meeting, Available Online at https://plan.core-apps.com/asgct2018/abstract/82822071-9d48-4013-84d8-09eb8403dc11, May 2018, 1 page.

El-Asrar et al., "Assessment of the Frequency of Regulatory T Cells (CD4+CD25+CD127−) in Children with Hemophilia A: Relation to Factor VIII Inhibitors and Disease Severity", Blood Coagulation & Fibrinolysis, vol. 27, No. 1, Jan. 2016, pp. 42-46.

Ellabban et al., "The Pedicled 'Policeman' Flap Salvage of Exposed Vascular Prosthesis—A Case Report", Annals of The Royal College of Surgeons of England, vol. 89, No. 7, Oct. 2007, pp. 735-737.

Entrican et al., "Exploiting Ovine Immunology to Improve the Relevance of Biomedical Models", Molecular Immunology, vol. 66, No. 1, Jul. 2015, pp. 68-77.

Ettingshausen et al., "A Review of Immune Tolerance Induction with Haemate P in Haemophilia A", Haemophilia, vol. 20, No. 3, May 2014, pp. 333-339.

Ferber et al., "Levels of Peripheral T Cell Tolerance Induced by Different Doses of Tolerogen", Science, vol. 263, No. 5147, Feb. 4, 1994, pp. 674-676.

Festing, "Design and Statistical Methods in Studies Using Animal Models of Development", ILAR Journal, vol. 47, No. 1, Jan. 1, 2006, pp. 5-14.

Festing et al., "Guidelines for The Design and Statistical Analysis of Experiments Using Laboratory Animals", ILAR Journal, vol. 43, No. 4, Oct. 1, 2002, pp. 244-258.

Fischer et al., "Pulmonary Passage is a Major Obstacle for Intravenous Stem Cell Delivery: The Pulmonary First-Pass Effect", Stem Cells and Development, vol. 18, No. 5, Jun. 2009, pp. 683-692.

Flake et al., "In Utero Hematopoietic Stem Cell Transplantation: Ontogenic Opportunities and Biologic Barriers", Blood, vol. 94, No. 7, Oct. 1, 1999, pp. 2179-2191.

Flake, "In Utero Stem Cell Transplantation", Best Practice & Research: Clinical Obstetrics & Gynaecology, vol. 18, No. 6, Dec. 2004, pp. 941-958.

Flake et al., "Treatment of X-Linked Severe Combined Immunodeficiency by in Utero Transplantation of Paternal Bone Marrow", The New England Journal of Medicine, vol. 335, No. 24, Dec. 12, 1996, pp. 1806-1810.

Follenzi et al., "Efficient Gene Delivery and Targeted Expression to Hepatocytes in Vivo by Improved Lentiviral Vectors", Human Gene Therapy, vol. 13, No. 2, Jan. 20, 2002, pp. 243-260.

Follenzi et al., "Targeting Lentiviral Vector Expression to Hepatocytes Limits Transgene-Specific Immune Response and Establishes Long-Term Expression of Human Antihemophilic Factor IX In Mice", Blood, vol. 103, No. 10, May 15, 2004, pp. 3700-3709.

Fox et al., "Early Intraperitoneal Transfusion and Adjuvant Maternal Immunoglobulin Therapy in the Treatment of Severe Red Cell Alloimmunization Prior to Fetal Intravascular Transfusion", Fetal Diagnosis and Therapy, vol. 23, No. 2, Mar. 2008, pp. 159-163.

Fox et al., "Hepatocyte Transplantation", American Journal of Transplantation, vol. 4, No. 6, 2004, pp. 7-13.

Franco et al., "Evasion of Immune Responses to Introduced Human Acid Alpha-Glucosidase by Liver-Restricted Expression in Glycogen Storage Disease Type II", Molecular Therapy, vol. 12, No. 5, Nov. 2005, pp. 876-884.

Gallucci et al., "Danger Signals: SOS to the Immune System", Current Opinion in Immunology, vol. 13, No. 1, Feb. 1, 2001, pp. 114-119.

Gangadharan et al., "High-Level Expression of Porcine Factor VIII from Genetically Modified Bone Marrow-Derived Stem Cells", Blood, vol. 107, No. 10, May 15, 2006, pp. 3859-3864.

Garrett et al., "In Utero Recombinant Adeno-Associated Virus Gene Transfer in Mice, Rats, and Primates", BMC Biotechnology, vol. 3, Article 16, Sep. 30, 2003, pp. 1-8.

GenBank Accession No. 192448441, *Homo sapiens* Coagulation Factor VIII (F8), Transcript Variant 1, mRNA, GenBank, Available Online at: https://www.ncbi.nlm.nih.gov/nuccore/192448441, Jul. 17, 2017, 11 pages.

GenBank Accession No. 1023301060, *Homo sapiens* Von Willebrand Factor (VWF), mRNA, Available Online at: https://www.ncbi.nlm.nih.gov/nuccore/1023301060, Aug. 21, 2017, 11 pages.

Georgescu et al., "War and Peace: Factor VIII and the Adaptive Immune Response", Cellular Immunology, vol. 301, Mar. 2016, pp. 2-7.

Ghaderi et al., "Production Platforms for Biotherapeutic Glycoproteins. Occurrence, Impact, and Challenges of Non-Human Sialylation", Biotechnology & Genetic Engineering Reviews, vol. 28, Jan. 2012, pp. 147-175.

Ghosh et al., "Immune Response to FVIII in Hemophilia A: An Overview of Risk Factors", Clinical Reviews in Allergy & Immunology, vol. 37, No. 2, Oct. 2009, pp. 58-66.

Gotherstrom et al., "Pre- and Postnatal Transplantation of Fetal Mesenchymal Stem Cells in Osteogenesis Imperfecta: A Two-Center Experience", Stem Cells Translational Medicine, vol. 3, No. 2, Dec. 2013, pp. 255-264.

Green, "Factor VIII Inhibitors: A 50-Year Perspective", Haemophilia, vol. 17, No. 6, Nov. 2011, pp. 831-838.

Greene et al., "Ectopic Platelet-Delivered Factor (F) VIII for the Treatment of Hemophilia A: Plasma and Platelet FVIII, Is it all the Same?", Journal of Genetic Syndromes & Gene Therapy, vol. 1, Nov. 12, 2011, 10 pages.

Gregory et al., "Adult Bone Marrow Stem/Progenitor Cells (MSCs) are Preconditioned by Microenvironmental "Niches" in Culture: A Two-Stage Hypothesis for Regulation of MSC Fate", Science's STKE, vol. 2005, No. 294, Jul. 26, 2005, 5 pages.

Gringeri et al., "Understanding FVIII/VWF Complex—Report from a Symposium of XXIX WFH Meeting 2010", Haemophilia, vol. 18, No. 3, May 2012, pp. 469-475.

Hacein-Bey-Abina et al., "A Serious Adverse Event After Successful Gene Therapy for X-linked Severe Combined Immunodeficiency", The New England Journal of Medicine, vol. 348, No. 3, Jan. 16, 2003, pp. 255-256.

Hacein-Bey-Abina et al., "Insertional Oncogenesis in 4 Patients After Retrovirus-Mediated Gene Therapy of SCID-X1", Journal of Clinical Investigation, vol. 118, No. 9, Sep. 2008, pp. 3132-3142.

Hacein-Bey-Abina et al., "LMO2-Associated Clonal T Cell Proliferation in Two Patients after Gene Therapy for SCID-X1", Science, vol. 302, No. 5644, Oct. 17, 2003, pp. 415-419.

Hamada et al., "Mesenchymal Stem Cells (MSC) as Therapeutic Cytoreagents for Gene Therapy", Cancer Science, vol. 96, No. 3, Mar. 2005, pp. 149-156.

Hasbrouck et al., "AAV-Mediated Gene Transfer for the Treatment of Hemophilia B: Problems and Prospects", Gene Therapy, vol. 15, No. 11, Jul. 2008, pp. 870-875.

Hassan et al., "Blood Coagulation Factors in Human Embryonic-Fetal Development: Preferential Expression of the FVII/Tissue Factor Pathway", Blood, vol. 76, No. 6, Sep. 15, 1990, pp. 1158-1164.

Hausl et al., "High-Dose Factor VIII Inhibits Factor VIII-Specific Memory B Cells in Hemophilia A with Factor VIII Inhibitors",

(56) References Cited

OTHER PUBLICATIONS

Hemostasis, Thrombosis, and Vascular Biology, Blood, vol. 106, No. 10, Nov. 15, 2005, pp. 3415-3422.

Hausl et al., "Preventing Restimulation of Memory B Cells in Hemophilia A: A Potential New Strategy for the Treatment of Antibody-Dependent Immune Disorders", Hemostasis, Thrombosis, and Vascular Biology, Blood, vol. 104, No. 1, Jul. 1, 2004, pp. 115-122.

Hayashi et al., "Complete Allogeneic Hematopoietic Chimerism Achieved by a Combined Strategy of in Utero Hematopoietic Stem Cell Transplantation and Postnatal Donor Lymphocyte Infusion", Blood, vol. 100, No. 3, Aug. 1, 2002, pp. 804-812.

Hayashi et al., "Mixed Chimerism Following in Utero Hematopoietic Stem Cell Transplantation in Murine Models of Hemoglobinopathy", Experimental Hematology, vol. 31, No. 2, Feb. 2003, pp. 176-184.

Healey et al., "The Comparative Immunogenicity of Human and Porcine Factor Vill in Hemophilia a Mice", Thrombosis and Haemostasis, vol. 102, No. 1, Jul. 2009, pp. 35-41.

Heinz et al., "Factor VIII-eGFP Fusion Proteins with Preserved Functional Activity for the Analysis of the Early Secretory Pathway of Factor VIII", Thrombosis and Haemostasis, vol. 102, No. 5, Nov. 2009, pp. 925-935.

Herzog et al., "Immune Implications of Gene Therapy for Hemophilia", Seminars in Thrombosis and Hemostasis, vol. 30, No. 2, Apr. 2004, pp. 215-226.

High , "Gene Therapy for Haemophilia: A Long and Winding Road", Journal of Thrombosis and Haemostasis, vol. 9, Suppl 1, Jul. 2011, pp. 2-11.

High, "Gene Therapy for Hemophilia: The Clot Thickens", Human Gene Therapy, vol. 25, No. 11, Nov. 1, 2014, pp. 915-922.

High, "Gene Transfer as an Approach to Treating Hemophilia", Seminars in Thrombosis and Hemostasis, vol. 29, No. 1, Feb. 2003, pp. 107-120.

High, "Gene Transfer for Hemophilia: Can Therapeutic Efficacy in Large Animals Be Safely Translated to Patients?", Journal of Thrombosis and Haemostasis, vol. 3, No. 8, Aug. 2005, pp. 1682-1691.

High, "The Gene Therapy Journey for Hemophilia: Are We There Yet?", The American Society of Hematology Education Program, vol. 2012, 2012, pp. 375-381.

High , "Theodore E. Woodward Award: AAV-Mediated Gene Transfer for Hemophilia", Transactions of the American Clinical and Climatological Association, vol. 114, 2003, pp. 337-352.

Hironaka et al., "Comparative Study of the Sugar Chains of Factor VIII Purified From Human Plasma and From the Culture Media of Recombinant Baby Hamster Kidney Cells", Journal of Biological Chemistry, vol. 267, No. 12, Apr. 25, 1992, pp. 8012-8020.

Hixson et al., "An Overview on Prenatal Screening for Chromosomal Aberrations", Journal of Laboratory Automation, vol. 20, No. 5, Oct. 2015, pp. 562-573.

Hong et al., "Rhesus iPSC Safe Harbor Gene-Editing Platform for Stable Expression of Transgenes in Differentiated Cells of All Germ Layers", Molecular Therapy, vol. 25, No. 1, Jan. 4, 2017, pp. 44-53.

Honma et al., "Intravenous Infusion of Immortalized Human Mesenchymal Stem Cells Protects Against Injury in a Cerebral Ischemia Model in Adult Rat", Experimental Neurology, vol. 199, No. 1, May 2006, pp. 56-66.

Hope et al., "Development of Detection Methods for Ruminant Interleukin (IL)-4", Journal of Immunological Methods, vol. 301, Issue 1-2, Jun. 2005, pp. 114-123.

Howe et al., "Insertional Mutagenesis Combined with Acquired Somatic Mutations Causes Leukemogenesis Following Gene Therapy of SCID-X1 Patients", Journal of Clinical Investigation, vol. 118, No. 9, Sep. 2, 2008, pp. 3143-3150.

Huang et al., "Functional Network Reconstruction Reveals Somatic Stemness Genetic Maps and Dedifferentiation-Like Transcriptome Reprogramming Induced by GATA2", Stem Cells, vol. 26, No. 5, May 2008, pp. 1186-1201.

Hui et al., "Noninvasive Prenatal Testing Beyond Genomic Analysis: What The Future Holds", Current Opinion in Obstetrics and Gynecology, vol. 28, No. 2, Apr. 2016, pp. 105-110.

Hussein et al., "The Use of DNA Markers for Carrier Detection and Prenatal Diagnosis of Haemophilia A in Egyptian Families", Haemophilia, vol. 14, No. 5, Sep. 2008, pp. 1082-1087.

Ide et al., "Functional Aspects of Factor VIII Expression After Transplantation of Genetically-Modified Hematopoietic Stem Cells for Hemophilia A", Journal of Gene Medicine, vol. 12, No. 4, Apr. 2010, pp. 333-344.

Ide et al., "Hematopoietic Stem-Cell Gene Therapy of Hemophilia A Incorporating a Porcine Factor VIII Transgene and Nonmyeloablative Conditioning Regimens", Blood, vol. 110, No. 8, Oct. 15, 2007, pp. 2855-2863.

Jacquemin et al., "T Cell Response to FVIII", Cellular Immunology, vol. 301, Mar. 2016, pp. 8-11.

Jeanblanc et al., "Temporal Definition of Haematopoietic Stem Cell Niches in a Large Animal Model of In Utero Stem Cell Transplantation", British Journal of Haematology, vol. 166, No. 2, Jul. 2014, pp. 268-278.

Jeanty et al., "Maternal-Fetal Cellular Trafficking: Clinical Implications and Consequences", Current Opinion in Pediatrics, vol. 26, No. 3, Jun. 2014, pp. 377-382.

Jiang et al., "Human Mesenchymal Stem Cells Inhibit Differentiation and Function of Monocyte-Derived Dendritic Cells", Blood, vol. 105, No. 10, May 15, 2005, pp. 4120-4126.

Johnston et al., "Generation of an Optimized Lentiviral Vector Encoding a High-Expression Factor VIII Transgene for Gene Therapy of Hemophilia A", Gene therapy, vol. 20, No. 6, Jun. 2013, pp. 607-615.

Jones et al., "The Antiproliferative Effect of Mesenchymal Stem Cells is a Fundamental Property Shared by all Stromal Cells", Journal of Immunology, vol. 179, No. 5, Sep. 1, 2007, pp. 2824-2831.

Josephson et al., "Production of Foamy Virus Vector and Transduction of Hematopoietic Cells", Cold Spring Harbor Protocols, vol. 2010, No. 9, Sep. 1, 2010, 6 pages.

Kallas et al., "Von Willebrand Factor and Transforming Growth Factor-Beta Modulate Immune Response Against Coagulation Factor VIII in FVIII-Deficient Mice", Thrombosis Research, vol. 120, No. 6, 2007, pp. 911-919.

Kannicht et al., "Characterisation of the Post-Translational Modifications of a Novel, Human Cell Line-derived Recombinant Human Factor VIII", Thrombosis Research, vol. 131, No. 1, Jan. 2013, pp. 78-88.

Kassem, "Mesenchymal Stem Cells: Biological Characteristics and Potential Clinical Applications", Cloning Stem Cells, vol. 6, No. 4, Dec. 16, 2004, pp. 369-374.

Kasuda et al., "Therapeutic Approaches for Treating Hemophilia a Using Embryonic Stem Cells", Hematol Oneal Stem Cell Ther, vol. 9, Issue 2, Jun. 2016, pp. 64-70.

Kaufman et al., "Biosynthesis, Assembly and Secretion of Coagulation Factor VIII", Blood Coagulation & Fibrinolysis, vol. 8, Supplement 2, Dec. 1997, 12 pages.

Kaufman et al., "Effect of Von Willebrand Factor Coexpression on the Synthesis and Secretion of Factor VIII in Chinese Hamster Ovary Cells", Molecular and Cellular Biology, vol. 9, No. 3, Mar. 1989, pp. 1233-1242.

Kaufman et al., "Synthesis, Processing, and Secretion of Recombinant Human Factor VIII Expressed in Mammalian Cells", Journal of Biological Chemistry, vol. 263, No. 13, May 5, 1988, pp. 6352-6362.

Kaveri et al., "Factor VIII Inhibitors: Role of Von Willebrand Factor on the Uptake of Factor VIII by Dendritic Cells", Haemophilia, vol. 13, Dec. 2007, pp. 61-64.

Kempton et al., "Toward Optimal Therapy for Inhibitors in Hemophilia", Blood, vol. 124, No. 23, Nov. 27, 2014, pp. 3365-3372.

Kempton et al., "Toward Optimal Therapy for Inhibitors in Hemophilia", Hematology American Society of Hematology Education Program, vol. 2014, No. 1, Dec. 5, 2014, pp. 364-371.

Kerlin et al., "Modulation of IgG Subclass Expression During Antibody Responses in Sheep", Research in Veterinary Science, vol. 45, No. 3, Nov. 1988, pp. 353-359.

(56)        References Cited

OTHER PUBLICATIONS

Kim et al., "In Utero Bone Marrow Transplantation Induces Donor-Specific Tolerance by a Combination of Clonal Deletion and Clonal Anergy", Journal of Pediatric Surgery, vol. 34, No. 5, May 1999, pp. 726-729.

Kim et al., "Microchimerism and Tolerance After in Utero Bone Marrow Transplantation in Mice", Journal of Surgical Research, vol. 77, No. 1, Jun. 1998, pp. 1-5.

Knolle et al., "Local Control of The Immune Response in the Liver", Immunological Reviews, vol. 174, Apr. 2000, pp. 21-34.

Kohn, "Gene Therapy for Haematopoietic and Lymphoid Disorders", Clinical & Experimental Immunology, vol. 107, Jan. 1997, pp. 54-57.

Kumar et al., "In Utero Transplantation of Placenta-Derived Mesenchymal Stromal Cells for Potential Fetal Treatment of Hemophilia A", Cell Transplantation, vol. 27, No. 1, 2018, pp. 130-139.

Kumari et al., "Alloreactive Cytotoxic T Cells Provide Means to Decipher the Immunopeptidome and Reveal a Plethora of Tumor-Associated Self-Epitopes", Proceedings of the National Academy of Sciences, vol. 111, No. 1, Jan. 7, 2014, pp. 403-408.

Kung et al., "Induction of Transgene-Specific Immunological Tolerance in Myeloablated Nonhuman Primates using Lentivirally Transduced CD34+ Progenitor Cells", Molecular Therapy, vol. 8, No. 6, Dec. 2003, pp. 981-991.

Kuo et al., "Amniotic Fluid Stem Cells for the Treatment of Hemophilia A", Molecular Therapy, vol. 21, No. 1, May 1, 2013, pp. S96-S97.

Lacroix-Desmazes et al., "Dynamics of Factor VIII Interactions Determine its Immunologic Fate in Hemophilia A", Blood, vol. 112, No. 2, Jul. 15, 2008, pp. 240-249.

Lacroix-Desmazes et al., "The Role of VWF in the Immunogenicity of FVIII", Thrombosis Research, vol. 122, Jan. 1, 2008, pp. S3-S6.

Lai et al., "To Clear or to Fear: An Innate Perspective on Factor VIII Immunity", Cellular Immunology, vol. 301, Mar. 2016, pp. 82-89.

Lazarus et al., "Cotransplantation of HLA-Identical Sibling Culture-Expanded Mesenchymal Stem Cells and Hematopoietic Stem Cells in Hematologic Malignancy Patients", Biology of Blood and Marrow Transplantation, vol. 11, No. 5, May 2005, pp. 389-398.

Le Blanc et al., "Fetal Mesenchymal Stem-Cell Engraftment in Bone After in Utero Transplantation in a Patient with Severe Osteogenesis Imperfecta", Transplantation, vol. 79, No. 11, Jun. 15, 2005, pp. 1607-1614.

Le Blanc et al., "Immunobiology of Human Mesenchymal Stem Cells and Future Use in Hematopoietic Stem Cell Transplantation", Biology of Blood and Marrow Transplantation, vol. 11, No. 5, May 2005, pp. 321-334.

Lei et al., "Ligation of TLR2 and TLR4 on Murine Bone Marrow-Derived Mesenchymal Stem Cells Triggers Differential Effects on their Immunosuppressive Activity", Cellular Immunology, vol. 271, No. 1, Jun. 2011, pp. 147-156.

Liechty et al., "Human Mesenchymal Stem Cells Engraft and Demonstrate Site-Specific Differentiation After in Utero Transplantation in Sheep", Nature Medicine, vol. 6, No. 11, Nov. 2000, pp. 1282-1286.

Lillicrap et al., "Inhibitors—Genetic and Environmental Factors", Haemophilia, vol. 20, May 2014, pp. 87-93.

Lin et al., "Efficient Lentiviral Transduction of Human Mesenchymal Stem Cells That Preserves Proliferation and Differentiation Capabilities", Stem Cells Translational Medicine, vol. 1, No. 12, Dec. 2012, pp. 886-897.

Lind et al., "Novel Forms of B-Domain-Deleted Recombinant Factor VIII Molecules: Construction and Biochemical Characterization", European Journal of Biochemistry, vol. 232, No. 1, Aug. 15, 1995, pp. 19-27.

Lipshutz et al., "Reexpression Following Readministration of an Adenoviral Vector in Adult Mice After Initial in Utero Adenoviral Administration", Molecular Therapy, vol. 2, No. 4, Oct. 2000, pp. 374-380.

Lo et al., "Genomic Analysis of Fetal Nucleic Acids in Maternal Blood", Annual Review of Genomics and Human Genetics, vol. 13, No. 1, May 2012, pp. 285-306.

Loewendorf et al., "Immunological Considerations in in Utero Hematopoetic Stem Cell Transplantation (IUHCT)", Frontiers in Pharmacology, vol. 5, Jan. 6, 2015, pp. 1-16.

Lozier et al., "Animal Models of Hemophilia and Related Bleeding Disorders", Seminars in Hematology, vol. 50, No. 2, Apr. 2013, pp. 175-184.

Lubin et al., "Analysis of the Human Factor VIII A2 Inhibitor Epitope by Alanine Scanning Mutagenesis", The Journal of Biological Chemistry, vol. 272, No. 48, Nov. 28, 1997, pp. 30191-30195.

Maccario et al., "Interaction of Human Mesenchymal Stem Cells With Cells Involved in Alloantigen-Specific Immune Response Favors the Differentiation of CD4+ T-Cell Subsets Expressing a Regulatory/suppressive Phenotype", Haematologica, vol. 90, No. 4, Apr. 2005, pp. 516-525.

MacKenzie et al., "Consensus Statement From the First International Conference for in Utero Stem Cell Transplantation and Gene Therapy", Frontiers in Pharmacology, vol. 6, No. 15, Feb. 10, 2015, pp. 1-2.

Mackenzie et al., "Multilineage Differentiation of Human MSC after in Utero Transplantation", Cytotherapy, vol. 3, No. 5, Sep. 1, 2001, pp. 403-405.

Maddox et al., "Ontogeny of Ovine Lymphocytes. I. An Immunohistological Study on the Development of T Lymphocytes in the Sheep Embryo and Fetal Thymus", Immunology, vol. 62, No. 1, Sep. 1987, pp. 97-105.

Maddox et al., "Ontogeny of Ovine Lymphocytes. II. An Immunohistological Study on the Development of T Lymphocytes in the Sheep Fetal Spleen", Immunology, vol. 62, No. 1, Sep. 1987, pp. 107-112.

Maddox et al., "Ontogeny of Ovine Lymphocytes. III. An Immunohistological Study on the Development of T Lymphocytes in Sheep Fetal Lymph Nodes", Immunology, vol. 62, No. 1, Sep. 1987, pp. 113-118.

Maitra et al., "Human Mesenchymal Stem Cells Support Unrelated Donor Hematopoietic Stem Cells and Suppress T-Cell Activation", Bone Marrow Transplantation, vol. 33, No. 6, Mar. 2004, pp. 597-604.

Manco-Johnson , "Development of Hemostasis in the Fetus", Thrombosis Research, vol. 115, No. 1, Feb. 2005, pp. 55-63.

Manco-Johnson et al., "Prophylaxis Versus Episodic Treatment to Prevent Joint Disease in Boys with Severe Hemophilia", New England Journal of Medicine, vol. 357, No. 6, Aug. 9, 2007, pp. 535-544.

Mancuso et al., "Haemophilia Care in Children—Benefits of Early Prophylaxis for Inhibitor Prevention", Haemophilia, vol. 15, Jan. 2009, pp. 8-14.

Mannucci et al., "Novel Investigations on the Protective Role of the FVIII/VWF Complex in Inhibitor Development", Haemophilia, vol. 20, Sep. 2014, pp. 2-16.

Mannucci et al., "The Hemophilias—from Royal Genes to Gene Therapy", The New England Journal of Medicine, vol. 344, No. 23, Jun. 7, 2001, pp. 1773-1779.

Markusic et al., "High-Efficiency Transduction and Correction of Murine Hemophilia B Using AAV2 Vectors Devoid of Multiple Surface-Exposed Tyrosines", Molecular Therapy, vol. 18, No. 12, Dec. 2010, pp. 2048-2056.

Markusic et al., "Liver-Directed Adeno-Associated Viral Gene Therapy for Hemophilia", The Journal of Genetic Syndromes & Gene Therapy, Jan. 18, 2012, pp. 1-9.

Martins et al., "Quantification and Immunophenotypic Characterization of Bone Marrow and Umbilical Cord Blood Mesenchymal Stem Cells by Multicolor Flow Cytometry", Transplantation Proceedings, vol. 41, 2009, pp. 943-946.

Massaro et al., "Analysis of Five Polymorphic DNA Markers for Indirect Genetic Diagnosis of Haemophilia a in the Brazilian Population", Haemophilia, vol. 17, No. 5, Sep. 2011, pp. e936-e943.

Matino et al., "IDO1 Suppresses Inhibitor Development in Hemophilia a Treated with Factor VIII", Journal of Clinical Investigation, vol. 125, No. 10, Oct. 1, 2015, pp. 3766-3781.

(56) References Cited

OTHER PUBLICATIONS

Matzinger, "An Innate Sense of Danger", Annals of the New York Academy of Sciences, vol. 961, Jun. 2002, pp. 341-342.

Matzinger, "The Danger Model: A Renewed Sense of Self", Science, vol. 296, No. 5566, Apr. 12, 2002, pp. 301-305.

Matzinger, "Tolerance, Danger, and the Extended Family", Annual Review of Immunology, vol. 12, Feb. 1994, pp. 991-1045.

McClain et al., "In Utero Stem Cell Transplantation and Gene Therapy: Recent Progress and the Potential for Clinical Application", Best Practice & Research Clinical Obstetrics & Gynaecology, vol. 31, Feb. 2016, pp. 88-98.

McGinley et al., "Lentiviral Vector Mediated Modification of Mesenchymal Stem Cells & Enhanced Survival in an in Vitro Model of Ischaemia", Stem Cell Research & Therapy, vol. 2, No. 12, Mar. 7, 2011, pp. 1-18.

Meisel et al., "Human Bone Marrow Stromal Cells Inhibit Allogeneic T-Cell Responses by Indoleamine 2,3-dioxygenase-Mediated Tryptophan Degradation", Blood, vol. 103, No. 12, Jun. 15, 2004, pp. 4619-4621.

Merianos et al., "In Utero Hematopoietic Stem Cell Transplantation: Progress Toward Clinical Application", Biology of Blood and Marrow Transplantation, vol. 14, No. 7, Jul. 2008, pp. 729-740.

Merianos et al., "Maternal Alloantibodies Induce a Postnatal Immune Response That Limits Engraftment Following in Utero Hematopoietic Cell Transplantation in Mice", The Journal of clinical investigation, vol. 119, No. 9, Sep. 2009, pp. 2590-2600.

Mestas et al., "Of Mice and Not Men: Differences Between Mouse and Human Immunology", Journal of Immunology, vol. 172, No. 5, Mar. 1, 2004, pp. 2731-2738.

Miao et al., "Bioengineering of Coagulation Factor VIII for Improved Secretion", Blood, vol. 103, No. 9, May 1, 2004, pp. 3412-3219.

Miao et al., "CD4+FOXP3+ Regulatory T Cells Confer Long-Term Regulation of Factor VIII-Specific Immune Responses in Plasmid-Mediated Gene Therapy-Treated Hemophilia Mice", Blood, vol. 114, No. 19, Nov. 5, 2009, pp. 4034-4044.

Milosevic et al., "Renal Thromboembolism During Treatment with Recombinant Activated Factor VII (rFVIIa) in a Child with Hemophilia B With Factor IX Inhibitors", BMC Pediatrics, vol. 14, Dec. 17, 2014, pp. 1-4.

Mingozzi et al., "Induction of Immune Tolerance to Coagulation Factor IX Antigen by in Vivo Hepatic Gene Transfer", Journal of Clinical Investigation, vol. 111, No. 9, May 2003, pp. 1347-1356.

Modlich et al., "Insertional Transformation of Hematopoietic Cells by Self-Inactivating Lentiviral and Gammaretroviral Vectors", Molecular Therapy, vol. 17, No. 11, Nov. 2009, pp. 1919-1928.

Moghimi et al., "Induction of Tolerance to Factor VIII by Transient Co-administration with Rapamycin", Thrombosis and Haemostasis, vol. 9, No. 8, Aug. 2011, pp. 1524-1533.

Moiani et al., "Alternative Splicing Caused by Lentiviral Integration in the Human Genome", Methods in Enzymology, vol. 507, 2012, pp. 155-169.

Moiani et al., "Lentiviral Vector Integration in the Human Genome Induces Alternative Splicing and Generates Aberrant Transcripts", The Journal of Clinical Investigation, vol. 122, No. 5, May 2012, pp. 1653-1666.

Morsi et al., "Overexpression of FVIII Production in Placental Cells (PLCs) Increases Endogenous vWF", American Society of Gene and Cell Therapy 21st Annual Meeting, Apr. 30, 2018, 3 pages.

Mount et al., "Sustained Phenotypic Correction of Hemophilia B Dogs with A Factor IX Null Mutation by Liver-Directed Gene Therapy", Blood, vol. 99, No. 8, Apr. 15, 2002, pp. 2670-2676.

Muraca et al., "Liver and Liver Cell Transplantation for Glycogen Storage Disease Type IA", Acta Gastro-Enterologica Belgica, vol. 68, No. 4, Oct.-Dec. 2005, pp. 1-4.

Nasef et al., "Immunosuppressive Effects of Mesenchymal Stem Cells: Involvement of HLA-G", Transplantation, vol. 84, No. 2, Jul. 27, 2007, pp. 231-237.

Nauta et al., "Mesenchymal Stem Cells Inhibit Generation and Function of Both CD34+-Derived and Monocyte-Derived Dendritic Cells", Journal of Immunology, vol. 177, No. 4, Aug. 15, 2006, pp. 2080-2087.

Nazarov et al., "Multipotent Stromal Stem Cells from Human Placenta Demonstrate High Therapeutic Potential", Stem Cells Translational Medicine, vol. 1, No. 5, 2012, pp. 359-372.

Neuenschwander et al., "Factor VIII in Blood Plasma of Haemophilic Sheep: Analysis of Clotting Time-plasma Dilution Curves. Haemostasis", Haemostasis, vol. 24, No. 1, Jan.-Feb. 1994, pp. 27-35.

Neuenschwander et al., "Inherited Defect of Blood Clotting Factor VIII (Haemophilia A) in Sheep", Thrombosis and Haemostasis, vol. 68, No. 5, Nov. 10, 1992, pp. 618-620.

Nichols et al., "Translational Data from Adeno-Associated Virus-Mediated Gene Therapy of Hemophilia B in Dogs", Human Gene Therapy Clinical Development, vol. 26, No. 1, Mar. 2015, pp. 5-14.

Niemeyer et al., "Long-Term Correction of Inhibitor-Prone Hemophilia B Dogs Treated with Liver-Directed AAV2-Mediated Factor IX Gene Therapy", Blood, vol. 113, No. 4, Jan. 22, 2009, pp. 797-806.

Nijagal et al., "In Utero Hematopoietic Cell Transplantation for the Treatment of Congenital Anomalies", Clinics in Perinatology, vol. 39, No. 2, Jun. 2012, pp. 301-310.

Nijagal et al., "Maternal T Cells Limit Engraftment after in Utero Hematopoietic Cell Transplantation in Mice", Journal of Clinical Investigation, vol. 121, No. 2, Feb. 2011, pp. 582-592.

Nijagal et al., "The Maternal Immune Response Inhibits the Success of in Utero Hematopoietic Cell Transplantation", Chimerism, vol. 2, No. 2, Apr.-Jun. 2011, pp. 55-57.

Nivsarkar et al., "Evidence For Contribution of CD4+ CD25+ Regulatory T Cells in Maintaining Immune Tolerance to Human Factor IX Following Perinatal Adenovirus Vector Delivery", Journal of Immunology Research, vol. 2015, Jan. 31, 2015, pp. 1-6.

Oldenburg et al., "Alloantibodies to Therapeutic Factor VIII in Hemophilia A: The Role of Von Willebrand Factor in Regulating Factor VIII Immunogenicity", Haematologica, vol. 100, No. 2, Feb. 2015, pp. 149-156.

Oldenburg et al., "Primary and Rescue Immune Tolerance Induction in Children and Adults: A Multicentre International Study with a VWF-Containing Plasma-Derived FVIII Concentrate", Haemophilia, vol. 20, No. 1, Jan. 2014, pp. 83-91.

Ong et al., "Early Embryonic Expression of Murine Coagulation System Components", Journal of Thrombosis and Haemostasis, vol. 84, No. 6, Dec. 2000, pp. 1023-1030.

Osburn , "The Ontogeny of the Ruminant Immune System and its Significance in the Understanding of Maternal-Fetal-Neonatal Relationships", Advances in Experimental Medicine and Biology, vol. 137, 1981, pp. 91-103.

Pahl et al., "Effect of F8 B Domain Gene Variants on Synthesis, Secretion, Activity and Stability of Factor VIII Protein", Thrombosis and Haemostasis, vol. 111, No. 1, Jan. 2014, pp. 58-66.

Pearson et al., "Stem Cell and Genetic Therapies for the Fetus", Seminars in Pediatric Surgery, vol. 22, No. 1, Feb. 2013, pp. 56-61.

Peixeiro et al., "Control of Human B-Globin mRNA Stability and Its Impact on Beta-Thalassemia Phenotype", Haematologica, vol. 96, No. 6, Jun. 2011, pp. 905-913.

Peng et al., "Transient Blockade of the Inducible Costimulator Pathway Generates Long-Term Tolerance to Factor VIII After Non viral Gene Transfer into Hemophilia A Mice", Blood, vol. 112, No. 5, Sep. 1, 2008, pp. 1662-1672.

Peranteau et al., "Correction of Murine Hemoglobinopathies by Prenatal Tolerance Induction and Postnatal Nonmyeloablative Allogeneic BM Transplants", Blood, vol. 126, No. 10, Sep. 3, 2015, pp. 1245-1254.

Peranteau et al., "Evidence for an Immune Barrier After in Utero Hematopoietic-Cell Transplantation", Blood, vol. 109, No. 3, Feb. 1, 2007, pp. 1331-1333.

Peranteau et al., "High-Level Allogeneic Chimerism Achieved by Prenatal Tolerance Induction and Postnatal Nonmyeloablative Bone Marrow Transplantation", Blood, vol. 100, No. 6, Sep. 15, 2002, pp. 2225-2234.

(56) References Cited

OTHER PUBLICATIONS

Peranteau et al., "In Utero Hematopoietic Cell Transplantation: What are the Important Questions?", Fetal Diagnosis and Therapy, vol. 19, No. 1, Jan.-Feb. 2004, pp. 9-12.

Persons, "Lentiviral Vector Gene Therapy: Effective and Safe?", Molecular Therapy, vol. 18, No. 5, May 2010, pp. 861-862.

Petrus et al., "Gene Therapy Strategies For Hemophilia: Benefits Versus Risks", Journal of Gene Medicine, vol. 12, No. 10, Oct. 1, 2010, pp. 797-809.

Peyvandi , "Carrier Detection and Prenatal Diagnosis of Hemophilia in Developing Countries", Seminars in Thrombosis and Hemostasis, vol. 31, No. 5, Nov. 2005, pp. 544-554.

Pike-Overzet et al., "New Insights and Unresolved Issues Regarding Insertional Mutagenesis in X-Linked SCID Gene Therapy", Molecular Therapy, vol. 15, No. 11, Nov. 2007, pp. 1910-1916.

Pinto et al., "Molecular Diagnosis of Haemophilia A at Centro Hospitalar de Coimbra in Portugal: Study of 103 Families—15 New Mutations", Haemophilia, vol. 18, No. 1, Jan. 2012, pp. 129-138.

Pipe et al., "Differential Interaction of Coagulation Factor VIII and Factor V with Protein Chaperones Calnexin and Calreticulin", Journal of Biological Chemistry, vol. 273, No. 14, Apr. 3, 1998, pp. 8537-8544.

Popp et al., "Mesenchymal Stem Cells as Immunomodulators After Liver Transplantation", Liver Transplantation, vol. 15, No. 10, Oct. 2009, pp. 1192-1198.

Porada et al., "Adult Mesenchymal Stem Cells: A Pluripotent Population with Multiple Applications", Current Stem Cell Research and Therapy, vol. 1, Sep. 2006, pp. 365-369.

Porada et al., "Clinical and Molecular Characterization of a Re-established Line of Sheep Exhibiting Hemophilia A", Journal of Thrombosis and Haemostasis, vol. 8, No. 2, Feb. 2010, pp. 276-285.

Porada et al., "Gene Therapy: The Promise of a Permanent Cure", North Carolina Medical Journal, vol. 74, No. 6, Nov.-Dec. 2013, pp. 526-529.

Porada et al., "Hemophilia A: An Ideal Disease to Correct in Utero", Frontiers In Pharmacology, vol. 5, Article 276, Dec. 11, 2014, pp. 1-12.

Porada et al., "Mesenchymal Stem Cells as Therapeutics and Vehicles for Gene and Drug Delivery", Advanced Drug Delivery Reviews, vol. 62, No. 12, Sep. 30, 2010, pp. 1156-1166.

Porada et al., "Phenotypic Correction of Hemophilia A in Sheep by Postnatal Intraperitoneal Transplantation of FVIII-Expressing MSC", Experimental Hematology, vol. 39, No. 12, Dec. 2011, pp. 1124-1135.

Porada et al., "Postnatal Transplantation of FVIII-Expressing MSC Phenotypically Corrects Hemophilia A", Molecular Therapy, vol. 19, No. 7, Jul. 2011, p. 1364.

Porada et al., "The Sheep Model of in Utero Gene Therapy", Fetal Diagnosis and Therapy, vol. 19, No. 1, Jan.-Feb. 2004, pp. 23-30.

Porada et al., "Treatment of Hemophilia A in Utero and Postnatally Using Sheep as a Model for Cell and Gene Delivery", Journal of Genetic Syndromes & Gene Therapy, vol. S1, May 25, 2012, pp. 1-26.

Qin et al., "Systematic Comparison of Constitutive Promoters and the Doxycycline-Inducible Promoter", PLoS One, vol. 5, Issue 5, e10611, 2010, pp. 1-6.

Ragni, "The Old and New: PCCs, VIIa, and Long-Lasting Clotting Factors for Hemophilia and Other Bleeding Disorders", American Society of Hematology, vol. 2013, No. 1, Dec. 6, 2013, pp. 44-51.

Rajewsky, "Clonal Selection and Learning in the Antibody System", Nature, vol. 381, No. 6585, Jun. 27, 1996, pp. 751-758.

Rangel-Moreno et al., "Omental Milky Spots Develop in the Absence of Lymphoid Tissue-Inducer Cells and Support B and T Cell Responses to Peritoneal Antigens", Immunity, vol. 30, No. 5, May 22, 2009, pp. 731-743.

Rao et al., "Stem Cell Transplantation in the Normal Nonmyeloablated Host: Relationship Between Cell Dose, Schedule, and Engraftment", Experimental Hematology, vol. 25, No. 2, Feb. 1997, pp. 114-121.

Rawle et al., "Induction of Partial Immune Tolerance To Factor VIII through Prior Mucosal Exposure to The Factor VIII C2 Domain", Journal of Thrombosis and Haemostasis, vol. 4, No. 10, Oct. 2006, pp. 2172-2179.

Reding et al., "CD4+ T Cell Response to Factor VIII in Hemophilia A, Acquired Hemophilia, and Healthy Subjects", Thrombosis and Haemostasis, vol. 82, No. 2, Aug. 1999, pp. 509-515.

Reipert et al., "Mechanisms of Action of Immune Tolerance Induction Against Factor VIII in Patients with Congenital Haemophilia A and Factor VIII Inhibitors", British Journal of Haematology, vol. 136, No. 1, Jan. 2007, pp. 12-25.

Ringden et al., "Mesenchymal Stem Cells for Treatment of Therapy-Resistant Graft-Versus-Host Disease", Transplantation, vol. 81, No. 10., May 27, 2006, pp. 1390-1397.

Rodrigues et al., "Quantitative Correlation Between Transcriptional Levels of ER Chaperone, Peroximal Protein and FVIII Productivity in Human Hek-293 Cell Line", Springerplus, vol. 2, No. 1, Jul. 2013, pp. 1-7.

Rojewski et al., "Phenotypic Characterization of Mesenchymal Stem Cells from Various Tissues", Transfus Med Hemother 2008, vol. 38, 2008, pp. 168-184.

Roncarolo et al., "T Cell Repertoire and Tolerance after Fetal Stem Cell Transplantation", Bone Marrow Transplant, vol. 9, 1992, pp. 127-128.

Rosenberg et al., "Intracellular Trafficking of Factor VIII to Von Willebrand Factor Storage Granules", Journal of Clinical Investigation, vol. 101, No. 3, Feb. 1, 1998, pp. 613-624.

Roybal et al., "Stem Cell and Genetic Therapies for the Fetus", Seminars in Fetal and Neonatal Medicine, vol. 15, No. 1, Feb. 2010, pp. 46-51.

Roybal et al., "Use of Manipulated Stem Cells for Prenatal Therapy", Methods in Molecular Biology, vol. 891, Apr. 2012, pp. 169-181.

Russo-Carbolante et al., "Integration Pattern of HIV-1 Based Lentiviral Vector Carrying Recombinant Coagulation Factor VIII in Sk-Hep and 293T Cells", Biotechnology Letters, vol. 33, No. 1, Jan. 2011, pp. 23-31.

Sack et al., "Immune Responses to Human Factor IX In Haemophilia B Mice of Different Genetic Backgrounds are Distinct and Modified By TLR4", Haemophilia, vol. 21, No. 1, Jan. 2015, pp. 133-139.

Sanada et al., "Mesenchymal Stem Cells Contribute to Endogenous FVIIIc Production", Journal of Cellular Physiology, vol. 228, No. 5, May 2013, pp. 1010-1016.

Santagostino , "More Than a Decade of International Experience with a pdFVIII/VWF Concentrate in Immune Tolerance", Haemophilia, vol. 19, Jan. 2013, pp. 8-11.

Santore et al., "Prenatal Stem Cell Transplantation and Gene Therapy", Clinics in Perinatology, vol. 36, No. 2, Jun. 2009, pp. 451-471.

Sasanakul et al., "Cost-Effectiveness in Establishing Hemophilia Carrier Detection and Prenatal Diagnosis Services in a Developing Country With Limited Health Resources", The Southeast Asian Journal of Tropical Medicine and Public Health, vol. 34, No. 4, Dec. 2003, pp. 891-898.

Sawyer et al., "Ontogeny of Immunity and Leukocytes in the Ovine Fetus and Elevation of Immunoglobulins Related to Congenital Infection", American Journal of Veterinary Research, vol. 39, No. 4, Apr. 1978, pp. 643-648.

Schrepfer et al., "Stem Cell Transplantation: The Lung Barrier", Transplantation Proceedings, vol. 39, No. 2, Mar. 2007, pp. 573-576.

Secunda et al., "Isolation, Expansion and Characterisation of Mesenchymal Stem Cells from Human Bone Marrow, Adipose Tissue, Umbilical Cord Blood and Matrix: A Comparative Study", Cytotechnology 2015, vol. 67, 2015, pp. 793-807.

Selvaraj et al., "Bioengineering of Coagulation Factor VIII for Efficient Expression Through Elimination of a Dispensable Disulfide Loop", Journal of Thrombosis and Haemostasis, vol. 10, No. 1, Jan. 2012, pp. 107-115.

Semenov et al., "Multipotent Mesenchymal Stem Cells From Human Placenta: Critical Parameters for Isolation and Maintenance of Stemness After Isolation", American Journal of Obstetrics and Gynecology, vol. 202, No. 2, Feb. 2010, pp. 193.e1-193.e13.

(56) References Cited

OTHER PUBLICATIONS

Shaaban et al., "A Kinetic Model for the Homing and Migration of Prenatally Transplanted Marrow", Blood, Transplantation, vol. 94, No. 9, Nov. 1, 1999, pp. 3251-3257.

Shaw et al., "Autologous Transplantation of Amniotic Fluid-Derived Mesenchymal Stem Cells Into Sheep Fetuses", Cell Transplantation, vol. 20, No. 7, Aug. 1, 2011, pp. 1015-1031.

Shaw et al., "Clinical Applications of Prenatal and Postnatal Therapy Using Stem Cells Retrieved From Amniotic Fluid", Current Opinion in Gynecology and Obstetrics, vol. 23, No. 2, Apr. 2011, pp. 109-116.

Shaw et al., "Use of Factorial Designs to Optimize Animal Experiments and Reduce Animal Use", ILAR Journal, vol. 43, No. 4, Oct. 1, 2002, pp. 223-232.

Shetty et al., "First-Trimester Prenatal Diagnosis in Haemophilia A and B Families—10 Years Experience from a Centre in India", Prenatal Diagnosis, vol. 26, No. 11, Nov. 2006, pp. 1015-1017.

Shi et al., "Factor VIII Ectopically Targeted to Platelets is Therapeutic in Hemophilia A with High-Titer Inhibitory Antibodies", Journal of Clinical Investigation, vol. 116, No. 7, Jul. 2006, pp. 1974-1982.

Shi et al., "Factor VIII Inhibitors: Von Willebrand Factor Makes a Difference in Vitro and in Vivo", Journal of Thrombosis and Haemostasis, vol. 10, No. 11, Nov. 2012, pp. 2328-2337.

Shi et al., "Targeting FVIII Expression to Endothelial Cells Regenerates a Releasable Pool of FVIII and Restores Hemostasis in a Mouse Model of Hemophilia A", Blood, vol. 116, No. 16, Oct. 21, 2010, pp. 3049-3057.

Sidney et al., "Concise Review: Evidence for CD34 as a Common Marker for Diverse Progenitors", Stem Cells, vol. 32, Apr. 19, 2022, pp. 1380-1389.

Simmons et al., "CD34 Expression by Stromal Precursors in Normal Human Adult Bone Marrow", Blood, vol. 78, Issue 11, 1991, pp. 2848-2853.

Skupsky et al., "B-Cell-Delivered Gene Therapy Induces Functional T Regulatory Cells and Leads to a Loss of Antigen-Specific Effector Cells", Molecular Therapy, vol. 18, No. 8, Aug. 2010, pp. 1527-1535.

Sokal et al., "Mesenchymal Stem Cell Treatment for Hemophilia: A Review of Current Knowledge", Journal of Thrombosis and Haemostasis, vol. 12, No. 1, Jun. 2015, pp. S161-S166.

Soland et al., "Modulation of Human Mesenchymal Stem Cell Immunogenicity Through Forced Expression of Human Cytomegalovirus US Proteins", PLoS One, vol. 7, No. 5, May 30, 2012, pp. 1-15.

Sorrentino, "Assessing the Risk of T-Cell Malignancies in Mouse Models of SCID-X1", The American Society of Gene & Cell Therapy, vol. 18, No. 5, May 2010, pp. 868-870.

Sotiropoulou et al., "Interactions Between Human Mesenchymal Stem Cells and Natural Killer Cells", Stem Cells, vol. 24, No. 1, Jan. 2006, pp. 74-85.

Spencer et al., "Lentiviral Vector Platform for Production of Bioengineered Recombinant Coagulation Factor VIII", Molecular Therapy, vol. 19, No. 2, Feb. 2011, pp. 302-309.

Stavnezer et al., "Evolution of Isotype Switching", Seminars in Immunology, vol. 16, No. 4, Aug. 2004, pp. 257-275.

Stavnezer, "Immunoglobulin Class Switching", Current Opinion in Immunology, vol. 8, No. 2, Apr. 1996, pp. 199-205.

Stewart et al., "Long-Term Engraftment of Normal and Post-5-Fluorouracil Murine Marrow Into Normal Nonmyeloablated Mice", Blood, vol. 81, No. 10, May 15, 1993, pp. 2566-2571.

Stewart et al., "Lymphohematopoietic Engraftment in Minimally Myeloablated Hosts", Blood, vol. 91, No. 10, May 15, 1998, pp. 3681-3687.

Stripecke et al., "Immune Response to Green Fluorescent Protein: Implications for Gene Therapy", Gene Therapy, vol. 6, No. 7, Aug. 9, 1999, pp. 1305-1312.

Su et al., "Gene Expression Imaging by Enzymatic Catalysis of a Fluorescent Probe via Membrane-anchored Beta-glucuronidase", Gene Therapy, vol. 14, No. 7, Jan. 18, 2007, pp. 565-574.

Swaroop et al., "Mutagenesis of a Potential Immunoglobulin-Binding Protein-Binding Site Enhances Secretion of Coagulation Factor VIII", Journal of Biological Chemistry, vol. 272, No. 39, Sep. 26, 1997, pp. 24121-24124.

Takahashi et al., "Immune Tolerance Induction Using Fetal Directed Placental Injection in Rodent Models: A Murine Model", PLoS One, vol. 10, No. 4, Apr. 13, 2015, pp. 1-10.

Tellez et al., "High Incidence of Vector Integration Near Cancer-Related Genes within Primitive Hematopoietic Stem Cells (HSC) after Fetal Gene Transfer with γ-Retroviral Vectors", Hematologic and Immunologic Gene & Cell Therapy III, vol. 18, May 1, 2010, p. S331.

Terraube et al., "Factor VIII and Von Willebrand Factor Interaction: Biological, Clinical and Therapeutic Importance", Haemophilia, vol. 16, No. 1, Jan. 2010, pp. 3-13.

Themis et al., "Successful Expression of β-Galactosidase and Factor IX Transgenes in Fetal and Neonatal Sheep After Ultrasound-Guided Percutaneous Adenovirus Vector Administration Into the Umbilical Vein", Gene Therapy, vol. 6, Aug. 1999, pp. 1239-1248.

Thierry et al., "Stro-1 Positive and Stro-1 Negative Human Mesenchymal Stem Cells Express Different Levels of Immunosuppression", Blood, vol. 104, No. 11, 2004, 2 pages.

Thomas et al., "Efficient Transduction of Hematopoietic Stem Cells and its Potential for Gene Correction of Hematopoietic Diseases", Methods in Molecular Biology, vol. 1114, Feb. 1, 2014, pp. 441-450.

Thrasher et al., "Gene Therapy: X-SCID Transgene Leukaemogenicity", Nature, vol. 443, No. 7109, Sep. 21, 2006, pp. E5-E6.

Tomchuck et al., "Toll-like Receptors on Human Mesenchymal Stem Cells Drive Their Migration and Immunomodulating Responses", Stem Cells, vol. 26, No. 1, Jan. 2008, pp. 99-107.

Toole et al., "A Large Region (=95 kDa) of Human Factor VIII is Dispensable for in Vitro Procoagulant Activity", Proceedings of the National Academy of Sciences of the United States of America, vol. 83, No. 16, Aug. 1986, pp. 5939-5942.

Touraine et al., "Induction of Transplantation Tolerance in Humans Using Fetal Cell Transplants", Transplantation Proceedings, vol. 37, No. 1, Jan.-Feb. 2005, pp. 65-66.

Touraine, "Transplantation of Human Fetal Liver Cells Into Children or Human Fetuses", Human Fetal Tissue Transplantation, Springer, 2013, pp. 205-218.

Touraine et al., "Transplantation Tolerance Induced in Humans at the Fetal or The Neonatal Stage", Journal of Transplantation, vol. 2011, Aug. 2011, pp. 1-4.

Touzot et al., "Gene Therapy for Inherited Immunodeficiency", Expert Opinion on Biological Therapy, vol. 14, No. 6, 2014, pp. 789-798.

Tran, "Enhancing mRNA Stability Through the Addition of Stabilizing Untranslated Regions", Massachusetts Institute of Technology, Jun. 2011, pp. 1-20.

Tran et al., "Induction of Stable Prenatal Tolerance to Beta-galactosidase by in Utero Gene Transfer Into Preimmune Sheep Fetuses", Blood, vol. 97, No. 11, Jun. 1, 2001, pp. 3417-3423.

Trobridge et al., "Large Animal Models of Hematopoietic Stem Cell Gene Therapy", Gene Therapy, vol. 17, No. 8, Apr. 29, 2010, pp. 939-948.

Troeger et al., "In Utero Haematopoietic Stem Cell Transplantation: Experiences in Mice, Sheep and Humans", Swiss Medical Weekly, vol. 136, Nos. 31-32, Aug. 5, 2006, pp. 498-503.

Tsai et al., "Retroviral Transduction of Il2rg Into Cd34(+) Cells from X-linked Severe Combined Immunodeficiency Patients Permits Human T- and B-cell Development in Sheep Chimeras", Blood, vol. 100, No. 1, Jul. 1, 2002, pp. 72-79.

Tsui et al., "Noninvasive Prenatal Diagnosis of Hemophilia by Microfluidics Digital PCR Analysis of Maternal Plasma DNA", Blood, vol. 117, No. 13, Mar. 31, 2011, pp. 3684-3691.

Van Damme et al., "Bone Marrow Mesenchymal Cells for Haemophilia A Gene Therapy Using Retroviral Vectors With Modified Long-Terminal Repeats", Haemophilia, vol. 9, No. 1, Jan. 2003, pp. 94-103.

(56)　　　　References Cited

OTHER PUBLICATIONS

Verbruggen et al., "The Nijmegen Modification of the Bethesda Assay for Factor VIII:C Inhibitors: Improved Specificity and Reliability", Thrombosis and Haemostasis, vol. 73, No. 2, Feb. 1995, pp. 247-251.

Mdarsson et al., "IgG Subclasses and Allotypes: From Structure to Effector Functions", Frontiers in Immunology, vol. 5, No. 520, Oct. 20, 2014, pp. 1-17.

Vrecenak et al., "In Utero Hematopoietic Cell Transplantation—Recent Progress and the Potential for Clinical Application", Cytotherapy, vol. 15, No. 5, May 2013, pp. 525-535.

Vrecenak et al., "Stable Long-Term Mixed Chimerism Achieved in a Canine Model of Allogeneic in Utero Hematopoietic Cell Transplantation", Blood, vol. 124, No. 12, Sep. 18, 2014, pp. 1987-1995.

Waddington et al., "In Utero Gene Transfer of Human Factor IX to Fetal Mice Can Induce Postnatal Tolerance of the Exogenous Clotting Factor", Blood, vol. 101, No. 4, Feb. 15, 2003, pp. 1359-1366.

Waddington et al., "Permanent Phenotypic Correction of Hemophilia B in Immunocompetent Mice by Prenatal Gene Therapy", Blood, vol. 104, No. 9, Nov. 1, 2004, pp. 2714-2721.

Walsh et al., "Impact of Inhibitors on Hemophilia a Mortality in the United States", American Journal of Hematology, vol. 90, No. 5, May 2015, pp. 400-405.

Wang et al., "The Mesenchymal Stem Cells Derived From Transgenic Mice Carrying Human Coagulation Factor VIII Can Correct Phenotype in Hemophilia a Mice", Journal of Genetics and Genomics, vol. 40, No. 12, Dec. 20, 2013, pp. 617-628.

Ward et al., "Codon Optimization of Human Factor VIII cDNAs Leads to High-Level Expression", Blood, vol. 117, No. 3, Jan. 20, 2011, pp. 798-807.

Watts et al., "Hematopoietic Stem Cell Expansion and Gene Therapy", Cytotherapy, vol. 13, No. 10, Nov. 2011, pp. 1164-1171.

Wegorzewska et al., "Fetal Intervention Increases Maternal T Cell Awareness of the Foreign Conceptus and Can Lead to Immune-Mediated Fetal Demise", Journal of Immunology, vol. 192, No. 4, Feb. 15, 2014, pp. 1938-1945.

Whelan et al., "Distinct Characteristics of Antibody Responses against Factor VIII in Healthy Individuals and in Different Cohorts of Hemophilia A Patients", Blood, vol. 121, No. 6, Feb. 7, 2013, pp. 1039-1048.

Williams et al., "Concise Review: Lessons Learned From Clinical Trials of Gene Therapy in Monogenic Immunodeficiency Diseases", Stem Cells Translational Medicine, vol. 3, No. 5, May 2014, pp. 636-642.

Wolfs et al., "IL-1α Mediated Chorioamnionitis Induces Depletion of FoxP3+ Cells and Ileal Inflammation in the Ovine Fetal Gut", PLoS One, vol. 6, No. 3, Mar. 29, 2011, pp. 1-9.

Yamagami et al., "Expression of HLA-G1 and G5 Enables Human Mesenchymal Stem Cells to Engraft at High Levels Across Xenogeneic Barriers Following Transplantation into Immunocompetent Recipients", Blood, vol. 110, No. 11, Nov. 16, 2007, 2 pages.

Yamagami et al., "Expression of Molecules Involved in Fetal-Maternal Tolerance Allows Human Mesenchymal Stem Cells to Engraft at High Levels across Immunologic Barriers", Blood, vol. 112, No. 11, Nov. 16, 2008, 2 pages.

Yang et al., "Options for Tracking GFP-labeled Transplanted Myoblasts Using in Vivo Fluorescence Imaging: Implications for Tracking Stem Cell Fate", BMC Biotechnology, vol. 14, No. 55, Jun. 12, 2014, pp. 1-8.

Yank et al., "Systematic Review: Benefits and Harms of in-hospital Use of Recombinant Factor VIIa for Off-label Indications", Annals of Internal Medicine, vol. 154, No. 8, Apr. 19, 2011, pp. 529-540.

Zakas et al., "Development and Characterization of Recombinant Ovine Coagulation Factor VIII", PLoS One, vol. 7, No. 11, Nov. 9, 2012, pp. 1-9.

Zakas et al., "Development and Characterization of Recombinant Ovine Factor VIII", Blood, American Society of Hematology, vol. 118, No. 21, Nov. 18, 2011, p. 1193.

Zhang et al., "Bleeding Due to Disruption of a Cargo-Specific ER-to-Golgi Transport Complex", Nature Genetics, vol. 34, No. 2, Jun. 2003, pp. 220-225.

Zhou et al., "Boosting Interleukin-10 Production: Therapeutic Effects and Mechanisms", Current Drug Targets—Immune, Endocrine & Metabolic Disorders, vol. 5, No. 4, Dec. 2005, pp. 465-475.

Trevisan, B., et al., "Delivery of Fviii-mcoET3 to Previously Untreated Sheep Using Human Placental Cells Enables Durable Elevation of Plasma FVIII Levels and Avoids Inhibitor Formation." Blood, 2020, 136 (Supplement 1): 34, pp. 1-3.

Horwitz, E., et al. "Clarification of the nomenclature for MSC: The International Society for Cellular Therapy position statement." Cytotherapy, 2005; 7(5): pp. 393-395.

Horwitz, E., et al., "Mesenchymal Stromal Cells." Curr. Opin. Hematol., 2006, 13(6): pp. 419-425.

Stem, C. et al., "Investigating Optimal Autologous Cellular Platforms for Prenatal or Perinatal Factor VII Delivery to Treat Hemophilia A." Frontiers in Cell and Developmental Biology, 2021, vol. 9, Article 678117: pp. 1-14.

El-Akabawy, N., et al., "Defining the Optimal FVII Transgene for Placental Cell-Based Gene Therapy to Treat Hemophilia A." Molecular Therapy-Methods & Clinical Development, vol. 17, Jun. 2020, pp. 465-477.

Rodriguez, M., et al., "Transplanting FVIII/ET3-secreting cells in fetal sheep increases FVIII levels long-term without inducing immunity or toxicity." Nature Communications, vol. 14, Article 4206, Jul. 14, 2023, pp. 1-17.

Benova, A., et al., "Obesity-Induced Changes in Bone Marrow Homeostasis." Frontiers in Endocrinology, 2020, vol. 11, Article 294, pp. 1-15.

Ramamurthy, R., et al., "Comparison of different gene addition strategies to modify placental derived-mesencymal stromal cells to produce FVIII." Frontiers in Immunology, 2022, vol. 13, Article 954984, pp. 1-19.

"A New Cell and Gene Therapy Approach to Treat Common Bleeding Disorder." News Release, Atrium Health, Wake Forest Baptist, Jul. 30, 2020, pp. 1-4. Available at https://newsroom.wakehealth.edu/news-releases/2020/07/a-new-cell-and-gene-therapy-approach-to-treat-common-bleeding-disorder.

* cited by examiner

Anti-bovine CD11b

Anti-ovine CD34

Anti-ovine CD146

CD146          CD90

Adipogenic Differentiation

Osteogenic Differentiation

α-smooth muscle actin    Vimentin

Map of EF1α-[oFVIII] Lentivector

Map of CAG vWF Lentivector

FIG. 5
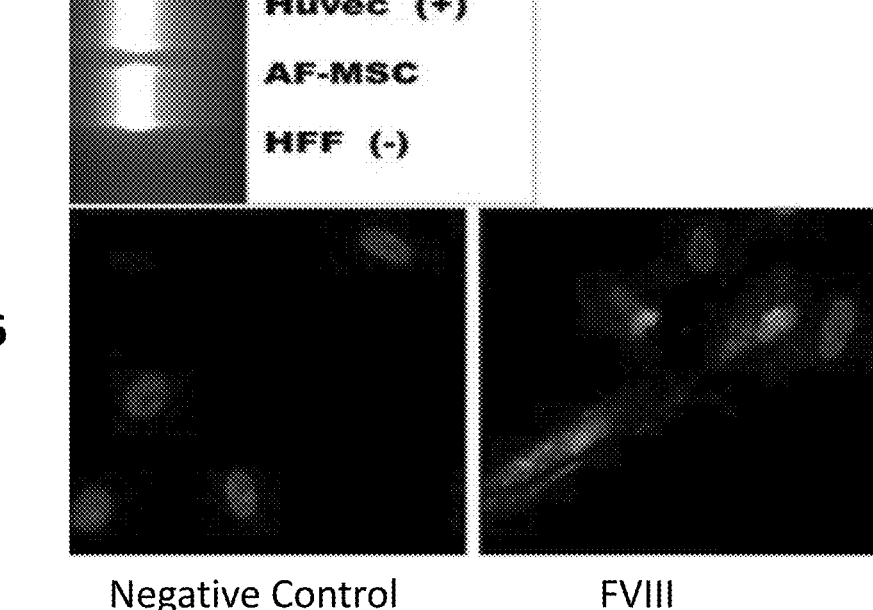
Negative Control                    FVIII
FIG. 6
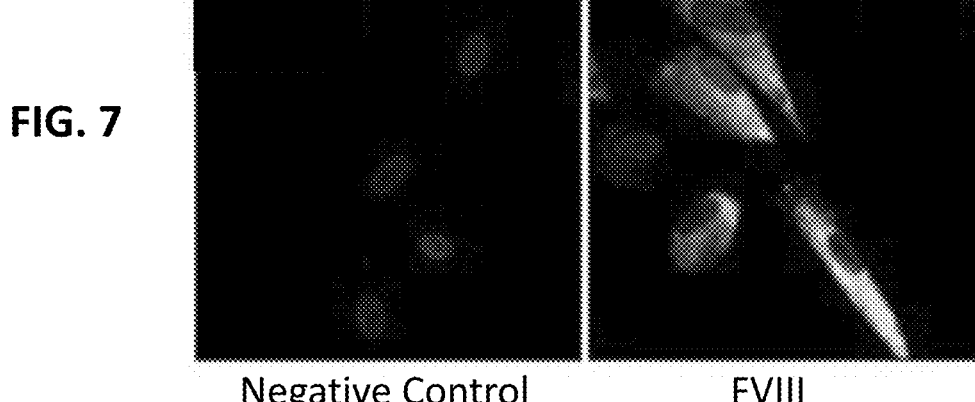
Huvec (+)
AF-MSC
HFF (-)
Negative Control                    FVIII
FIG. 7
Negative Control                    FVIII

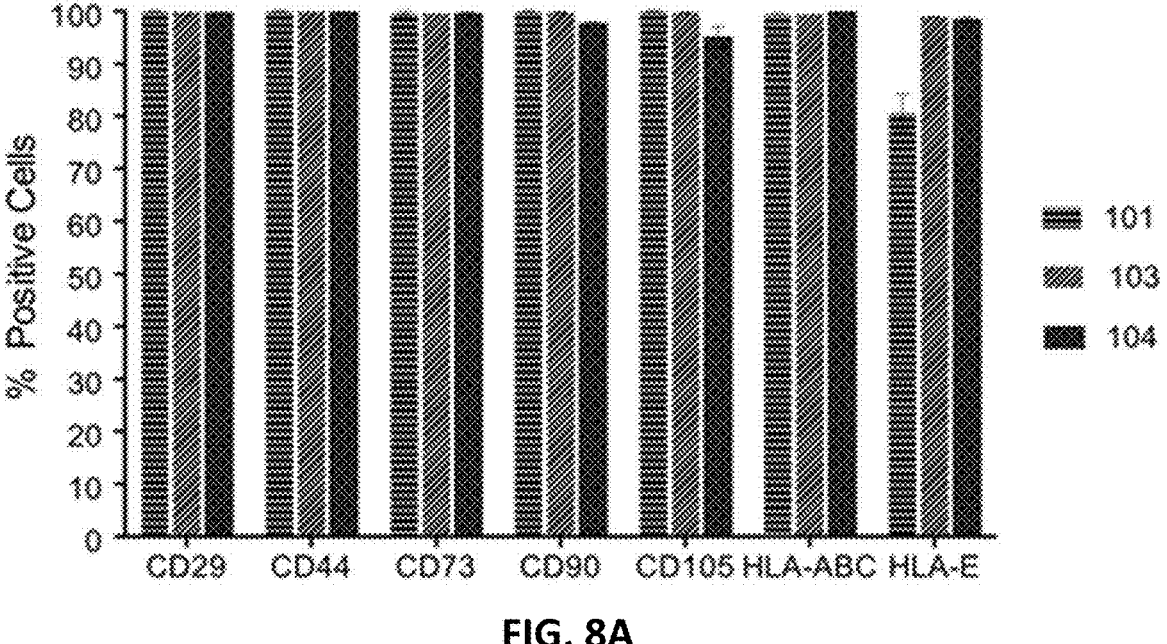
FIG. 8A
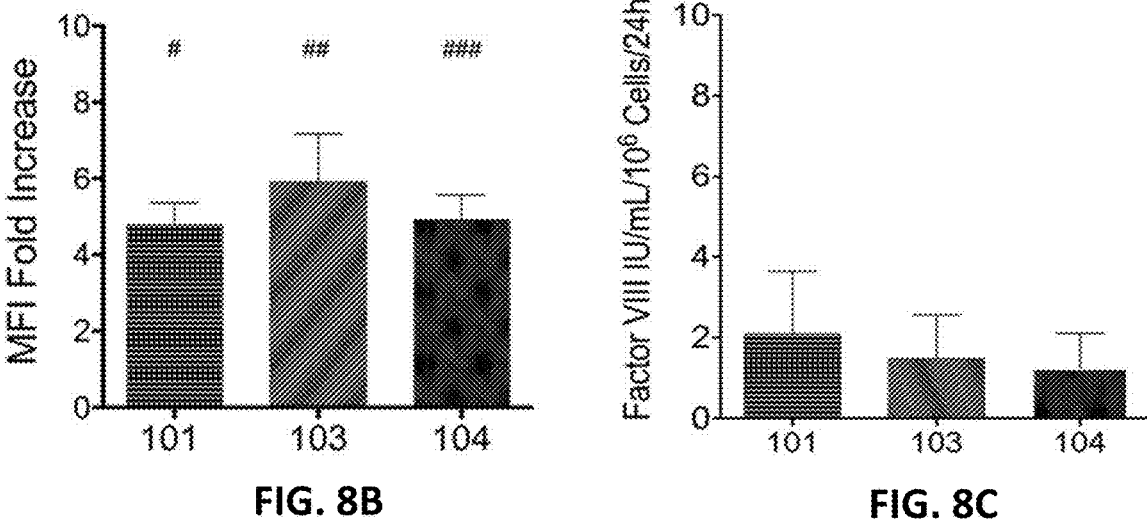
FIG. 8B                    FIG. 8C

SEQUENCE LISTING

```
Sequence total quantity: 33
SEQ ID NO: 1              moltype = DNA  length = 146
FEATURE                  Location/Qualifiers
misc_feature             1..146
                         note = synthetic HNF1-shortABP-Syn0-TSS
source                   1..146
                         mol_type = other DNA
                         organism = synthetic construct
SEQUENCE: 1
gttaatcatt aagtcgttaa tttttgtggc ccttgcgatg tttgctctgg ttaataatct  60
caggacaaac agaggttaat aattttccag atctctctga gcaatagtat aaaaggccag  120
cagcagcctg accacatctc atcctc                                       146

SEQ ID NO: 2              moltype = DNA  length = 159
FEATURE                  Location/Qualifiers
misc_feature             1..159
                         note = synthetic ABPshort-HP1-AFP-TSS
source                   1..159
                         mol_type = other DNA
                         organism = synthetic construct
SEQUENCE: 2
gttaattttt gtggcccttg cgatgtttgc tctggttaat aatctcagga caaacataca  60
ttttcagtca tatgtttgct cactgaaggt tactagttaa caggcatccc ttaaacagga  120
tataaaaggc cagcagcagc ctgaccacat ctcatcctc                         159

SEQ ID NO: 3              moltype = DNA  length = 152
FEATURE                  Location/Qualifiers
misc_feature             1..152
                         note = HNF1-ABP-Syn0
source                   1..152
                         mol_type = other DNA
                         organism = synthetic construct
SEQUENCE: 3
gttaatcatt aagtcgttaa tttttaaaaa gcagtcaaaa gtccaagtgg cccttgcgag  60
catttactct ctctgtttgc tctggttaat aatctcagga gcacaaacag aggttaataa  120
ttttccagat ctctctgagc aatagtataa aa                                152

SEQ ID NO: 4              moltype = DNA  length = 150
FEATURE                  Location/Qualifiers
misc_feature             1..150
                         note = synthetic SP1-ABP-Syn0
source                   1..150
                         mol_type = other DNA
                         organism = synthetic construct
SEQUENCE: 4
tgggcggagt gtcgttaatt tttaaaaagc agtcaaaagt ccaagtggcc cttgcgagca  60
tttactctct ctgtttgctc tggttaataa tctcaggagc acaaacagag gttaataatt  120
ttccagatct ctctgagcaa tagtataaaa                                   150

SEQ ID NO: 5              moltype = DNA  length = 137
FEATURE                  Location/Qualifiers
misc_feature             1..137
                         note = synthetic ABP-Syn0
source                   1..137
                         mol_type = other DNA
                         organism = synthetic construct
SEQUENCE: 5
gttaattttt aaaaagcagt caaaagtcca agtggccctt gcgagcattt actctctctg  60
tttgctctgg ttaataatct caggagcaca aacagaggtt aataattttc cagatctctc  120
tgagcaatag tataaaa                                                 137
```

-continued

```
SEQ ID NO: 6              moltype = DNA   length = 172
FEATURE                   Location/Qualifiers
misc_feature              1..172
                          note = synthetic ABP-HP1-AFP
source                    1..172
                          mol_type = other DNA
                          organism = synthetic construct
SEQUENCE: 6
gttaattttt aaaaagcagt caaaagtcca agtggccctt gcgagcattt actctctctg   60
tttgctctgg ttaataatct caggagcaca aacagaggtt aataattttc agtcatatgt   120
ttgctcactg aaggttacta gttaacaggc atcccttaaa caggatataa aa            172

SEQ ID NO: 7              moltype = DNA   length = 4377
FEATURE                   Location/Qualifiers
misc_feature              1..4377
                          note = synthetic hcoAn53
source                    1..4377
                          mol_type = other DNA
                          organism = synthetic construct
SEQUENCE: 7
atgcagattg agctgtccac ttgctttttc ctgtgcctgc tgcagttttc attttccgcc   60
actagaagat actacctggg ggctgtcgaa ctgtcctggg attacatgca gtccgacctg   120
ctgtctgagc tgcatgtgga cacccgattt ccacctcgcg tcccacgaag cttcccccttt  180
aatacatccg tgatgtacaa gaaaactgtg ttcgtcgagt tcaccgatca cctgttcaac   240
atcgcaaagc cccggccacc ctggatggga ctgctgggcc ctaccatcag agccgaggtg   300
tacgacaccg tggtcattac actgaaaaac atggcaagtc accccgtgtc actgcatgcc   360
gtgggagtct cctactggaa ggcatctgaa ggcgccgagt atgacgatca gactagtcag   420
agagaaaaag aggacgataa ggtgtttccc ggagaatctc ataccatgt gtggcaggtc    480
ctgaaggaga atggccctat ggccagcgac cctccatgcc tgacctactc ctatctgtct   540
cacgtggacc tggtcaaaga tctgaactcc gggctgatcg gagccctgct ggtgtgtcgg   600
gaaggatctc tggctaagga gagaacccag acactgcatc agttcgtgct gctgttcgct   660
gtctttgacg aaggcaaaag ttggcactca gagacaaagg attccctgac tcaggcaatg   720
gactctgcca gtgctagggc atggccaaaa atgcacaccg tgaacggcta cgtcaataga   780
agcctgccag gactgatcgg atgccacagg aagtccgtgt attggcatgt catcggcatg   840
gggaccacac cagaagtcca ctctattttc ctggagggac atacatttct ggtgcggaat   900
cacagacagg ctagcctgga gatctccccc attaccttcc tgacagcaca gactctgctg   960
atggatctgg gccagttcct gctgtttttgc cacatcagct cccaccagca tgatgggatg   1020
gaggcctacg tgaaagtcga cagctgtcca gaggaacccc agctgaggat gaagaacaat  1080
gaggaagagg aagactacga cgatgacctg tatgacagcg agatggatgt ggtccgattc   1140
gatgacgata actcaccccc tttatccag attagaagcg tcgccaagaa acaccctaag   1200
acttgggtgc attacatcgc cgctgaggaa gaggactggg attatgctcc ttccgtgctg   1260
accccagacg atcgcagcta caaatcccag tatctgaaca atggccctca gaggattggg  1320
cgcaagtaca agaaagtgag gttcatggct tataccgatg aaaccttcaa gactcgcgaa   1380
gcaatccagt acgagtccgg aattctgggc ccactgctgt atggggaagt gggagacacc   1440
ctgctgatca ttttcaagaa ccaggcctct aggccctaca atatctatcc tcatggcatt   1500
acagatgtgt ctccctgca cagtggacgc ctgcctaagg gcgtgaaaca cctgaaggac   1560
ctgcctatcc tgccagggga aattttaag tacaaatgga cctgtaccgt cgaggatgga   1620
ccaactaaga gcgaccccag gtgcctgacc cgctactatt ctagtttcat caatctggaa   1680
agagatctgg caagcggact gatcggacca ctgctgattt gttacaaaga gtccgtggat  1740
cagcgaggca accagatgat gtctgacaag cggaatgtga tcctgttctc agtctttgac   1800
gaaaaccgca gctggtatct gaccgagaac atgcagccgat tcctgccaaa tgcagcagga  1860
gtgcagccac aggatcctga gtttcaggct agtaacatca tgcattcaat taatggctac   1920
gtgttcgact cactgcagct gagcgtgtgt ctgcacgagg tcgcttactg gtatatcctg   1980
agcgtcggag cacagacaga tttcctgtcc gtgttctttt ctggctacac ttttaagcat   2040
aaaatggtgt atgaggacac actgactctg ttccctttt ccggcgaaac cgtctttatg   2100
tctatggaga atccagggct gtgggtgctg ggatgccaca actccgattt ccggaataga   2160
ggaatgactg ccctgctgaa agtgtcaagc tgtgaccgga acaccggcga ctactatgaa   2220
gatacatacg aggacatccc aacttatctg ctgtctgaaa acaatgtgat tgagcccaga   2280
agcttcagcc agaatccacc cgtgctgaag cgacaccagc gggaaatcac cctgactacc   2340
ctgcagtcag agcaggaaga gattgattac gacgatacca tcagcattga aacaaaaagg  2400
gaggacttcg atatctatgg ggaagacgag aaccagggac ctcgctcctt ccagaagagg   2460
acacgccatt actttattgc tgcagtggag aggctgtggg attatgggat gtcccgctct   2520
cccacgtcc tgcgaaatcg ggcccagagt ggatcagtgc ctcagttcaa gaaagtggtc   2580
ttccaggagt ttactgcgg gagctttacc cagcctctgt accggggaga actgaacgag  2640
cacctgggac tgctgggccc atatatcaga gcagaagtgg aggataacat tatggtcacc   2700
ttcaagaatc aggccagtcg gccctactca ttttattcct ctctgatcag ctacgaagag   2760
gaccagcgcc agggcgcaga accacgaaaa aacttcgtga gcccaatga gaccaaaaca    2820
tacttttgga aggtgcagca ccatatggct cctacaaaag acgaattcga ttgcaaggcc   2880
tgggcttatt ttagtgacgt ggatctggag aaggacatgc actcagggcc gatcggacct   2940
ctgctgattt gtcatactaa caccctgaat ccagcacacg gacgacaggt gacagtccag   3000
gaattcgctc tgttctttac aatcttcgat gagactaaga gctggtactt cactgaaaac   3060
atggagagaa attgcagggc cccttgtaat atccagatgg aagacccaac attcaaggag   3120
aactacagat ttcatgctat taatggctat gtgatggata ctctgccagg gctggtcatg   3180
gcacaggacc agagaatcag gtggtacctg tgtctatgga ggactaacga gaatatccac   3240
agcattcatt ctccggaca cgtgtttact gtcaggaaga agaagagta taaaatggcc    3300
gtgtacaacc tgtatccagg cgtgttcgaa accgtcgaga tgctgccaag caaggcagga   3360
atctggcgag tggaatgcct gattggcgag cacctgcatg ctgggatgag taccctgttt   3420
ctggtgtact caaaacagtg tcagacacct ctgggaatgg catctggcca tatccggggat   3480
ttccagatta ccgcaagtgg acagtacgga cagtgggctc caaagctggc aagactgcac   3540
```

```
tatagcggct ccatcaacgc ctggtctaca aaagagccct ttagttggat taaggtggac   3600
ctgctggccc ctatgatcat tcatggcatc aaaactcagg gggctaggca gaagttcagt   3660
tcactgtaca tcagccagtt tatcatcatg tactccctgg atgggaagaa atggcagacc   3720
taccgcggga atagcacagg aactctgatg gtgttctttg gaaacgtcga cagctccggc   3780
atcaagcaca acatttttcaa tcctccaatc attgcccgct acatccgact gcaccccacc   3840
cattattcaa ttcgaagcac actgcggatg gaactgatgg gctgcgatct gaactcttgt   3900
agtatgcctc tggggatgga gtctaaggcc atcagtgacg ctcagattac cgcatctagt   3960
tacttcacca atatgtttgc cacatggtca ccaagccagg ctaggctgca cctgcaggga   4020
agaacaaacg cctggaggcc tcaggtgaac aatccaaagg agtggctgca ggtggatttc   4080
cagaaaacta tgaaggtcac cggaatcaca actcagggcg tgaaatcact gctgaccagc   4140
atgtatgtga aggagtttct gatttcaagc tcccaggacg gccaccattg gacactgttc   4200
ctgcagaacg ggaaggtgaa agtcttccag ggaaatcagg attcttttac accagtggtc   4260
aacagtctgg accccctct gctgactcgg tacctgagaa tccacccca gagctgggtc   4320
catcagattg cactgcgact ggaagtgctg ggatgcgagg cacagcagct gtattga       4377
```

SEQ ID NO: 8              moltype = DNA   length = 4359
FEATURE                   Location/Qualifiers
misc_feature             1..4359
                         note = synthetic lcoAn53
source                   1..4359
                         mol_type = other DNA
                         organism = synthetic construct
SEQUENCE: 8

```
atgcagattg agctgagcac ctgcttcttc ctgtgcctgc tgcagttctc attctctgcc   60
accaggagat actacctggg cgccgtggag ctgagctggg actacatgca gtctgacctg   120
ctgtctgagc tgcatgtgga caccaggttc cccccgaag cttcccttc                 180
aacaccagcg tgatgtacaa gaagaccgtg ttcgtggagt tcactgacca cctgttcaac   240
atcgccaagc ccaggccccc ctggatgggc ctgctgggcc ccaccatcag agccgaggtg   300
tacgacaccg tggtcatcac cctgaagaac atggccagcc accccgtctc cctgcacgcc   360
gtgggggtga gctactggaa ggcctctgag ggcgccgagt acgacgacca gaccagccag   420
agggagaagg aggacgacaa ggtgttccct ggggaaagcc acacctacgt gtggcaggtc   480
ctgaaggaga acggccccat ggcctctgac ccccatgcc tgacctacag ctacctgagc   540
cacgtggacc tggtgaagga cctgaactct ggcctgattg gggccctgct ggtgtgcagg   600
gagggcagcc tggccaagga gagaacccag accctgcacc agttcgtgtc gctgttcgtc   660
gtgttcgacg agggcaagag ctggcactct gaaaccaagg atagcctgac tcaggccatg   720
gactctgcct ctgccaggc ctggcccaag atgcacaccg tcaacggcta cgtcaacagg   780
agcctgcctg gcctgattgg ctgccacagg aagagcgtgt actggcatgt gatcggcatg   840
ggcaccaccc tgaggtgca cagcatcttc ctggagggcc acaccttcct ggtcaggaac   900
cacaggcagg ccagcctgga gatcagcccc atcacctcc tgaccgccca gaccctgctg   960
atggacctgg gccagttcct gctgttctgc cacatctcca gccaccagca cgacggcatg   1020
gaggcctacg tgaaagtgga cagctgccct gaggagcccc agctgaggat gaagaacaac   1080
gaggaggagg aggactatga tgacgacctg tatgacagcg agatggacgt ggtcaggttc   1140
gacgacgaca cagcccccc tttcatccag atcaggagcg tggccaagaa gcacccccaag   1200
acctgggtgc actacatcgc tgctgaggag gaggactggg actatgcccc ctccgtgctg   1260
acccctgatg acaggagcta caagagccag tacctgaaca atggccccca gaggattggc   1320
aggaagtaca agaaagtcag gttcatggcc tacactgatg aaaccttcaa gaccaggagg   1380
gccatccagt acgagtctgg catcctgggc cccctgctgt acgggaggt ggggacacc   1440
ctgctgatca tcttcaagaa ccaggccagc aggccctaca acatctaccc ccatggcatc   1500
accgacgtga gcccctgca cagcggaagg ctgcctaagg gggtgaagca cctgaaaagac   1560
ctgcccatcc tgcctgggga gatcttcaag tacaagtgga ctgtgactgt ggaggacggc   1620
cccaccaaga gcgacccccag gtgcctgacc agatactaca gcagcttcat caacctgag   1680
agggacctgg cctctggcct gattggcccc ctgctgatct gctacaagga gtctgtggac   1740
cagaggggca accagatgat gagcgacaag aggaacgtga tcctgttctc tgtcttcgac   1800
gagaacagga gctggtacct gaccgagaac atgcagaggt tcctgcccaa cgcagctggg   1860
gtgcagccac aggacccga gttccaggcc agcaacatca tgcacagcat caatggctac   1920
gtgttcgaca gcctgcagct gagcgtgtgc ctgcacgagg tggcctactg gtacatcctg   1980
agcgtcggcg cccagaccga cttcctgagc gtgttcttct ctggctacac cttcaagcac   2040
aagatggtgt atgaggacac cctgaccctg ttcccctca tgagcatgga gaaccctggc   2100
ctgtgggtgc tgggctgcca caacagcgac ttcaggaaca ggggcatgac tgccctgctg   2160
aaagtctcca gctgtgaccg gaacaccggg gactactacg aggacacata cgaggacatc   2220
ccaacttacc tgctgagcga aaacaatgtg atcgagccca ggagcttctc tcagaacccc   2280
ccagtgctga gaggcacca gagggagatc accctgacca ccctgcagtc tgagcaggag   2340
gagatcgact atgatgacac catcagcatt gagacaaaga gggaggactt cgacatctac   2400
ggggaggaca gaaccaggg acccaggagc ttccagaaga gaccaggca ctacttcatt   2460
gctgctgtgg agaggctgtg ggactatggc atgtcccgca gccccatgt gctgaggaac   2520
agggcccagt ctggcagcgt gccccagttc aagaaagtcg tgttccagga gttcaccgac   2580
ggcagcttca cccagcccct gtacagaggg agctgaacg agcacctggg cctgctgggc   2640
ccctacatca gggccgaggt ggaggacaaa atcatggtga ccttcaagaa ccaggccagc   2700
aggccctaca gcttctacag cagcctgatc agctacgagg aggaccagag gcagggggct   2760
gagcccagga gaaactttgt gaagcccaat gaaaccaaga cctacttctg gaaggtgcag   2820
caccacatgg cccccaccaa ggacgagttc gactgcaagg cctgggccta cttctctgac   2880
gtggacctgg agaaggacat gcactctggc ctgattggcc ccctgctgat ttgccacacc   2940
aacaccctga accctgccca tggcaggcag gtgactgtgc aggagttcgc cctgttcttc   3000
accatcttcg atgaaaccaa gagctggtac ttcactgaga acatggagag gaactgcagg   3060
gcccctgca acatccagat ggaggacccc accttcaagg agaactacag gttccatgcc   3120
atcaatggct acgtgatgga cacctgcct ggcctggtca tggcccagga ccagaggatc   3180
aggtggtatc tgctgagcat gggcagcaac gagaacatcc acagcatcca cttctctggc   3240
cacgtgttca ctgtgaggaa gaaggaggag tacaagatgg ccgtgtacaa cctgtaccct   3300
ggggtgttcg aaaccgtgga gatgctgccc agcaaggcg gcatctggag ggtggagtgc   3360
```

-continued

```
ctgattgggg agcacctgca cgccggcatg agcaccctgt tcctggtgta cagcaaacag   3420
tgccagaccc ccctgggcat ggcctctggc cacatcaggg acttccagat cactgcctct   3480
ggccagtacg gccagtgggc ccccaagctg gccaggctgc actactccgg aagcatcaat   3540
gcctggagca ccaaggagcc cttcagctgg atcaaagtgg acctgctggc ccccatgatc   3600
atccacgcca tcaagaccca gggggccagg cagaagttct ccagcctgta catcagccag   3660
ttcatcatca tgtacagcct ggacggcaag aagtggcaga cctacagggg caacagcacc   3720
ggcaccctga tggtgttctt cggcaacgtg gacagcagcg gcatcaagca caacatcttc   3780
aacccccca tcatcgccag atacatcagg ctgcacccca cccactacag catcaggagc   3840
accctgagga tggagctgat gggctgtgac ctgaacagct gcagcatgcc cctgggcatg   3900
gagagcaagg ccatctctga cgcccagatc actgcctcca gctacttcac caacatgttt   3960
gccacctgga gccccagcca ggccaggctg cacctgcagg gcaggacaaa tgcctggagg   4020
ccccaggtca acaaccccaa ggagtggctg caggtggact tccagaagac catgaaggtg   4080
actgggatca ccacccaggg ggtgaagagc ctgctgacca gcatgtacgt gaaggagttc   4140
ctgatctcca gcagccagga cggccaccat tggaccctgt tcctgcagaa tggcaaggtg   4200
aaggtgttcc agggcaacca ggacagcttc acccctgtgg tcaacagcct ggacccccc   4260
ctgctgacca gatacctgag gatccacccc cagagctggg tgcaccagat cgccctgagg   4320
ctggaggtgc tgggctgtga ggcccagcag ctgtactga                          4359
```

```
SEQ ID NO: 9             moltype = DNA  length = 4404
FEATURE                  Location/Qualifiers
misc_feature             1..4404
                         note = synthetic lcoET3 with CpGs
source                   1..4404
                         mol_type = other DNA
                         organism = synthetic construct
SEQUENCE: 9
atgcagctgg aactgtctac ctgtgtgttt ctgtgtctgc tgcctctggg gttttctgct   60
atccgccgct actatctggg agccgtggag ctgtcctggg actacaggca gagcgagctg   120
ctgagagaac tgcacgtgga taccagattc ccagctaccg ctccaggagc tctgcctctg   180
ggcccatccg tgctgtacaa gaaaaccgtc ttcgtggagt ttaccgacca gctgttcagc   240
gtggccaggc caagaccacc ttggatggga ctgctgggac caaccatcca ggctgaggtg   300
tacgataccg tggtcgtgac cctgaaaaac atggcctccc atcccgtgag cctgcacgct   360
gtcggggtgt ccttctggaa gtccagcgag ggagccgagt acgaagacca tacctcccag   420
cgcgagaaag aagacgataa ggtgctgcct ggcaaaagcc agacctatgt ctggcaggtg   480
ctgaaggaga acggaccaac cgctagcgac ccaccatgcc tgacctactc ttatctgtcc   540
cacgtcgatc tggtgaagga cctgaattcc ggactgatcg gagctctgct ggtgtgtaga   600
gagggaagcc tgaccagaga aagaacccag aacctgcatg agttcgtcct gctgttcgcc   660
gtgtttgacg aaggggaagag ctggcactct gcccgcaatg actcctggac cagagctatg   720
gatccagctc ctgctagagc tcagcctgct atgcacaccg tcaacggcta cgtgaatcgc   780
tctctgccag gactgatcgg ctgccataag aaaagcgtct attggcacgt gatcggaatg   840
ggcaccagcc ccgaggtgca ttctatcttc ctggaaggcc acacctttct ggtcaggcac   900
catagacagg cctctctgga gatctcccct ctgaccttcc tgaccgctca gacctttctg   960
atggacctgg ggcagttcct gctgttttgc catatctctt cccaccatca cggaggaatg   1020
gaggctcacg tcagggtgga atcctgtgct gaggaaccac agctgagaag aaaggctgat   1080
gaggaagagg actacgacga taacctgtat gacagcgata tggacgtcgt gcgcctggac   1140
ggcgacgatg tcagcccttt catccagatc cggtctgtgg ccaagaaaca tccaaagacc   1200
tgggtccact acatcgccgc tgaagaggaa gattgggact atgcccccct ggtgctggct   1260
cctgacgata gatcctacaa aagccagtat ctgaacaatg ggcccagcg catcggacgg   1320
aagtacaaga aagtgaggtt catggcctat accgacgaga cctttaagac cagagaggct   1380
atccagcacg aatccgggat cctgggacct ctgctgtacg gcgaagtggg ggataccctg   1440
ctgatcatct tcaagaacca ggcctccagg ccatacaata tctatcccca tggcatcacc   1500
gacgtgagac cactgtacag caggagactg cccaaggggg tcaaacacct gaaggatttc   1560
cccatcctgc ctggagagat ctttaagtat aaatggaccg tcaccgtgga agacgggcct   1620
accaagtccg atccacgctg cctgacccgg tactatagct ctttcgtgaa catggagaga   1680
gacctggcta gcggactgat cggacccctg ctgatctgtt acaaagagag cgtggaccag   1740
aggggcaacc agatcatgtc tgataagaga aatgtcatcc tgttctccgt gtttgacgag   1800
aaccgcagct ggtacctgac cgagaacatc agcggttcc tgccaaatcc agctggagtg   1860
cagctggagg acccagaatt tcaggcttcc aacatcatgc atagcatcaa tggctacgtg   1920
ttcgatagcc tgcagctgtc tgtctgcctg cacgaggtgg cctactggta tatcctgtcc   1980
atcggcgctc agaccgactt cctgtccgtg ttctttagcg ggtacacctt taagcataaa   2040
atggtgtatg aggataccct gaccctgttc cccttttctg cgagaccgt gttcatgtcc   2100
atggaaaacc ctgcctgtg gatcctgggg tgccacaaca gcgacttcag gaatagagga   2160
atgaccgccc tgctgaaagt gtccagctgt gataagaata ccggcgatta ctatgaggac   2220
tcttacgaag atatctccgc ttatctgctg agcaagaaca atgccatcga gcccaggtca   2280
ttcgctcaga actccagacc tccaagcgct tctgctccta agccacctgt gctgagaaga   2340
catcagaggg acatctccct gcctaccttc agccagagg aagataaaat ggactacgac   2400
gatatcttca gcaccgagac caaggggaa gattttgaca tctatggaga ggacgaaaac   2460
caggatccaa gatccttcca gaagagaacc agacactact ttatcgccgc tgtggagcag   2520
ctgtgggact atgggatgtc cgaaagccca cgggccctga ggaacagagc tcagaatgga   2580
gaggtgcccc gcttcaagaa agtcgtgttc cgggagtttg ccgacggcag ctttacccag   2640
ccatcttaca gggggagct gaacaagcat ctggggctgc tgggacccta tcagagcc     2700
gaggtcgaag ataacatcat ggtgaccttc aagaatcagg cttctcgccc ctactccttt   2760
tattcttccc tgatctccta ccctgacgat caggagcagg cgcgcgaacc taggcacaac   2820
ttcgtgcaga caaatgagac cagaacctac ttttggaagg tgcagcatca catggctccc   2880
accgaggatg aattcgactg caaagcttgg gcctattttt ccgatgtcga cctggagaag   2940
gacgtgcata cgcgcctgat cgggcctctg ctgatctgtc gcgccaacac cctgaatgct   3000
gctcacggaa gacaggtcac cgtgcaggag ttcgctctgt tctttaccat ctttgacgaa   3060
accaagagct ggtacttcac cgagaacgtg aaaggaatt gcagagcccc ctgtcatctg   3120
cagatggagg accctaccct gaaggaaaac tacaggttcc acgccatcaa tggatatgtc   3180
```

```
atggataccc tgcccggcct ggtcatggct cagaaccagc gcatccggtg gtacctgctg  3240
tctatgggat ccaacgagaa tatccatagc atccacttct ctggccatgt cttttccgtg  3300
aggaagaaag aggaatacaa aatggccgtg tacaatctgt atcctggggt cttcgagacc  3360
gtggaaatgc tgccaagcaa agtgggaatc tggagaatcg agtgcctgat cggcgaacac  3420
ctgcaggccg ggatgagcac caccttcctg gtgtactcta agaaatgtca gaccccactg  3480
gggatggcct ccggacatat ccgcgacttc cagatcaccg ctagcggaca gtacggacag  3540
tgggctccaa agctggctag actgcactat tctggctcca tcaacgcctg gtctaccaaa  3600
gagccattct cctggatcaa ggtggacctg ctggcccca tgatcatcca cggaatcaaa  3660
acccagggcg ctaggcagaa gttcagctct ctgtacatct cccagtttat catcatgtat  3720
agcctggacg ggaagaaatg gcagacctac agaggcaatt ccaccgggac cctgatggtc  3780
ttctttggaa acgtggattc cagcggcatc aagcacaaca tcttcaatcc acccatcatc  3840
gcccgctaca tccggctgca tcctacccac tatagcatca ggtctaccct gagaatggag  3900
ctgatgggat gcgacctgaa cagctgttct atgccactgg gcatggagtc caaggctatc  3960
agcgatgccc agatcaccgc ttcttcctac ttcaccaata tgtttgctac ctggtcccca  4020
agcaaggcta gactgcacct gcagggaaga tccaacgctt ggagacccca ggtgaacaat  4080
cctaaggagt ggctgcaggt cgacttccag aaaaccatga aggtcaccgg ggtgaccacc  4140
cagggagtga aatctctgct gacctccatg tacgtcaagg agttcctgat cagctcttcc  4200
caggacggcc accagtggac cctgttcttt cagaacggca aggtcaaagt gttccagggg  4260
aatcaggact cttttacccc cgtcgtgaac tccctggatc ctccactgct gaccaggtac  4320
ctgagaatcc atcctcagag ctgggtgcac cagatcgctc tgagaatgga ggtcctggga  4380
tgcgaagctc aggacctgta ttga                                           4404
```

SEQ ID NO: 10        moltype = DNA   length = 4403
FEATURE              Location/Qualifiers
misc_feature        1..4403
                    note = synthetic lcoET3 CpGs removed
source              1..4403
                    mol_type = other DNA
                    organism = synthetic construct
SEQUENCE: 10

```
atgcagctgg aactgtctac ctgtgtgttt ctgtgtctgc tgcctctggg gttttctgct  60
atcaggagat actatctggg agctgtggag ctgtcctggg actacaggca gtctgagctg  120
ctgagagaac tgcatgtgga taccagattc ccagctacag ctccaggagc tctgcctctg  180
ggcccatctg tgctgtacaa gaaaacagtc tttgtggagt ttacagacca gctgttctct  240
gtggccaggc caagaccacc ttggatggga ctgctgggac caaccatcca ggctgaggtg  300
tatgatacag tggtggtgac cctgaaaaac atggcctccc atcctgtgag cctgcatgct  360
gtggggggtgt ccttctggaa gtcctctgag ggagctgagt atgaagacca tacctcccag  420
agggagaaag aagatgataa ggtgctgcct ggcaaaagcc agacctatgt ctggcaggtg  480
ctgaaggaga atggaccaac tgcttctgac ccaccatgcc tgacctactc ttatctgtct  540
catgtggatc tggtgaagga cctgaattct ggactgattg gagctctgct ggtgtgtaga  600
gagggaagcc tgaccagaga aagaacccag aacctgcatg agtttgtcct gctgtttgct  660
gtgtttgatg aagggaagag ctggcactct gccaggaatg actcctggac cagagctatg  720
gatccagctc ctgctagagc tcagcctgct atgcacacag tcaatggcta tgtgaataagg  780
tctctgccag gactgattgg ctgccataag aaatctgtct attggcatgt gattggaatg  840
ggcaccagcc ctgaggtgca ttctatcttc ctggaaggcc acacctttct ggtcaggcac  900
catagacagg cctctctgga gatctcccct ctgaccttcc tgcacagctca gacctttctg  960
atggccctgg ggcagttcct gctgttttgc catatctctt cccaccatca tggaggaatg  1020
gaggctcatg tcagggtgga atcctgtgct gaggaaccac agctgagaag aaaggctgat  1080
gaggaagagg actatgatga taacctgtat gactctgata tggatgtggt gaggctggat  1140
ggggatgatg tcagcccttt catccagatc aggtctgtgg ccaagaaaca tccaaagacc  1200
tgggtccact acattgctgc tgaagaggaa gattgggact atgcccccct ggtgctgtct  1260
cctgatgata gatcctacaa aagccagtat ctgaacaatg ggccccagag gattggaagg  1320
aagtacaaga aagtgaggtt catggcctat acagatgaga cctttaagac cagagaggct  1380
atccagcatg aatctgggat cctgggacct ctgctgtatg gagaagtggg ggatacctgc  1440
tgatcatctt caagaaccag gcctccaggc catacaatat ctatccccat ggcatcacag  1500
atgtgagacc actgtacagc aggagactgc ccaaggggt caaacacctg aaggatttcc  1560
ccatcctgcc tggagagatc tttaagtata aatggacagt cacagtggaa gatgggccta  1620
ccaagtctga tccaaggtgc ctgaccagat actatagctc ttttgtgaac atggagagag  1680
acctggcttc tggactgatt ggaccacctgc tgatctgtta caaagagtct gtggaccaga  1740
ggggcaacca gatcatgtct gataagagaa atgtcatcct gttctctgtg tttgatgaga  1800
acaggagctg gtacctgaca gagaacatcc agaggttcct gccaaatcca gctggagtgc  1860
agctggagga cccagaattt caggcttcca acatcatgca tagcatcaat ggctatgtgt  1920
ttgatagcct gcagctgtct gtctgcctgc atgaggtggc ctactggtat atcctgtcca  1980
ttggagctca gacagacttc ctgtctgtgt tctttagtgg gtacaccttt aagcataaaa  2040
tggtgtatga ggataccctg accctgttcc cctttttctgg ggagacagtg ttcatgtcca  2100
tggaaaaccc tggcctgtgg atcctggggt gccacaactc tgacttcagg aatagaggaa  2160
tgacagccct gctgaaagtg tccagctgtg ataagaatac aggggattac tatgaggact  2220
cttatgaaga tatctgtgct tatctgctga gcaagaacaa tgccattgag cccaggtctt  2280
ttgctcagaa ctccagacct ccatctgctt ctgctcctaa gccacctgtg ctgagaagac  2340
atcagaggga catctcccctg cctaccttcc agccagagga agatataaatg gactatgatg  2400
atatcttcag cacagagacc aaggggggaag attttgacat ctatggagag gatgaaaacc  2460
aggatccaag atccttccag aagagaacca gacactactt tattgctgct gtggagcagc  2520
tgtgggacta tgggatgtct gaaagcccaa gggccctgag aacacagagct cagaatggag  2580
aggtgcccag attcaagaaa gtggtgttca gagagtttgc tgatgccgagc tttacccagc  2640
catcttacag gggggagctg aacaagcatc tgggctgct gggaccctat atcagagctg  2700
aggtggaaga taacatcatg gtgaccttca agaatcaggc ttctaggccc tactcctttt  2760
attcttccct gatctcctac cctgatgatc aggagcaggg agctgaacct aggcacaact  2820
ttgtgcagcc aaatgagacc agaacctact tttggaaggt gcagcatcac atggctccca  2880
cagaggatga atttgactgc aaaagcttgg gcctatttttc tgatgtggac ctggagaagg  2940
```

```
atgtgcattc tggcctgatt gggcctctgc tgatctgtag ggccaacacc ctgaatgctg   3000
ctcatggaag acaggtcaca gtgcaggagt ttgctctgtt ctttaccatc tttgatgaaa   3060
ccaagagctg gtacttcaca gagaatgtgg aaaggaattg cagagccccc tgtcatctgc   3120
agatggagga ccctaccctg aaggaaaact acaggttcca tgccatcaat ggatatgtca   3180
tggataccct gcctggcctg gtcatggctc agaaccagag gatcagatgg tacctgctgt   3240
ctatgggatc caatgagaat atccatagca tccacttctc tggccatgtc tttttctgtga  3300
ggaagaaaga ggaatacaaa atggctgtgt acaatctgta tcctggggtc tttgagacag   3360
tggaaatgct gccaagcaaa gtgggaatct ggagaattga gtgcctgatt ggggaacacc   3420
tgcaggctgg gatgagcacc accttcctgg tgtactctaa gaaatgtcag accccactgg   3480
ggatggcctc tggacatatc agggacttcc agatcacagc ttctggacag tatggacagt   3540
gggctccaaa gctggctaga ctgcactatt ctggctccat caatgcctgg tctaccaaag   3600
agccattctc ctggatcaag gtggacctgc tggcccccat gatcatccat ggaatcaaaa   3660
cccagggagc taggcagaag ttcagctctc tgtacatctc ccagtttatc atcatgtata   3720
gcctggatgg gaagaaatgg cagacctaca gaggcaattc cactgggacc ctgatggtct   3780
tctttggaaa tgtggattcc tctggcatca agcacaacat cttcaatcca cccatcattg   3840
ccaggtacat caggctgcat cctacccact atagcatcag gtctaccctg agaatggagc   3900
tgatgggatg tgacctgaac agctgttcta tgccactggg catggagtcc aaggctatct   3960
ctgatgccca gatcacagct tcttcctact tcaccaatat gtttgctacc tggtccccaa   4020
gcaaggctag actgcacctg cagggaagat ccaatgcttg gagaccccag gtgaacaatc   4080
ctaaggagtg gctgcaggtg gacttccaga aaaccatgaa ggtcacaggg gtgaccaccc   4140
agggagtgaa atctctgctg acctccatgt atgtcaagga gttcctgatc agctcttccc   4200
aggatgccca ccagtggacc ctgttctttc agaatggcaa ggcaaagtg ttccagggga    4260
atcaggactc ttttacccca gtggtgaact ccctggatcc tccactgctg accaggtacc   4320
tgagaatcca tcctcagagc tgggtgcacc agattgctct gagaatggag gtcctgggat   4380
gtgaagctca ggacctgtat tga                                           4403
```

SEQ ID NO: 11          moltype = DNA   length = 4404
FEATURE                Location/Qualifiers
misc_feature           1..4404
                       note = synthetic NoCoET3
source                 1..4404
                       mol_type = other DNA
                       organism = synthetic construct
SEQUENCE: 11

```
atgcagctag agctctccac ctgtgtcttt ctgtgtctct tgccactcgg ctttagtgcc   60
atcaggagat actacctggg cgcagtggaa ctgtcctggg actaccggca aagtgaactc   120
ctccgtgagc tgcacgtgga caccagattt cctgctacag cgccaggagc tcttccgttg   180
ggcccgtcag tcctgtacaa aaagactgtg ttcgtagagt tcacggatca acttttcagc   240
gttgccaggc ccaggccacc atggatgggt ctgctgggtc ctaccatcca ggctgaggtt   300
tacgacacgg tggtcgttac cctgaagaac atggcttctc atcccgttag tcttcacgct   360
gtcggcgtct ccttctggaa atcttccgaa ggcgctgaat atgaggatca caccagccaa   420
agggagaagg aagacgataa agtccttccc ggtaaaagcc aaacctacgt ctggcaggtc   480
ctgaaagaaa atggtccaac agcctctgac ccaccatgtc ttacctactc ataccgtctt   540
cacgtggacc tggtgaaaga cctgaattcg ggcctcattg gagccctgct ggtttgtaga   600
gaagggagtc tgaccagaga aaggacccag aacctgcacg aatttgtact acttttttgct   660
gtctttgatg aaggggaaag ttggcactca gcaagaaatg actcctggac acgggccatg   720
gatcccgcac ctgccagggc ccagcctgca atgcacacag tcaatggcta tgtcaacagg   780
tctctgccag gtctgatcgg atgtcataag aaatcagtct actggcacgt gattggaatg   840
ggcaccagcc cggaagtgca ctccattttt cttgaaggcc acacgtttct cgtgaggcac   900
catcgccagg cttccttgga gatctcgcca ctaactttcc tcactgctca gacattcctg   960
atggaccttg gccagttcct actgttttgt catatctctt cccaccacca tggtggcatg   1020
gaggctcacg tcagagtaga aagctgcgcg gaggagcccc agctgcggag gaaagctgat   1080
gaagaggaag attatgatga caatttgtac gactcggaca tggacgtggt ccggctcgat   1140
ggtgacgacg tgtctccctt tatccaaatc cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac gcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atccgcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatct tgtttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctgag gagaaactgt cttccatgtcg  2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga acctaggagc   2280
tttgcccaga attcaagacc ccctagtgcg agcgctccaa agcctccggt cctgcgacgg   2340
catcagaggg acataagcct tcctactttt cagccgaggg aagacaaaat ggactatgat   2400
gatatcttct caactgaaac gaagggagaa gattttgaca tttacggtga ggatgaaaat   2460
caggaccctc gcagctttca gaagagaacc cgacactatt tcattgctgc ggtggagcag   2520
ctctgggatt acgggatgag cgaatccccc cgggcgctaa gaaacagggc tcagaacgga   2580
gaggtgcctc ggttcaagaa ggtggtcttc cgggaatttg ctgacggctc cttcacgcag   2640
ccgtcgtacc gcgggggaact caacaaacac ttggggctct tgggaccta catcagagcg   2700
```

-continued

```
gaagttgaag acaacatcat ggtaactttc aaaaaccagg cgtctcgtcc ctattccttc   2760
tactcgagcc ttatttctta tccggatgat caggagcaag gggcagaacc tcgacacaac   2820
ttcgtccagc caaatgaaac cagaacttac ttttggaaag tgcagcatca catggcaccc   2880
acagaagacg agtttgactg caaagcctgg gcctactttt ctgatgttga cctggaaaaa   2940
gatgtgcact caggcttgat cggccccctt ctgatctgcc gcgccaacac cctgaacgct   3000
gctcacggta gacaagtgac cgtgcaagaa tttgctctgt ttttcactat ttttgatgag   3060
acaaagagct ggtacttcac tgaaaatgtg gaaaggaact gccgggcccc ctgccatctg   3120
cagatggagg accccactct gaaagaaaac tatcgcttcc atgcaatcaa tggctatgtg   3180
atggatacac tccctggctt agtaatggct cagaatcaaa ggatccgatg gtatctgctc   3240
agcatgggca gcaatgaaaa tatccattcg attcattta gcggacacgt gttcagtgta   3300
cggaaaaagg aggagtataa aatggccgtg tacaatctct atccgggtgt ctttgagaca   3360
gtggaaatgc taccgtccaa agttggaatt tggcgaatag aatgcctgat tggcgagcac   3420
ctgcaagctg ggatgagcac gactttcctg gtgtacagca agaagtgtca gactcccctg   3480
ggaatggctt ctggacacat tagagatttt cagattacga cttcaggaca atatggacag   3540
tgggccccaa agctgccag acttcattat tccggatcaa tcaatgcctg gagcaccaag   3600
gagccctttt cttggatcaa ggtggatctg ttggcaccaa tgattattca cggcatcaag   3660
acccagggtg cccgtcagaa gttctccagc ctctacatct ctcagtttat catcatgtat   3720
agtcttgatg ggaagaagtg gcagacttat cgaggaaatt ccactggaac cttaatggtc   3780
ttctttggca atgtggattc atctgggata aaacacaata ttttaaccc tccaattatt   3840
gctcgataca tccgtttgca cccaactcat tatagcattc gcagcactct tcgcatggag   3900
ttgatgggct gtgatttaaa tagttgcagc atgccattgg gaatggagag taaagcaata   3960
tcagatgcac agattactgc ttcatcctac tttaccaata tgtttgccac ctggtctcct   4020
tcaaaagctc gacttcacct ccaagggagg agtaatgcct ggagacctca ggtgaataat   4080
ccaaaagagt ggctgcaagt ggacttccag aagacaatga aagtcacagg agtaactact   4140
cagggagtaa aatctctgct taccagcatg tatgtgaagg agttcctcat ctccagcagt   4200
caagatggcc atcagtggac tctcttttt cagaatggca agtaaaggt ttttcaggga   4260
aatcaagact ccttcacacc tgtggtgaac tctctagacc caccgttact gactcgctac   4320
cttcgaattc acccccagag ttgggtgcac cagattgccc tgaggatgga ggttctgggc   4380
tgcgaggcac aggacctcta ctga                                           4404
```

```
SEQ ID NO: 12          moltype = DNA   length = 4404
FEATURE                Location/Qualifiers
misc_feature           1..4404
                       note = synthetic mcoET3
source                 1..4404
                       mol_type = other DNA
                       organism = synthetic construct
SEQUENCE: 12
atgcagctgg agctctcaac ctgtgtgttc ctctgcctgc tcccctggg attttcagct   60
atcaggagat actatctggg agcagtggaa ctgtcctggg actacaggca gtcagagctg   120
ctcagagaac tgcatgtgga tactaggttc cctgcaacag ctcctggagc actgccactg   180
ggaccttcag tgctgtacaa gaaaactgtc tttgtggagt ttacagacca gctgttcagt   240
gtggccaggc ccaggccccc ctggatgggg ctgctgggac caccatcca ggctgaagtg   300
tatgatactg tggtggtgac cctgaaaaac atggcctctc atccagtcag cctgcatgct   360
gtgggagtga gcttctggaa gagcagtgag ggagctgagt atgaagacca tacctcacag   420
agggagaaag aagatgataa ggtgctgcca ggaaaaagcc agacctatgt gtggcaggtg   480
ctgaaggaga tggccctac agcttcagat cctccctgcc tacatactc ttatctgagc   540
catgtggatc tggtgaagga cctcaatagt ggcctgattg gggcactgct ggtgtgcaga   600
gagggggtccc tcacaaggga aagaactcag aacctgcatg agtttgtcct gctctttgct   660
gtgtttgatg agggaaagtc ctggcactca gcaaggaatg acagctggac cagggctatg   720
gacccagcac cagccagagc tcagccagct atgcacactg tcaatggcta tgtgaatcag   780
tccctgcctg gactcattgg ctgccataag aaatcagtct attggcatgt gattggaatg   840
ggcaccagcc cagaggtgca ttccatcttc ctggaaggcc acacatttct ggtcaggcac   900
catagacagg ccagcctgga gatcagccca ctgactttc tcacagcaca gacatttctg   960
atggacctgg ggcagttcct gctctttgc catatctcaa gtcaccatca tggagggatg   1020
gaggctcatg tcaggggtgga aagctgtgca gaggaacctc agctgaggag gaaggcagat   1080
gaggaagagg actatgatga taacctgtat gactcagata tggatgtggt gaggctggat   1140
ggagatgatg tcagcccatt catccagatc aggtcagtgg ctaagaaaca ccctaagacc   1200
tgggtccact acattgcagc tgaagaggaa gattgggact atgcacccct ggtgctggcc   1260
ccagatgata gaagttacaa atctcagtat ctgaacaatg ggccccagag gattggaagg   1320
aagtacaaga aagtgaggtt catggcttat actgatgaga cctttaagac aagagaggca   1380
atccagcatg aaagtggcat cctgggacca ctgctctatg gagaagtggg ggataccctg   1440
ctcatcatct tcaagaacca ggcctcaagg ccttacaata tctatcccca tggcatcaca   1500
gatgtgaggc ctctctacag caggagactg cccaaggag tcaaacacct caaggatttc   1560
cccatcctgc cagggaaat cttcaagtat aaatggacag tcactgtgga agatgggcca   1620
actaagtcag atcctaggtg cctgaccagg tactattcta gctttgtgaa catggagagg   1680
gacctggctt caggactgat tggacctctg ctcatctgct acaaagaatc agtggaccag   1740
aggggcaacc agatcatgag tgataagaga aatgtcatcc tgttctcagt gtttgatgag   1800
aataggagtt ggtatctgac agaaaacatc cagaggttcc tgcctaatcc tgcaggagtg   1860
cagctggagg acccagaatt tcaggcttca aacatcatgc atagtatcaa tggctatgtg   1920
tttgatagtc tgcagctctc tgtctgcctg catgaggtgg cctactgta tatcctcagc   1980
attggagctc agactgactt cctgagtgtg ttctttttcag ctacacatt caagcataag   2040
atggtctatg aagatccct gacactcttc cccttttctg gggagactgt gtttatgagc   2100
atggaaaacc caggcctgtg gattctgggg tgccacaaca gtgacttcag gaatagaggg   2160
atgactgctc tgctcaaagt gtcctcatgt gataagaata ctggagatta ctatgaggac   2220
tcttatgaag atatcagtgc atatctgctc tccaaaaaca atgccattga gcccaggtca   2280
tttgctcaga acagtagacc accttctgca agtgcaccaa agcctccagt gctgaggaga   2340
caccagaggg acatcagcct gccaacctcc agcctgagg aagataaaat ggactatgat   2400
gatatcttct ccactgagac caaggggga gattttgaca tctatggaga ggatgaaaac   2460
```

```
caggacccca ggtccttcca gaagaggacc agacactact ttattgcagc tgtgggagcag   2520
ctgtgggact atggcatgtc tgaatcacct agagctctga ggaacagagc acagaatggg   2580
gaggtgccca ggttcaagaa agtggtgttc agagaatttg cagatggctc ttttacccag   2640
cctagctaca gggggggagct caacaagcat ctggggctgc tgggacccta tatcagagca   2700
gaggtggaag ataacatcat ggtgacattc aagaatcagg cctcaagacc ctacagtttt   2760
tatagttctc tgatcagcta cccagatgat caggagcagg gggctgaacc aaggcacaac   2820
tttgtgcagc ctaatgagac aagaacttac ttttggaagg tccagcatca catggctccc   2880
acagaggatg agtttgactg caaggcctgg gcatattttt ctgatgtgga cctggagaag   2940
gatgtgcata gtggcctcat tgggccactg ctcatctgca gggcaaacac actgaatgct   3000
gcacatggca ggcaggtcac tgtgcaggag tttgccctgt tctttacaat ctttgatgaa   3060
actaagtcct ggtacttcac agagaatgtg gaaaggaatt gcagagcccc ctgccatctc   3120
cagatggagg acccaactct gaaggaaaac tacaggttcc atgctatcaa tggatatgtc   3180
atggatacac tgccaggcct ggtgatggca cagaaccaga ggatcaggtg gtatctgctc   3240
agcatggggt ccaatgagaa tatccattct atccacttct caggacatgt cttttcagtg   3300
aggaagaaag aggaatataa aatggctgtg tacaatctgt atccaggggt ctttgagaca   3360
gtggaaatgc tgcctagcaa agtggggatc tggagaattg agtgcctcat tggagaacac   3420
ctgcaggcag ggatgtccac cacatttctg gtgtactcaa agaaatgcca gactcccctg   3480
gggatggcaa gtggacatat cagggacttc cagatcactg catcaggaca gtatggacag   3540
tgggcaccaa agctggctag gctccactat agtggctcta tcaatgcttg gagtaccaaa   3600
gagcctttct cttggatcaa ggtggatctg ctggcccca tgatcatcca tggaatcaaa   3660
acacaggagg ctagacagaa gttcagctcc ctgtacatca gtcagtttat catcatgtat   3720
tctctggatg ggaagaaatg gcagacctac aggggcaata gcatggagac actgatggtc   3780
ttctttggaa atgtggattc aagtggcatc aagcacaaca tcttcaatcc tccatcatt   3840
gccaggtaca tcagactgca tcccacacac tattcaatca ggagtactct cagaatggag   3900
ctgatggggt gtgacctcaa cagctgctcc atgccactgg aatggaatc caaggcaatc   3960
tcagatgccc agatcactgc ttctagctac ttcaccaata tgtttgcaac atggtcaccc   4020
agtaaagcaa ggctgcacct ccagggaagg tccaatgctt ggagacccca ggtgaacaat   4080
ccaaaggagt ggctgcaggt ggactttcag aaaaaccatga aggtcacagg ggtgactacc   4140
cagggagtga aaagtctgct cacctctatg tatgtcaagg agttcctgat ctcctcaagt   4200
caggatggcc accagtggac actgttcttt cagaatggca aggtcaaagt gttccagggg   4260
aatcaggaca gctttacacc agtggtgaac agcctggacc ccctctgct cactagatat   4320
ctgagaatcc atccacagag ctgggtgcac cagattgcac tcagaatgga ggtcctgggc   4380
tgtgaagccc aggacctgta ttga   4404

SEQ ID NO: 13       moltype = DNA   length = 4374
FEATURE             Location/Qualifiers
misc_feature        1..4374
                    note = synthetic lcoHSQ with CpGs
source              1..4374
                    mol_type = other DNA
                    organism = synthetic construct
SEQUENCE: 13
atgcagatcg aactgtctac ctgtttcttt ctgtgcctgc tgcggtttttg tttttccgct   60
accagaagat actacctggg agccgtcgaa ctgagctggg attacatgca gtctgacctg   120
ggagagctgc ccgtggacgc tagattccca cctagagtcc ctaagtcctt ccccttcaac   180
accagcgtgg tctacaagaa aaccctgttc gtggagttta ccgaccacct gttcaacatc   240
gctaagccta gaccaccatg gatgggactg ctgggaccaa ctccaggc cgaggtgtac   300
gacaccgtgg tcatcaccct gaaaaacatg gcttctcacc ccgtgtccct gcatgctgtg   360
ggcgtctcct actggaaggc cagcgaaggg gctgagtatg acgatcagac cagccagcgg   420
gaaaaagagg acgataaggt gttccctggc gggtcccata cctacgtgtg gcaggtcctg   480
aaggaaatg gaccaatggc ttccgaccct ctgtgcctga cctactctta tctgtcccac   540
gtggacctgg tcaaggatct gaacagcggc ctgatcgggg ctctgctggt gtgtcgcgag   600
gggtccctgg ccaaggagaa aacccagacc ctgcataagt tcatcctgct gttcgccgtg   660
tttgacgaag gaaaaagctg gcactctgag accaagaact ctctgatgca ggacagggat   720
gccgcttccg ccagagcttg gcccaagatg cacaccgtga acggctacgt caataggagc   780
ctgcctggac tgatcggctg ccacagaaag tccgtgtatt ggcatgtcat cggaatgggc   840
accacccctg aagtgcacag catcttcctg gaggggcata ccttttctggt ccgcaaccac   900
cggcaggcta gcctggagat ctctccaatc accttcctga ccgcccagac cctgctgatg   960
gacctgggac agttcctgct gtttttgccac atctccagcc accagcatga tggcatggag   1020
gcttacgtga agtcgactc ctgtcccgag gaacctcagc tgaggatgaa gaacaatgag   1080
gaagccgaag actatgacga tgacctgacc gacagcgaga tggatgtggt ccgcttcgat   1140
gacgataact ctccctcctt tatccagatc cggtccgtgg ccaagaaaca ccctaagacc   1200
tgggtccatt acatcgccgc tgaggaagag gactgggatt atgctccact ggtgctggcc   1260
cccgacgata gatcctacaa aagccagtat ctgaacaatg gaccccagag gatcggcaga   1320
aagtacaaga aagtgaggtt catggcttat accgatgaga cctttaagac cagagaagcc   1380
atccagcacg agtccgggat cctgggacct ctgctgtacg gcgaagtggg ggacaccctg   1440
ctgatcatct tcaagaacca ggccagcagg ccttacaata tctatccaca tggcatcacc   1500
gatgtgagac ctctgtactc ccgccggctg ccaaagggcg tgaaacacct gaaggacttc   1560
ccaatcctgc ccgggggaat ctttaagtat aaatggaccg tcacccgtga ggatgggccc   1620
accaagagcg accctaggtg cctgaccaga tactattctt ccttcgtgaa tatggagaga   1680
gacctggctt ccggactgat cggacccctg ctgatctgtt acaaagagag cgtggatcag   1740
cgcggcaacc agatcatgtc tgacaagcgg aatgtgatcc tgttcagcgt ctttgacgaa   1800
aaccgctctt ggtacctgac cgagaacatc cagcggttcc tgcctaatcc agctggagtg   1860
cagctggaag atcccgagtt ccaggcctct aacatcatca attccatcaa tggctacgtg   1920
ttcgactccc tgcagctgag cgtgtgcctg cacgaggtcg cttactggta tatcctgagc   1980
atcggagccc agaccgattt cctgtctgtg ttctttttccg gctacacctt taagcataaa   2040
atggtgtatg aggacaccct gaccctgttcc ccattttccg gcgaaaccgt gttcatgagc   2100
atggagaatc ccgggctgtg gatcctggga tgccacaact ccgatttcag gaatagaggg   2160
atgaccgccc tgctgaaagt gagctcttgt gacaagaaca ccgagacta ctatgaagat   2220
```

-continued

```
agctacgagg acatctctgc ttatctgctg tccaaaaaca atgccatcga gcccaggagc   2280
ttctctcaga accctccagt gctgaagcgc caccagcggg agatcaccag aaccaccctg   2340
cagagcgatc aggaagagat cgactacgac gataccatct ccgtggaaat gaagaaagag   2400
gacttcgata tctatgacga agatgagaac cagtctccca ggtccttcca gaagaaaacc   2460
agacattact ttatcgccgc tgtggagcgg ctgtgggagt atggcatgtc cagctctcct   2520
cacgtgctga aaatagagc tcagtccgga agcgtcccac agttcaagaa agtggtcttc   2580
caggagttta ccgacggaag cttttacccag ccactgtacc gcggcgaact gaacgagcac   2640
ctgggggctgc tgggacccta tatccgggct gaagtggagg ataacatcat ggtcaccttc   2700
aggaatcagg ccagcagacc ctactctttt tattccagc tgatctccta cgaagaggac   2760
cagagacagg gagctgaacc aagaaaaaac ttcgtgaagc ctaatgagac caaaacctac   2820
ttttggaagg tgcagcacca tatggcccct accaaagacg agttcgattg caaggcctgg   2880
gcttatttta gcgacgtgga tctggagaag gacgtccact ccggcctgat cgggccactg   2940
ctggtgtgtc ataccaacac cctgaatcca gctcacggaa ggcaggtgac cgtccaggaa   3000
ttcgccctgt tctttaccat ctttgatgag accaagagct ggtacttcac cgaaaactg   3060
gagaggaatt gcagagcccc atgtaacatc cagatggaag accccacctt caaggagaac   3120
tacagatttc atgctatcaa tgggtatatc atggataccc tgccaggact ggtcatggct   3180
caggaccaga ggatcagatg gtacctgctg agcatggggg ctaacgagaa tatccactcc   3240
atccatttca gcggacacgt gtttaccgtc cgcaagaaag aagagtacaa aggtgccctg   3300
tacaacctgt atcccggcgt gttcgaaacc gtcgagatgc tgccttccaa ggctgggatc   3360
tggcgggtgg aatgcctgat cggggagcac ctgcatgccg gaatgtctac cctgttcctg   3420
gtgtactcca ataagtgtca gacccccctg gggatggcta gcggacatat ccgcgacttc   3480
cagatcaccg cttccggaca gtacggacag tgggctccta agctggctag actgcactat   3540
tctggctcca tcaacgcttg gtctaccaaa gagcctttct cctggatcaa ggtggacctg   3600
ctggctccaa tgatcatcca tggcatcaaa acccaggggg ccaggcagaa gttctcttcc   3660
ctgtacatca gccagtttat catcatgtat tctctggatg ggaagaaatg gcagacctac   3720
agaggcaatt ccaccgggac cctgatggtg ttctttggcga acgtcgacag ctctgggatc   3780
aagcacaaca tcttcaatcc ccctatcatc gcccgctaca tccggctgca cccaacccat   3840
tattccatcc gcagcaccct gcggatggag ctgatggggt gcgatctgaa cagctgttct   3900
atgcccctgg gaatggagtc taaggccatc tccgacgctc agatcaccgc ctccagctac   3960
ttcaccaata tgtttgctac ctggtcccca agcaaggcca gactgcatct gcagggaaga   4020
agcaacgctt ggagaccaca ggtgaacaat cccaaggagt ggctgcaggt cgacttccag   4080
aaaaccatga aggtgaccgg agtcaccacc cagggcgtga aaagcctgct gacctctatg   4140
tacgtcaagg agttcctgat ctcttccagc caggacgggc accagtggac cctgttcttt   4200
cagaacggaa aggtgaaagt cttccagggc aatcaggatt cctttacccc tgtggtcaac   4260
agcctggacc caccctgct gaccaggtac ctgagaatcc acccacagtc ctgggtgcat   4320
cagatcgctc tgaggatgga agtcctgggc tgcgaggccc aggacctgta ttga   4374
```

SEQ ID NO: 14                moltype = DNA   length = 4374
FEATURE                     Location/Qualifiers
misc_feature                1..4374
                            note = synthetic lcoHSQ CpGs removed
source                      1..4374
                            mol_type = other DNA
                            organism = synthetic construct
SEQUENCE: 14

```
atgcagattg aactgtctac ctgtttcttt ctgtgcctgc tgaggttttg tttttctgct     60
accagaagat actacctggg agctgtggaa ctgagctggg attacatgca gtctgacctg    120
ggagagctgc ctgtggatgc tagattccca cctagagtcc ctaagtcctt cccccttcaac    180
acctctgtgg tctacaagaa aaccctgttt gtggagttta cagaccacct gttcaacatt    240
gctaagccta gaccaccatg gatgggactg ctgggaccaa ccatccaggc agaggtgtat    300
gacacagtgg tcatcaccct gaaaaacatg gcttctcacc ctgtgtccct gcatgctgtg    360
ggagtctcct actggaaggc ctctgaaggg gctgagtatg atgatcagac cagccagagg    420
gaaaaagagg atgataaggt gttccctgga gggtcccata cctatgtgtg gcaggtcctg    480
aaggagaatg gaccaatggc ttctgaccct ctgtgcctga cctactctta tctgtcccat    540
gtggacctgg tcaaggatct gaactctggc ctgattgggg ctctgctggt gtgtagggaa    600
gggtccctgg ccaaggagaa aacccagacc ctgcataagt tcatcctgcc gtttgctgtg    660
tttgatgaag aaaaagctg gcactctgag accaagaact ctctgatgca ggacagggat    720
gctgcttctg ccagagcttg gcccaagatg cacacagtga atggctatgt caataggagc    780
ctgcctggac tgattggctg ccacagaaag tctgtgtatt ggcatgtcat tggaatgggc    840
accaccaccg aagtgcacag catcttcctg gagggggcata ccttttctggt caggaaccac    900
aggcaggcta gctgagat ctctccaatc accttcctga cagcccagac cctgctgatg    960
gacctgggac agttcctgct gttttgccac atctccagcc accagcatga tggcatggag   1020
gcttatgtga aagtggactc ctgtcctgag gaacctcagc tgaggatgaa gaacaatgag   1080
gaagctgaag actatgatga tgacctgaca gactctggt gatgtggt caggtttgat   1140
gatgataact ctccctcctt tatccagatc aggtctgtgg ccaagaaaca ccctaagacc   1200
tgggtccatt acattgctgc tgaggaagag gactgggatt atgctccact ggtgctggcc   1260
cctgatgata gatcctacaa aagccagtat ctgaacaatg accccagag gattggcaga   1320
aagtacaaga aagtgaggtt catggctat acagatgaga cctttaagac cagagaagcc   1380
atccagcatg agtctgggat cctgggacct ctgctgtatg gggaagtggg ggacaccctg   1440
ctgatcatct tcaagaacca ggccagcagg ccttacaata tctatccaca tggcatcaca   1500
gatgtgagac ctctgtactc caggaggctg ccaaaggggg tgaaacacct gaaggacttc   1560
ccaatcctgc ctgggaaat ctttaagtat aaatggacag tcacagtgga ggatgggccc   1620
accaagtctg accctaggtg cctgaccaga tactattctt cctttgtgaa tatggagaga   1680
gacctggctc ctggactgat tggaccctg ctgatctgtt acaaagagtc tgtggatcag   1740
aggggcaacc agatcatgtc tgacaagagg aatgtgatcc tgttctctgt ctttgatgaa   1800
aacaggtctt ggtacctgac agagaacatc cagaggttcc tgcctaatcc agctggagtg   1860
cagctggaag atcctgagtt ccaggcctct aacatcatgc attccatcaa tggctatgtg   1920
tttgactccc tgcagctgtc tgtgtgcctg catgaggtgg cttactggta tatcctgagc   1980
attggagccc agacagattt cctgtctgtg ttctttttctg gctacacctt taagcataaa   2040
```

```
atggtgtatg aggacaccct gaccctgttc ccattttctg gagaaactgt gttcatgagc  2100
atggagaatc ctgggctgtg gatcctggga tgccacaact ctgatttcag gaatagaggg  2160
atgacagccc tgctgaaagt gagctcttgt gacaagaaca caggagacta ctatgaagat  2220
agctatgagg acatctctgc ttatctgctg tccaaaaaca atgccattga gcccaggagc  2280
ttctctcaga accctccagt gctgaagagg caccagaggg agatcaccag aaccaccctg  2340
cagtctgatc aggaagagat tgactatgat gataccatct ctgtggaaat gaagaaaag  2400
gactttgata tctatgatga agatgagaac cagtctccca ggtccttcca gaagaaaacc  2460
agacattact ttattgctgc tgtgggagagg ctgtgggact atggcatgtc cagctctcct  2520
catgtgctga gaaatagagc tcagtctgga tctgtcccac agttcaagaa agtggtcttc  2580
caggagttta cagatggaag ctttaccag ccactgtaca ggggagaact gaatgagcac  2640
ctggggctgc tgggacccta tatcagggct gaagtggagg ataacatcat ggtcaccttc  2700
aggaatcagg ccagcagacc ctactctttt tattccagcc tgatctccta tgaagaggac  2760
cagagacagg gagctgaacc aagaaaaaac tttgtgaagc ctaatgagac caaaacctac  2820
ttttggaagg tgcagcacca tatggcccct accaaagatg agttgattg caaggcctgg  2880
gcttattttt ctgatgtgga tctggagaag gatgtccact ctggcctgat tgggccactg  2940
ctggtgtgtc ataccaacac cctgaatcca gctcatggaa ggcaggtgac agtccaggaa  3000
tttgccctgt tctttaccat cttttgatgag accaagagct ggtacttcac agaaaacatg  3060
gagaggaatt gcagagcccc atgtaacatc cagatggaag accccacctt caaggagaac  3120
tacagatttc atgctatcaa tgggtatatc atggataccc tgccaggact ggtcatggct  3180
caggaccaga ggatcagatg gtacctgctg agcatggggt ctaatgagaa tatccactcc  3240
atccatttct ctggacatgt gtttacagta aggaagaaag aagagtacaa gatggccctg  3300
tacaacctgt atcctggggt gtttgaaaca gtggagatgc tgccttccaa ggctgggatc  3360
tggagggtgg aatgcctgat tggggagcac ctgcatgctg gaatgtctac cctgttcctg  3420
gtgtactcca ataagtgtca gaccccctg gggatggctt ctggacatat cagggacttc  3480
cagatcacac cttctggaca gtatggacag tgggctccta agctggctag actgcactat  3540
tctggctcca tcaatgcttg gtctaccaaa gagcctttct cctggatcaa ggtggacctg  3600
ctggctccaa tgatcatcca tggcatcaaa acccaggggg ccaggcagaa gttctcttcc  3660
ctgtacatca gccagtttat catcatgtat tctctggatg ggaagaaatg gcagacctac  3720
agaggcaatt ccacagggac cctgatggtg ttctttggca atgtggacag ctctgggatc  3780
aagcacaaca tcttcaatcc ccctatcatt gccaggtaca tcagactgca cccaacccat  3840
tattccatca ggagcaccct gagaatggag ctgatggggt gtgatctgaa cagctgttct  3900
atgcccctgg gaatggagtc taaggccatc tctgatgctc agatcacagc ctccagctac  3960
ttcaccaata tgtttgctac ctggtcccca agcaaggcta gactgcatct gcagggaaga  4020
agcaatgctt ggagaccaca ggtgaacaat cccaaggagt ggctgcaggt ggacttccag  4080
aaaaccatga aggtgacagg agtcaccacc cagggagtga aaagcctgct gacctctatg  4140
tatgtcaagg agttcctgat ctcttccagc caggatgggc accagtggac cctgttcttt  4200
cagaatggaa aggtgaaagt cttccagggc aatcaggatt cctttacccc tgtggtcaac  4260
agcctggacc caccctgct gaccaggtac ctgagaatcc ccccacagtc ctgggtgcat  4320
cagattgctc tgaggatgga agtcctgggc tgtgaggccc aggacctgta ttga        4374
```

SEQ ID NO: 15            moltype = DNA   length = 4374
FEATURE                  Location/Qualifiers
misc_feature            1..4374
                        note = synthetic NoCoHSQ
source                  1..4374
                        mol_type = other DNA
                        organism = synthetic construct
SEQUENCE: 15

```
atgcaaatag agctctccac ctgcttcttt ctgtgccttt tgcgattctg ctttagtgcc  60
accagaagat actacctggg tgcagtggaa ctgtcatggg actatatgca aagtgatctc  120
ggtgactgc ctgtggacgc aagatttcct cctagagtgc caaaatcttt tccattcaac  180
acctcagtcg tgtacaaaaa gactctgttt gtagaattca cggaccacct tttcaacatc  240
gctaagccaa ggccaccctg gatgggtctg ctaggtccta ccatccaggc tgaggtttat  300
gatacagtgg tcattacact taagaacatg gcttcccatc ctgtcagtct tcatgctgtt  360
ggtgtatcct actggaaagc ttctgaggga gctgaatatg atgatcagac cagtcaaagg  420
gagaaagaag atgataaagt cttccctggt ggaagccata catatgtctg gcaggtcctg  480
aaagagaatg gtccaatggc ctctgaccca ctgtgcctta cctactcata tctttctcat  540
gtggacctgt aaaagactt gaattcaggc ctcattggag ccctactagt atgtagagaa  600
gggagtctgg ccaaggaaaa gacacagacc ttgcacaaat ttatactact ttttgctgta  660
tttgatgaag ggaaaagttg gcactcagaa acaaagaact ccttgatgca ggatagggat  720
gctgcatctg ctcgggcctg gcctaaaatg cacacagtca atggttatgt aaacaggtct  780
ctgccaggtc tgattggatg ccacaggaaa tcagtctatt ggcatgtgat tggaatgggc  840
accactcctg aagtgcactc aatattcctc gaaggtcaca catttcttgt gaggaaccat  900
cgccaggcgt ccttggaaat ctcgccaata actttcctta ctttccaaac actcttgatg  960
gaccttggac agtttctact gttttgtcat atctcttccc accaacatga tggcatggaa  1020
gcttatgtca aagtagacag ctgtccagg gaacccaac tacgaatgaa aaataatgaa  1080
gaagcggaag actatgatga tgatcttact gattctgaaa tggatgtggt caggtttgat  1140
gatgacaact ctccttcctt tatccaaatt cgctcagttg ccaagaagca tcctaaaact  1200
tgggtacatt acattgctgc tgaagaggag gactggact atgctccctt agtcctcgcc  1260
cccgatgaca gaagttataa aagtcaatat ttgaacaatg ccctcagcg gattggtagg  1320
aagtacaaaa agtccgatt tatggcatac acagatgaaa cctttaagac gcgtgaagct  1380
attcagcatg aatcaggaat cttgggacct ttactttatg gggaagttgg agacacactg  1440
ttgattatat ttaagaatca agcaagcaga ccatataaca tctaccctca cggaatcact  1500
gatgtccgtc ctttgtattc aaggagatta caaaagtta taaaacattt gaaggattt  1560
ccaattctgc aggagaaat attcaaatat aaatggacag tgactgtaga agatgggcca  1620
actaaatcag atccgcggtg cctgaccgc tattactcta gtttcgttaa tatggagaga  1680
gatctagctt caggactcat tggccctctc ctcatctgct acaaagaatc tgtagatcaa  1740
agaggaaacc agataatgtc agacaagagg aatgtcatcc tgttttctgt atttgatgag  1800
aaccgaagct ggtacctcac agagaatata caacgctttc tccccaatcc agctggagtg  1860
```

-continued

```
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataacct caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga acctaggagc   2280
ttctctcaga atccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctggggtt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
tttttggaaag tgcaacatca tatggcaccc actaaagatg agtttgactg caaagcctgg   2880
gcttatttct ctgatgttga cctggaaaaa gatgtgcact caggcctgat tggaccccctt   2940
ctggtctgcc acactaacac actgaaccct gctcatggga gacaagtgac agtacaggaa   3000
tttgctctgt ttttcaccat cttttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac acttttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata ttttttaaccc tccaattatt gctcgataca tccgtttgca cccaactcat   3840
tatagcattc gcagcactct tcgcatcggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatgcc atcagtggac tctcttttt   4200
cagaatggca aagtaaaggt ttttcaggga aatcaagact ccttcacacc tgtggtgaac   4260
tctctagacc caccgttact gactcgctac cttcgaattc accccagag ttgggtgcac   4320
cagattgccc tgaggatgga ggttctgggc tgcgaggcac aggacctcta ctga           4374
```

SEQ ID NO: 16       moltype = DNA   length = 4375
FEATURE             Location/Qualifiers
misc_feature        1..4375
                    note = synthetic mcoHSQ
source              1..4375
                    mol_type = other DNA
                    organism = synthetic construct
SEQUENCE: 16

```
atgcagattg agctcagcac ctgcttcttt ctgtgcctgc tcaggttctg cttttcagcc   60
acaaggagat actatctggg agctgtggaa ctgtcatggg attacatgca gagtgacctg   120
ggagagctcc ctgtggatgc taggttcccc ccaagggtcc caaagtcttt cccttttaat   180
accagtgtgg tctataagaa aacactcttt gtggaattta ctgatcacct gttcaacatt   240
gcaaagccaa ggcctccctg gatgggactg ctgggaccta ccatccaggc tgaggtgtat   300
gacactgtgg tcatcacact gaaaaacatg gcatctcacc ctgtcagcct gcatgcagtg   360
ggagtcagct actggaaggc ttcagaaggg gcagagtatg atgatcagac aagccagaga   420
gaaaaagag atgataaggt gttcccagga gggagccata cttatgtgtg gcaggtcctg   480
aaggagaatg gcccaatggc cagtgaccca ctgtgcctca cctactcata tctgagtcat   540
gtggacctgg tcaaggatct caactcaggc ctgattgggg cactgctggt gtgcagggaa   600
ggctcactgg ccaaggagaa aacccagaca ctgcataagt tcatcctgct ctttgctgtg   660
tttgatgaag ggaaatcttg gcacagtgag accaagaaca gtctgatgca ggacagggat   720
gctgcttctg ccagagctttg gcccaagatg cacacagtga tggatatgt caataggtcc   780
ctgccaggac tcattggctg ccacagaaag tcagtgtatt ggcatgtcat tggaatgggc   840
accacaccag aagtgcacag catcttcctg gagggggata cctttctggt caggaaccac   900
aggcaggcca gcctggagat cagcccaatc accttcctga cagcccagac tctgctcatg   960
gatctgggc agttcctgct cttttgccac atcagctccc accagcatga tggaatggag   1020
gcatatgtga aagtggactc tgcccagag gaaccacacg tgaggatgaa gaacaatgag   1080
gaagctgaag actatgatga tgacctgaca gactcagaga tggatgtggt caggtttgat   1140
gatgataaca gcccctccttt atccagatc agaagtgtgg ccaagaaaca cccaaagaca   1200
tgggtccatt acattgcagc tgaggaagag gactgggatt atgcacctct ggtgctggcc   1260
ccagatgata gatcctacaa atcacagtat ctgaacaatg accccagag gattggcaga   1320
aagtacaaga aagtgaggt catggcctat actgatgaaa catttaagac tagagaagct   1380
atccagcatg agtcaggcat cctgggacca ctgctctatg gaagagtggg ggacaccctg   1440
ctcatcatct tcaagaacca ggcttccagg ccatacaata tctatcctca tggcatcaca   1500
gatgtgagac cactctactc aaggagactg cctaaggggag tcaaacacct caaggacttc   1560
cctatcctgc caggggaaat ctttaagtat aaatggactg tgacagtgga ggatgggccc   1620
actaagagtg acccaaggtg cctgaccaga tactattcaa gttttgtgaa tatggaaagg   1680
```

```
gatctggcat caggactgat tggacctctg ctcatctgct acaaagagag tgtggatcag    1740
aggggcaacc agatcatgtc agacaagagg aatgtgatcc tgttcagtgt ctttgatgaa    1800
aacaggtctt ggtatctgac agagaacatc cagagattcc tgccaaatcc tgcaggggtg    1860
cagctggaag atccagagtt tcaggcctca aacatcatgc atagtatcaa tggatatgtg    1920
tttgacagtc tgcagctctc tgtgtgcctg catgaagtgc cctactggta tatcctgtcc    1980
attggagctc agacagattt cctgagtgtg ttctttttcag gctacacttt taagcataaa    2040
atggtctatg aggacacact gactctcttc ccttttagtg gggaaacagt gtttatgagc    2100
atggagaatc cagggctgtg gattctggga tgccacaaca gtgatttcag gaatagaggc    2160
atgactgctc tgctcaaagt gtctagctgt gacaagaaca caggggacta ctatgaagat    2220
tcttatgagg acatcagtgc ttatctgctc tccaaaaaca atgcaattga acccagatca    2280
ttcagtcaga atccacctgt gctgaagagg caccagagag agatcactag gactaccctg    2340
cagtcagatc aggaagagat tgactatgat gataccatct cagtggaaat gaagaaaagg    2400
gactttgata tctatgatga agatgagaac cagagtccaa ggtctttcca gaagaaaacc    2460
agacattact ttattgctgc agtggagagg ctgtgggatt atggaatgtc ctcaagtcca    2520
catgtgctga ggaatagggc acagtctggc agtgtgccctc agttcaagaa agtggtcttc    2580
caggagttta cagatggcag cttcactcag cctctgtaca ggggagaact caatgagcac    2640
ctgggggctgc tgggaccccta tatcagagct gaagtggagg ataacatcat ggtcaccttc    2700
aggaatcagg cttcaagacc ctacagtttt tattctagcc tgatcagcta tgaagaggac    2760
cagaggcagg gagctgaacc taggaaaaac tttgtgaagc caaatgagac caaaacatac    2820
ttttggaagg tccagcacca catggcacca accaaagatg agtttgattg caaggcatgg    2880
gcctattttt cagatgtgga tctggagaag gatgtccaca gtggcctcat tgggcctctg    2940
ctggtgtgcc atactaacac cctgaatcca gctcatgcgca ggcaggtgac agtccaggag    3000
tttgcactgt tctttaccat ctttgatgag acaaagtcct ggtacttcac tgaaaacatg    3060
gagaggaatt gcagagctcc ttgcaacatc cagatggaag accccacctt caaggagaac    3120
tacagatttc atgcaatcaa tgggtatatc atggatacac tgccaggact ggtgatggcc    3180
caggaccaga ggatcagatg gtatctgctc agcatgggat ccaatgagaa tatccactct    3240
atccatttca gtggacatgt gtttacagtc agaaagaaag aagagtataa aatggccctg    3300
tacaacctct atccaggagt gtttgaaaca gtggagatgc tgccaagcaa ggctgggatc    3360
tggagggtgg aatgcctcat tggggagcac ctgcatgcag gaatgtcaac cctgtttctg    3420
gtctacagta ataagtgcca gacacctctg ggaatgacaa gtggacatat cagggatttc    3480
cagatcactg ctagtggaca gtatggacag tgggcaccaa agctggctag actccactat    3540
tcaggctcaa tcaatgcttg gtccaccaaa gagccattct catggatcaa ggtggacctg    3600
ctggctccta tgatcatcca tggcatcaaa acacaggggg caaggcagaa gttctcctca    3660
ctgtacatct ctcagtttat catcatgtat agcctggcga tgcaagaaatg gcagacctac    3720
aggggcaata gcacagggac tctgatggtg ttctttggga atgtggacag cagtgggatc    3780
aagcacaaca tcttcaatcc cccaatcatt gcaaggtaca tcagactgca ccccacccat    3840
tattcaatca ggagtacact caggatggaa ctgatggggt gtgatctcaa cagttgctct    3900
atgccactgg gaatggagtc caaggcaatc tcagatgccca gatcactgc tagctcctac    3960
ttcactaata tgtttgctac ctggagcccc tccaaagcaa ggctgcacct ccagggaagg    4020
agcaatgcat ggaggcctca ggtgaacaat cccaaggaat ggctgcaggt ggatttccag    4080
aaaactatga aggtgactgg agtcacaact caggggagtga aaagtctgct cacttctatg    4140
tatgtcaagg agttcctgat ctcaagttct caggatggcc accagtggac cctgttcttt    4200
cagaatggaa aggtgaaagt cttccagggc aatcaggatt cctttaccgc agtggtcaac    4260
tcactggacc ctcccctgct cactagatat ctgagaatcc accctcagag ctgggtgcat    4320
cagattgctc tcagaatgga agtcctgggc tgtgaggcac aggacctgta ttgag          4375
```

SEQ ID NO: 17           moltype = DNA  length = 2903
FEATURE                 Location/Qualifiers
misc_feature            1..2903
                        note = synthetic 6x-tRNA
source                  1..2903
                        mol_type = other DNA
                        organism = synthetic construct

SEQUENCE: 17

```
gtcgactacg tagaatccgg agccgtcttt gtcttccagc tccatctttt ccaccttttg     60
cttaggcagt cccccgagtc gtgtcaaggc tgaggagtag aaatggaaca gcactaatat    120
taatggcaaa accgttgtga aatagggtta ctttctgttt aagcaaggaa aataaagtaa    180
agcaatggga aaaaaattaa aagcaaaagg aatggaggtg ccggggattg aacccggggc    240
ctcgtgcatg ctaagcacgc gctctaccac tgagctacac ccccgtactg aaacggttca    300
ctcgagagta tattcaagat cagaatctga ccctttttgct aggtttcaga accattagtt    360
gtaatcagcc aagtctcatt ttatttagtt atttctgata tctcaaattt aggttttgcg    420
tccctctttg ctgacagctg agcaaaccgc attctacacc gaaggccctc tattgatggc    480
cctgatttaa atcccttccg ccgcctgccg caggtggcta gggtctgagc acacttgaac    540
ctcacacccg ccccaggggt agctccttgg ttccctttcag ggctgcaatc tccctcgtgc    600
tttgaaatgg aattacagtt ttggttaaaa acatgccttt tccgagttag gaagaatcta    660
aatcgactga acgccagtct aaaatttcgg cgttcccaca ccgggagtcg aacccgggcc    720
gcctgggtga aaaccaggaa tcctaaccgc tagaccatgt gggagacggc aatagcgact    780
ccaagcctag acaaattgag tcttctcggt cggcttccgc ccactccatc gcgttcatcc    840
gtaggcgtca aacctgctcc tgcgcctgcg cggagtctgc agcggtttaa accgttcagg    900
ttcgcattct actgtttctc tccttgcagg ggccccttgaa tctttcttca atctactctc    960
gcgtgcccgg gcgactgggc ataaccctac aggttcatgt ggggtggggtg gcgcgcgcta   1020
gcggtgaagg tcactcacaa ttgcgcgctg gcagacgac ggcagccatt acttttacct   1080
cgatcgctgt tttcctggat ccgcacgggt ccaacccgac tcatcccaac caacctgagg   1140
tatgaaaacc aggaaagaga gctagcaccg gagcgttggt ggtatagtgg taagcatagc   1200
tgccttccaa gcagttgacc cgggttcgat tcccggccaa cgcaagtcgt tttgggtgtt   1260
ttttcccccc cccgcctttt ccttttcgtg ttttctgggc cccagcatcg ttgagggttt   1320
tcgtgaggtt ttcctgagga aacttccgct ccgaaaggac ccactttccg ctacacccgc   1380
gaccacggct ggaccaccgc gctcctgacg gatgcgccct gcaagccct ccaggcgaga   1440
gcaggccggc ctgtgctcag ttttgtagca tcaaaactag gatttctctt gttaccccca   1500
```

```
gtcactccat tcagttttcg tgtctttccc agctgcatcc atcctttcct catttttcgta  1560
tgcagccgac tttttgtgac atctttgtat tcattctctg caattcagct gacctggcca  1620
aggaaacaag atcctaagcg tctttccggc ggcgccgtgg cttagttggt taaagcgcct  1680
gtctagtaaa caggagatcc tgggttcgaa tcccagcggt gcctccgtgt ttcccccacg  1740
cttttgccaa cattaaacat tgtgaggaca gttgcagaaa ctcataactt ccatcctaca  1800
tggtttactc acgtacccat ctatcctctc ccggtgcatc tgccacacgc tgttgggttt  1860
ttgctcttcg tgcacatggt acttgcgcct cgacctgcag ttacaccagt cgcatcatct  1920
gtacagcgct aaaacctagc tgggcgtggt ggtcctgcag tcccagctac tcgggaggct  1980
gaggcaggag aatggcttga atccaggagg cggaggtggc agtgagccga gattgcgcca  2040
ctgcactcca gcctggtgac agagcgagac tccatctcaa aaaaaaaaaa aaaaaaaaag  2100
tcagaattag gtactaaaag ccatatgaca tgcctgaaca gggacttgaa ccctggaccc  2160
tcagattaaa agtctgatgc tctaccaact gagctatcca ggcttcttcc ctgctagttt  2220
attttaatgc agtaataaat aacagcactt tgttaaaaat aataaaggta taatctgtga  2280
cacatcccaaa gtggacaaga tgaagagata ataggtatac accaggattc ccctgggcaa  2340
actgggacct cttggtaccc tatatattaa gagtctcggg ttttgttttc acttaagcaa  2400
atggttaacg aattagcagg ttaagaaaaa ctgtttcccc gtaagaagca gggttctttg  2460
gtgttcaatg tggagctccg ccactcccag cccgggtgaa ggaaaactgg gaaacagaat  2520
gaatgtgatt atctattcga agataaattt ccacaaagca tgccgtttga tagtagctta  2580
taatgtggaa gtaaggcatc ctgtcatccg gccggttagc tcagttggtt agagcgtggt  2640
gctaataacg ccaaggtcgc gggttcgatc ccgtactggc caagtattc tctgtggctt  2700
ttatcaccag aatggatagt aacccagaca tcgatctaaa cgtgtacctg tgtgtttctc  2760
caggcttaac tttgccccga gaaaacggat ctgtgaattt ggtgcgccct cgcttactcg  2820
acagcggtta atttgaacgg ggacgtttct ttccgctgcc tccaaggcat acccacatcc  2880
taccacgatg gtggcggccg caa                                          2903
```

SEQ ID NO: 18          moltype = AA   length = 1467
FEATURE                Location/Qualifiers
REGION                 1..1467
                       note = synthetic HP44/OL aa
source                 1..1467
                       mol_type = protein
                       organism = synthetic construct
SEQUENCE: 18
MQLELSTCVF LCLLPLGFSA IRRYYLGAVE LSWDYRQSEL LRELHVDTRF PATAPGALPL  60
GPSVLYKKTV FVEFTDQLFS VARPRPPWMG LLGPTIQAEV YDTVVVTLKN MASHPVSLHA  120
VGVSFWKSSE GAEYEDHTSQ REKEDDKVLP GKSQTYVWQV LKENGPTASD PPCLTYSYLS  180
HVDLVKDLNS GLIGALLVCR EGSLTRERTQ NLHEFVLLFA VFDEGKSWHS ARNDSWTRAM  240
DPAPARAQPA MHTVNGYVNR SLPGLIGCHK KSVYWHVIGM GTSPEVHSIF LEGHTFLVRH  300
HRQASLEISP LTFLTAQTFL MDLGQFLLFC HISSHHHGGM EAHVRVESCA EEPQLRRKAD  360
EEEDYDDNLY DSDMDVVRLD GDDVSPFIQI RSVAKKHPKT WVHYISAEEE DWDYAPAVPS  420
PSDRSYKSLY LNSGPQRIGR KYKKARFVAY TDVTFKTRKA IPYESGILGP LLYGEVGDTL  480
LIIFKNKASR PYNIYPHGIT DVSALHPGRL LKGWKHLKDM PILPGETFKY KWTVTVEDGP  540
TKSDPRCLTR YYSSSINLEK DLASGLIGPL LICYKESVDQ RGNQMMSDKR NVILFSVFDE  600
NQSWYLAENI QRFLPNPDGL QPQDPEFQAS NIMHSINGYV FDSLQLSVCL HEVAYWYILS  660
VGAQTDFLSV FFSGYTFKHK MVYEDTLTLF PFSGETVFMS MENPGLWVLG CHNSDLRNRG  720
MTALLKVYSC DRDIGDYYDN TYEDIPGFLL SGKNVIEPRS FAQNSRPPSA SAPKPPVLRR  780
HQRDISLPTF QPEEDKMDYD DIFSTETKGE DFDIYGEDEN QDPRSFQKRT RHYFIAAVEQ  840
LWDYGMSESP RALRNRAQNG EVPRFKKVVF REFADGSFTQ PSYRGELNKH LGLLGPYIRA  900
EVEDNIMVTF KNQASRPYSF YSSLISYPDD QEQGAEPRHN FVQPNETRTY FWKVQHHMAP  960
TEDEFDCKAW AYFSDVDLEK DVHSGLIGPL LICRANTLNA AHGRQVTVQE FALFFTIFDE  1020
TKSWYFTENV ERNCRAPCHL QMEDPTLKEN YRFHAINGYV MDTLPGLVMA QNQRIRWYLL  1080
SMGSNENIHS IHFSGHVFSV RKKEEYKMAV YNLYPGVFET VEMLPSKVGI WRIECLIGEH  1140
LQAGMSTTFL VYSKKCQTPL GMASGHIRDF QITASGQYGQ WAPKLARLHY SGSINAWSTK  1200
EPFSWIKVDL LAPMIIHGIK TQGARQKFSS LYISQFIIMY SLDGKKWQTY RGNSTGTLMV  1260
FFGNVDSSGI KHNIFNPPII ARYIRLHPTH YSIRSTLRME LMGCDLNSCS MPLGMESKAI  1320
SDAQITASSY FTNMFATWSP SKARLHLQGR SNAWRPQVNN PKEWLQVDFQ KTMKVTGVTT  1380
QGVKSLLTSM YVKEFLISSS QDGHQWTLFF QNGKVKVFQG NQDSFTPVVN SLDPPLLTRY  1440
LRIHPQSWVH QIALRMEVLG CEAQDLY                                      1467

SEQ ID NO: 19          moltype = DNA   length = 4401
FEATURE                Location/Qualifiers
misc_feature           1..4401
                       note = synthetic HP44/OL NT
source                 1..4401
                       mol_type = other DNA
                       organism = synthetic construct
SEQUENCE: 19
atgcagctag agctctccac ctgtgtcttt ctgtgtctct tgccactcgg ctttagtgcc  60
atcaggagat actacctggg cgcagtggaa ctgtcctggg actaccggca aagtgaactc  120
ctccgtgagc tgcacgtgga caccagattt cctgctacag cgccaggagc tcttccgttg  180
ggcccgtcag tcctgtacaa aaaagactgtg ttcgtagagt tcacggatca acttttcagc  240
gttgccaggc ccaggccacc atggatgggt ctgctgggtc ctaccatcca ggctgaggtt  300
tacgcacacg tggtcgttac cctgaagaac atggcttctc atcccgttag tcttcacgct  360
gtcggcgtct ccttctggaa atcttccgaa ggcgctgaat atgaggatca cacagccgca  420
agggagaagg aagacgataa agtccttccc ggtaaaagcc aaacctacgt ctggcaggtc  480
ctgaaagaaa atggtccaac agcctctgac ccaccatgtc ttacctactc ataccctgtct  540
cacgtggacc tggtgaaaga cctgaattcg ggcctcattg gagccctgct ggtttgtaga  600
gaagggagtc tgaccagaga aaggacccag aacctgcacg aatttgtact actttttgct  660
gtctttgatg aagggaaaag ttggcactca gcaagaaatg actcctggac acgggccatg  720
```

-continued

```
gatcccgcac ctgccagggc ccagcctgca atgcacacag tcaatggcta tgtcaacagg   780
tctctgccag gtctgatcgg atgtcataag aaatcagtct actggcacgt gattggaatg   840
ggcaccagcc cggaagtgca ctccattttt cttgaaggcc acacgtttct cgtgaggcac   900
catcgccagg cttccttgga gatctcgcca ctaactttcc tcactgctca gacattcctg   960
atggaccttg gccagttcct actgttttgt catatctctt cccaccacca tggtggcatg   1020
gaggctcacg tcagagtaga aagctgcgcc gaggagcccc agctgcggag gaaagctgat   1080
gaagaggaag attatgatga caatttgtac gactcggaca tggacgtggt ccggctcgat   1140
ggtgacgacg tgtctccctt tatccaaatc cgctcggttg ccaagaagca tcccaaaacc   1200
tgggtgcact acatctctgc agaggaggag gactgggact acgcccccgc ggtccccagc   1260
cccagtgaca gaagttataa aagtctctac ttgaacagtg gtcctcagcg aattggtagg   1320
aaatacaaaa aagctcgatt cgtcgcttac acggatgtaa catttaagac tcgtaaagct   1380
attccgtatg aatcaggaat cctgggacct ttactttatg gagaagttgg agacacactt   1440
ttgattatat ttaagaataa agcgagccga ccatataaca tctaccctca tggaatcact   1500
gatgtcagcg ctttgcaccc agggagactt ctaaaaggtt ggaaacattt gaaagacatg   1560
ccaattctgc caggagagac tttcaagtat aaatggacag tgactgtgga agatgggcca   1620
accaagtccg atcctcggtg cctgacccgc tactactcga gctccattaa tctagagaaa   1680
gatctggctt cgggactcat tggccctctc ctcatctgct acaaagaatc tgtagaccaa   1740
agaggaaacc agatgatgtc agacaagaga aacgtcatcc tgttttctgt attcgatgag   1800
aatcaaagct ggtacctcgc agagaatatt cagcgcttcc tccccaatcc ggatggatta   1860
cagccccagg atccagagtt ccaagcttct aacatcatgc acagcatcaa tggctatgtt   1920
tttgatagct tgcagctgtc ggtttgtttg cacgaggtgg catactggta cattctaagt   1980
gttggagcac agacggactt cctctccgtc ttcttctgct gctacaacct caaacacaaa   2040
atggtctatg aagacacact cacctgttc ccttctcag gagaaacggt cttcatgtca   2100
atggaaaacc caggtctctg ggtccttggg tgccacaact cagacttgcg gaacagaggg   2160
atgacagcct tactgaaggt gtatagttgt gacagggaca ttggtgatta ttatgacaac   2220
acttatgaag atattccagg cttcttgctg agtggaaaga atgtcattga acctaggagc   2280
tttgcccaga attcaagacc ccctagtgcg agcgctccaa agcctccggt cctgcgacgg   2340
catcagaggg acataagcct tcctactttt cagccggagg aagacaaaat ggactatgat   2400
gatatcttct caactgaaac gaaggggaa gattttgaca tttacggtga ggatgaaaat   2460
caggaccctc gcagctttca gaagagaacc cgacactatt tcattgctgc ggtggagcga   2520
ctctgggatt acgggatgag cgaatccccc cgggcgctaa gaaacagggc tcagaacgga   2580
gaggtgcctc ggttcaagaa ggtggtcttc cgggaatttg ctgacggctc cttcacgcag   2640
ccgtcgtacc gcgggaact caacaaacac ttggggctct tgggacccta catcagagcg   2700
gaagttgaag acaacatcat ggtaactttc aaaaaccagg cgtctcgtcc ctattccttc   2760
tactcgagcc ttatttctta tccggatgat caggagcagg gggcagaacc tcgacacaac   2820
ttcgtccagc caaatgaaac cagaacttac ttttggaaag tgcagcatca catggccaccc   2880
acagaagacg agtttgactg caaagcctgg gcctactttt ctgatgttga cctggaaaaa   2940
gatgtgcact caggcttgat cggcccccctt ctgatctgcc gcgccaacac cctgaacgct   3000
gctcacggta gacaagtgac cgtgcaagaa tttgctctgt ttttcactat ttttgatgag   3060
acaaagagct ggtacttcac tgaaaatgtg gaaaggaact gccgggcccc ctgccatctg   3120
cagatggagg accccactct gaaagaaaac tatcgcttcc atgcaatcaa tggctatgtg   3180
atggatacac tccctggctt agtaatggct cagaatcaaa ggatccgatg gtatctgctc   3240
agcatggcgac gcaatgaaaa tatccattcg attcatttta gcggacacgt gttcagtgta   3300
cggaaaaagg aggagtataa aatggccgtg tacaatctct atccgggtgt ctttgagaca   3360
gtggaaatgc taccgtccaa agttggaatt tggcgaatag aatgcctgat tggcgagcac   3420
ctgcaagctg ggatgagcac gactttcctg gtgtacagca agaagtgtca gactcccctg   3480
ggaatggctt ctggacacat tagagatttt cagattacag cttcaggaca atatggacag   3540
tgggcccccaa agctgccag acttcattat tccggatcaa tcaatgcctg gagcaccaag   3600
gagcccttt cttggatcaa ggtggatctg ttggcaccaa tgattattca cggcatcaag   3660
acccagggtg cccgtcagaa gttctccagc ctctacatct ctcagtttat catcatgtat   3720
agtcttgatg ggaagaagtg gcagacttat cgaggaaatt ccactggaac cttaatggtc   3780
ttctttggca atgtggattc atctgggata aaacacaata tttttaaccc tccaattatt   3840
gctcgataca tccgtttgca cccaactcat tatagcattc gcagcactct tcgcatggag   3900
ttgatgggct gtgatttaaa tagttgcagc atgccattgg gaatggagag taaagcaata   3960
tcagatgcac agattactgc ttcatcctac tttaccaaata tgtttgccac ctggtctcct   4020
tcaaaagctc gacttcacct ccaagggagg agtaatgcct ggagacctca ggtgaataat   4080
ccaaaagagt ggctgcaagt ggacttccag aagacaatga aagtcacagg agtaactact   4140
cagggagtaa aatctctgct taccagcatg tatgtgaagg agttcctcat ctccagcagt   4200
caagatggcc atcagtggac tctcttttt cagaatggca aagtaaaggt ttttcaggga   4260
aatcaagact ccttcacacc tgtggtgaac tctctagacc caccgttact gactcgctac   4320
cttcgaattc accccccagag ttgggtgcac cagattgccc tgaggatgga ggtctgggc   4380
tgcgaggcac aggacctcta c                                             4401
```

```
SEQ ID NO: 20          moltype = AA  length = 1457
FEATURE                Location/Qualifiers
REGION                 1..1457
                       note = synthetic HP46/SQ aa
source                 1..1457
                       mol_type = protein
                       organism = synthetic construct
SEQUENCE: 20
MQLELSTCVF LCLLPLGFSA IRRYYLGAVE LSWDYRQSEL LRELHVDTRF PATAPGALPL   60
GPSVLYKKTV FVEFTDQLFS VARPRPPWMG LLGPTIQAEV YDTVVVTLKN MASHPVSLHA   120
VGVSFWKSSE GAEYEDHTSQ REKEDDKVLP GKSQTYVWQV LKENGPTASD PPCLTYSYLS   180
HVDLVKDLNS GLIGALLVCR EGSLTRERTQ NLHEFVLLFA VFDEGKSWHS ARNDSWTRAM   240
DPAPARAQPA MHTVNGYVNR SLPGLIGCHK KSVYWHVIGM GTSPEVHSIF LEGHTFLVRH   300
HRQASLEISP LTFLTAQTFL MDLGQFLLFC HISSHHHGGM EAHVRVESCA EEPQLRRKAD   360
EEEDYDDNLY DSDMDVVRLD GDDVSPFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
```

-continued

```
LIIFKNQASR PYNIYPHGIT DVRPLYSRRL PKGVKHLKDF PILPGEIFKY KWTVTVEDGP    540
TKSDPRCLTR YYSSFVNMER DLASGLIGPL LICYKESVDQ RGNQIMSDKR NVILFSVFDE    600
NRSWYLTENI QRFLPNPAGV QLEDPEFQAS NIMHSINGYV FDSLQLSVCL HEVAYWYILS    660
IGAQTDFLSV FFSGYTFKHK MVYEDTLTLF PFSGETVFMS MENPGLWILG CHNSDFRNRG    720
MTALLKVSSC DKNTGDYYED SYEDISAYLL SKNNAIEPRS FSQNPPVLKR HQREITRTTL    780
QSDQEEIDYD DTISVEMKKE DFDIYDEDEN QSPRSFQKKT RHYFIAAVER LWDYGMSSSP    840
HVLRNRAQSG SVPQFKKVVF QEFTDGSFTQ PLYRGELNEH LGLLGPYIRA EVEDNIMVTF    900
RNQASRPYSF YSSLISYEED QRQGAEPRKN FVKPNETKTY FWKVQHHMAP TKDEFDCKAW    960
AYFSDVDLEK DVHSGLIGPL LVCHTNTLNP AHGRQVTVQE FALFFTIFDE TKSWYFTENM   1020
ERNCRAPCNI QMEDPTFKEN YRFHAINGYI MDTLPGLVMA QDQRIRWYLL SMGSNENIHS   1080
IHFSGHVFTV RKKEEYKMAL YNLYPGVFET VEMLPSKAGI WRVECLIGEH LHAGMSTLFL   1140
VYSNKCQTPL GMASGHIRDF QITASGQYGQ WAPKLARLHY SGSINAWSTK EPFSWIKVDL   1200
LAPMIIHGIK TQGARQKFSS LYISQFIIMY SLDGKKWQTY RGNSTGTLMV FFGNVDSSGI   1260
KHNIFNPPII ARYIRLHPTH YSIRSTLRME LMGCDLNSCS MPLGMESKAI SDAQITASSY   1320
FTNMFATWSP SKARLHLQGR SNAWRPQVNN PKEWLQVDFQ KTMKVTGVTT QGVKSLLTSM   1380
YVKEFLISSS QDGHQWTLFF QNGKVKVFQG NQDSFTPVVN SLDPPLLTRY LRIHPQSWVH   1440
QIALRMEVLG CEAQDLY                                                  1457
```

```
SEQ ID NO: 21              moltype = DNA  length = 4368
FEATURE                    Location/Qualifiers
misc_feature               1..4368
                           note = synthetic HP46/SQ NT
source                     1..4368
                           mol_type = other DNA
                           organism = synthetic construct
SEQUENCE: 21
atgcagctag agctctccac ctgtgtcttt ctgtgtctct tgccactcgg ctttagtgcc    60
atcaggagat actacctggg cgcagtggaa ctgtcctggg actaccggca aagtgaactc   120
ctccgtgagc tgcacgtgga caccagattt cctgctacag cgccaggagc tcttccgttg   180
ggcccgtcag tcctgtacaa aaagactgtg ttcgtagagt tcacggatca acttttcagc   240
gttgccaggc ccaggccacc atggatgggt ctgctgggtc ctaccatcca ggctgaggtt   300
tacgacacgg tggtcgttac cctgaagaac atggcttctc atcccgttag tcttcacgct   360
gtcggcgtct ccttctggaa atcttccgaa ggcgctgaat atgaggatca caccagccaa   420
agggagaagg aagacgataa agtccttccc ggtaaaagcc aaacctacgt ctggcaggtc   480
ctgaaagaaa atggtccaac agcctctgac ccaccatgtc ttacctactc atacctgtct   540
cacgtggacc tggtgaaaga cctgaattcg ggcctcattg gagccctgct ggtttgtaga   600
gaagggagtc tgaccagaga aaggacccag aacctgcacg aatttgtact acttttgct   660
gtctttgatg aagggaaaag ttggcactca gcaagaaatg actcctggac acgggccatg   720
gatcccgcac ctgccagggc ccagcctgca atgcacacag tcaatggcta tgtcaacagg   780
tctctgccag tctgatcgg atgtcataag aaatcagtct actggcacgt gattggaatg   840
ggcaccagcc cggaagtgca ctccattttt cttgaaggcc acacgtttct cgtgaggcac   900
catcgccagg cttccttgga gatctcgcca ctaactttcc tcactgctca gacattcctg   960
atggaccttg gccagttcct actgttttgt catatctctt cccaccacca tggtggcatg   1020
gaggctcacg tcagagtaga aagctgcgcc gaggagcccc agctgcggag gaaagctgat   1080
gaagaggaag attatgatga caatttgtac gactcggaca tggacgtggt ccggctcgat   1140
ggtgacacg tgtctccctt tatccaaatc cgctcagttg ccaagaagca tcctaaaact   1200
tgggtacatt acattgctgc tgaagaggag gactgggact atggctccct agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac gcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atccgcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg cactcggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct actgaaggt ttctagttgt gacaagaaca ctggtgatta ttacgaggac   2220
agttatgaag atatttcagc atacttgcta gtaaaaaaca atgccattga acctaggagc   2280
ttctctcaga atccaccagt cttgaaacgc atcaacgggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaatttta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggtacccctt   2940
ctggtctgcc acactaacac actgaaccct gctcatggga acaagtgac agtacaggaa   3000
tttgctctgt ttttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
```

```
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactccctg ggaatggctt ctggacacat tagagatttt   3480
cagattacag cttcaggaca atatggacag tgggccccaa agctggccag acttcattat   3540
tccggatcaa tcaatgcctg gagcaccaag gagcccttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt ttttcaggga aatcaagact ccttcacacc tgtggtgaac   4260
tctctagacc caccgttact gactcgctac cttcgaattc accccagag ttgggtgcac   4320
cagattgccc tgaggatgga ggttctgggc tgcgaggcac aggacctc           4368
```

```
SEQ ID NO: 22          moltype = AA   length = 1467
FEATURE                Location/Qualifiers
REGION                 1..1467
                       note = synthetic HP47/OL aa
source                 1..1467
                       mol_type = protein
                       organism = synthetic construct
SEQUENCE: 22
MQLELSTCVF LCLLPLGFSA IRRYYLGAVE LSWDYRQSEL LRELHVDTRF PATAPGALPL   60
GPSVLYKKTV FVEFTDQLFS VARPRPPWMG LLGPTIQAEV YDTVVVTLKN MASHPVSLHA   120
VGVSFWKSSE GAEYEDHTSQ REKEDDKVLP GKSQTYVWQV LKENGPTASD PPCLTYSYLS   180
HVDLVKDLNS GLIGALLVCR EGSLTRERTQ NLHEFVLLFA VFDEGKSWHS ARNDSWTRAM   240
DPAPARAQPA MHTVNGYVNR SLPGLIGCHK KSVYWHVIGM GTSPEVHSIF LEGHTFLVRH   300
HRQASLEISP LTFLTAQTFL MDLGQFLLFC HISSHHHGGM EAHVRVESCA EEPQLRRKAD   360
EEEDYDDNLY DSDMDVVRLD GDDVSPFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FAQNSRPPSA SAPKPPVLRR   780
HQRDISLPTF QPEEDKMDYD DIFSTETKGE DFDIYGEDEN QDPRSFQKRT RHYFIAAVEQ   840
LWDYGMSESP RALRNRAQNG EVPRFKKVVF REFADGSFTQ PSYRGELNKH LGLLGPYIRA   900
EVEDNIMVTF KNQASRPYSF YSSLISYPDD QEQGAEPRHN FVQPNETRTY FWKVQHHMAP   960
TEDEFDCKAW AYFSDVDLEK DVHSGLIGPL LICRANTLNA AHGRQVTVQE FALFFTIFDE   1020
TKSWYFTENV ERNCRAPCHL QMEDPTLKEN YRFHAINGYV MDTLPGLVMA QNQRIRWYLL   1080
SMGSNENIHS IHFSGHVFSV RKKEEYKMAV YNLYPGVFET VEMLPSKVGI WRIECLIGEH   1140
LQAGMSTTFL VYSKKCQTPL GMASGHIRDF QITASGQYGQ WAPKLARLHY SGSINAWSTK   1200
EPFSWIKVDL LAPMIIHGIK TQGARQKFSS LYISQFIIMY SLDGKKWQTY RGNSTGTLMV   1260
FFGNVDSSGI KHNIFNPPII ARYIRLHPTH YSIRSTLRME LMGCDLNSCS MPLGMESKAI   1320
SDAQITASSY FTNMFATWSP SKARLHLQGR SNAWRPQVNN PKEWLQVDFQ KTMKVTGVTT   1380
QGVKSLLTSM YVKEFLISSS QDGHQWTLFF QNGKVKVFQG NQDSFTPVVN SLDPPLLTRY   1440
LRIHPQSWVH QIALRMEVLG CEAQDLY                                      1467
```

```
SEQ ID NO: 23          moltype = DNA   length = 4401
FEATURE                Location/Qualifiers
misc_feature           1..4401
                       note = synthetic HP47/OL NT
source                 1..4401
                       mol_type = other DNA
                       organism = synthetic construct
SEQUENCE: 23
atgcagctag agctctccac ctgtgtcttt ctgtgtctct tgccactcgg ctttagtgcc   60
atcaggagat actacctggg cgcagtggaa ctgtcctggg actaccggca aagtgaactc   120
ctccgtgagc tgcacgtgga caccagattt cctgctacag cgccaggagc tcttccgttg   180
ggcccgtcag tcctgtacaa aaagactgtg ttcgtagagt tcacggatca acttttcagc   240
gttgccaggc ccaggccacc atggatgggg ctgctgggtc taccatcca ggctgaggtt   300
tacgacacgg tggtcgttac cctgaagaac atggcttctc atcccgttag tcttcacgct   360
gtcggcgtct ccttctggaa atcttccgaa ggcgctgaat atgaggatca caccagccaa   420
agggagaagg aagacgataa agtccttccc ggtaaaagcc aaacctacgt ctggcaggtc   480
ctgaaagaaa atggtccaac agcctctgac ccaccatgtc ttacctactc atacctgtct   540
cacgtggacc tggtgaaaga cctgaattcg ggcctcattg gagccctgct ggtttgtaga   600
gaagggagtc tgaccagaga aaggacccag aacctgcacg aatttgtact acttttgct   660
gtctttgatg aagggaaaag ttggcactca gcaagaaatg actcctggac acgggccatg   720
gatcccgcac ctgccaggc ccagcctgca atgcacacag tcaatggcta tgtcaacagg   780
tctctgccag tctgatcgg atgtcataag aaatcagtct actggcacgt gattggaatg   840
ggcaccagcc cggaagtgca ctccattttt cttgaaggcc acacgtttct cgtgaggcac   900
catcgccagg cttccttgga gatctcgcca ctaacttcc tcactgctca gacattcctg   960
```

```
atggaccttg gccagttcct actgttttgt catatctctt cccaccacca tggtggcatg  1020
gaggctcacg tcagagtaga aagctgcgcc gaggagcccc agctgcggag gaaagctgat  1080
gaagaggaag attatgatga caatttgtac gactcggaca tggacgtggt ccggctcgat  1140
ggtgacgacg tgtctccctt tatccaaatc cgctcagttg ccaagaagca tcctaaaact  1200
tgggtacatt acattgctgc tgaagaggag gactgggact atgctccctt agtcctcgcg  1260
cccgatgaca gaagttataa aagtcaatat ttgaacaatg gccctcagcg gattggtagg  1320
aagtacaaaa aagtccgatt tatggcatac acagatgaaa cctttaagac gcgtgaagct  1380
attcagcatg aatcaggaat cttgggacct ttactttatg gggaagttgg agacacactg  1440
ttgattatat ttaagaatca agcaagcaga ccatataacc tctaccctca cggaatcact  1500
gatgtccgtc ctttgtattc aaggagatta ccaaaaggtg taaaacattt gaaggatttt  1560
ccaattctgc caggagaaat attcaaatat aaatggacag tgactgtaga agatgggcca  1620
actaaatcag atccgcggtg cctgacccgc tattactcta gtttcgttaa tatggagaga  1680
gatctagctt caggactcat tggccctctc ctcatctgct acaaagaatc tgtagatcaa  1740
agaggaaacc agataatgtc agacaagagg aatgtcatcc tgtttctgt atttgatgag  1800
aaccgaagct ggtacctcac agagaatata caacgctttc tccccaatcc agctggagtg  1860
cagcttgagg atccagagtt ccaagcctcc aacatcatgc acagcatcaa tggctatgtt  1920
tttgatagtt tgcagttgtc agtttgtttg catgaggtgg catactggta cattctaagc  1980
attggagcac agactgactt cctttctgtc ttcttctcgt gatatacctt caaacacaaa  2040
atggtctatg aagacacact caccctattc ccattctcag gagaaactgt cttcatgtcg  2100
atggaaaacc caggtctatg gattctgggg tgccacaact cagactttcg gaacagaggc  2160
atgaccgcct tactgaaggt ttctagttgt gacaagaaca ctggtgatta ttacgaggac  2220
agttatgaag atatttcagc atacttgctg agtaaaaaca atgccattga acctaggagc  2280
tttgcccaga attcaagacc ccctagtgcg agcgctccaa agcctccggt cctgcgacgg  2340
catcagaggg acataagcct tcctactttt cagccggagg aagacaaaat ggactatgat  2400
gatatcttct caactgaaac gaaggagaa gattttgaca tttacggtga ggatgaaaat  2460
caggaccctc gcagctttca gaagagaacc cgacactatt tcattgctgc ggtggagcag  2520
ctctgggatt acgggatgag cgaatccccc cgggcgctaa gaaacagggc tcagaacgga  2580
gaggtgcctc ggttcaagaa ggtggtcttc cgggaatttg ctgacggctc cttcacgcag  2640
ccgtcgtacc gcgggaact caacaaacac ttggggctct tgggacccta catcagagcg  2700
gaagttgaag acaacatcat ggtaactttc aaaaaccagg cgtctcgtcc ctattccttc  2760
tactcgagcc ttatttctta tccggatgat caggagcaag gggcagaacc tcgacacaac  2820
ttcgtccagc caaatgaaac cagaacttac ttttggaaag tgcagcatca catggcaccc  2880
acagaagacg agtttgactg caaagcctgg gcctactttt ctgatgttga cctggaaaaa  2940
gatgtgcact caggcttgat cggccccctt ctgatctgcc gcgccaacac cctgaacgct  3000
gctcacggta gacaagtgac cgtgcaagaa tttgctctgt ttttcactat ttttgatgag  3060
acaaagagct ggtacttcac tgaaaatgtg gaaaggaact gccgggcccc ctgccatctg  3120
cagatggagg accccactct gaaagaaaac tatcgcttcc atgcaatcaa tggctatgtg  3180
atggatacac tccctggctt agtaatggct cagaatcaaa ggatccgatg gtatctgctc  3240
agcatggca gcaatgaaaa tatccattcg attcatttta gcggacacgt gttcagtgta  3300
cggaaaaagg aggagtataa aatggccgtg tacaatctct atccgggtgt ctttgagaca  3360
gtggaaatgc taccgtccaa agttggaatt tggcgaatag aatgcctgat tggcgagcac  3420
ctgcaagctg ggatgagcac gactttcctg gtgtacagca agaagtgtca gactcccctg  3480
ggaatggctt ctggacacat tagagatttt cagattacag cttcaggaca atatggacag  3540
tgggccccaa agctggccag acttcattat tccggatcaa tcaatgcctg gagcaccaag  3600
gagcccttt cttggatcaa ggtggatctg ttggcaccaa tgattattca cggcatcaag  3660
acccagggtg cccgtcagaa gttctccagc ctctacatct ctcagtttat catcatgtat  3720
agtcttgatg ggaagaagtg gcagacttat cgaggaaatt ccactggaac cttaatggtc  3780
ttctttggca atgtggattc atctgggata aaacacaata tttttaaccc tccaattatt  3840
gctcgataca tccgtttgca cccaactcat tatagcattc gcagcactct tcgcatggag  3900
ttgatgggct gtgatttaaa tagttgcagc atgccattgg gaatggagag taaagcaata  3960
tcagatgcac agattactgc ttcatcctac tttaccaata tgtttgccac ctggtctcct  4020
tcaaaagctc gacttcacct ccaagggag agtaatgcct ggagacctca ggtgaataat  4080
ccaaaagagt ggctgcaagt ggacttccag aagacaatga aagtcacagg agtaactact  4140
cagggagtaa aatctctgct taccagcatg tatgtgaagg agttcctcat ctccagcagt  4200
caagatggcc atcagtggac tctcttttt cagaatggca aagtaaaggt ttttcaggga  4260
aatcaagact ccttcacacc tgtggtgaac tctctagacc caccgttact gactcgctac  4320
cttcgaattc accccagag ttgggtgcac cagattgccc tgaggatgga ggttctgggc  4380
tgcgaggcac aggacctcta c                                            4401
```

```
SEQ ID NO: 24         moltype = AA  length = 1457
FEATURE               Location/Qualifiers
source                1..1457
                      mol_type = protein
                      organism = Homo sapiens
SEQUENCE: 24
MQIELSTCFF LCLLRFCFSA TRRYYLGAVE LSWDYMQSDL GELPVDARFP PRVPKSFPFN  60
TSVVYKKTLF VEFTVHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSQNPPVLKR HQREITRTTL  780
QSDQEEIYD DTISVEMKKE DFDIYDEDEN QSPRSFQKKT RHYFIAAVER LWDYGMSSSP  840
```

```
HVLRNRAQSG SVPQFKKVVF QEFTDGSFTQ PLYRGELNEH LGLLGPYIRA EVEDNIMVTF   900
RNQASRPYSF YSSLISYEED QRQGAEPRKN FVKPNETKTY FWKVQHHMAP TKDEFDCKAW   960
AYFSDVDLEK DVHSGLIGPL LVCHTNTLNP AHGRQVTVQE FALFFTIFDE TKSWYFTENM  1020
ERNCRAPCNI QMEDPTFKEN YRFHAINGYI MDTLPGLVMA QDQRIRWYLL SMGSNENIHS  1080
IHFSGHVFTV RKKEEYKMAL YNLYPGVFET VEMLPSKAGI WRVECLIGEH LHAGMSTLFL  1140
VYSNKCQTPL GMASGHIRDF QITASGQYGQ WAPKLARLHY SGSINAWSTK EPFSWIKVDL  1200
LAPMIIHGIK TQGARQKFSS LYISQFIIMY SLDGKKWQTY RGNSTGTLMV FFGNVDSSGI  1260
KHNIFNPPII ARYIRLHPTH YSIRSTLRME LMGCDLNSCS MPLGMESKAI SDAQITASSY  1320
FTNMFATWSP SKARLHLQGR SNAWRPQVNN PKEWLQVDPQ KTMKVTGVTT QGVKSLLTSM  1380
YVKEFLISSS QDGHQWTLFF QNGKVKVFQG NQDSFTPVVN SLDPPLLTRY LRIHPQSWVH  1440
QIALRMEVLG CEAQDLY                                                 1457
```

SEQ ID NO: 25          moltype = DNA  length = 4371
FEATURE                Location/Qualifiers
source                 1..4371
                       mol_type = other DNA
                       organism = Homo sapiens
SEQUENCE: 25

```
atgcaaatag agctctccac ctgcttcttt ctgtgccttt tgcgattctg ctttagtgcc    60
accagaagat actacctggg tgcagtggaa ctgtcatggg actatatgca aagtgatctc   120
ggtgagctgc ctgtggacgc aagatttcct cctagagtgc caaaatcttt tccattcaac   180
acctcagtcg tgtacaaaaa gactctgttt gtagaattca ggttcacct tttcaacatc   240
gctaagccaa ggccaccctg gatgggtctg ctaggtccta ccatccaggc tgaggtttat   300
gatacagtgg tcattacact taagaacatg gcttcccatc ctgtcagtct tcatgctgtt   360
ggtgtatcct actggaaagc ttctgaggga gctgaatatg atgatcagac cagtcaaagg   420
gagaaagaag atgataaagt cttccctggt ggaagccata catgtgtctg gcaggtcctg   480
aaagagaatg gtccaatggc ctctgaccca ctgtgcctta cctactcata tctttctcat   540
gtggacctgg taaaagactt gaattcaggc ctcattggag ccctactagt atgtagagaa   600
gggagtctgc ccaaggaaaa gacacagacc ttgcacaaat ttatactact ttttgctgta   660
tttgatgaag ggaaaagttg gcactcagaa acaaagaact cctgatgca ggatagggat   720
gctgcatctg ctcgggcctg gcctaaaatg cacacagtca atggttatgt aaacaggtct   780
ctgccaggtc tgattggatg ccacaggaaa tcagtctatt ggcatgtgat tggaatgggc   840
accactcctg aagtgcactc aatattcctc gaaggtcaca catttcttgt gaggaaccat   900
cgccaggcgt ccttggaaat ctcgccaata actttcctta ctgctcaaac actcttgatg   960
gaccttggac agtttctact gttttgtcat atctcttccc accaacatga tggcatggaa  1020
gcttatgtca aagtagacag ctgtccagag gaaccccaac tacgaatgaa aaataatgaa  1080
gaagcggaag actatgatga tgatcttact gattctgaaa tggatgtggt caggtttgat  1140
gatgacaact ctccttcctt tatccaaatt cgctcagttg ccaagaagca tcctaaaact  1200
tgggtacatt acattgctgc tgaagaggag gactgggact atgctccctt agtcctcgcc  1260
cccgatgaca gaagttataa aagtcaatat ttgaacaatg gccctcagcg gattggtagg  1320
aagtacaaaa aagtccgatt tatggcatac acagatgaaa cctttaagac gcgtgaagct  1380
attcagcatg aatcaggaat cttgggacct ttactttatg gggaagttgg agacacactg  1440
ttgattatat ttaagaatca agcaagcaga ccatataacc tctacctca cggaatcact  1500
gatgtccgtc ctttgtattc aaggagatta ccaaaaggtg taaaacattt gaaggatttt  1560
ccaattctgc aggagaaat attcaaatat aaatgacag tgactgtaga agatgggcca  1620
actaaatcag atccgcggtg cctgacccgc tattactcta gtttcgttaa tatggagaga  1680
gatctagctt caggactcat tggccctctc ctcatctgct acaaagaatc tgtagatcaa  1740
agaggaaacc agataatgtc agacaagagg aatgtcatcc tgttttctgt atttgatgag  1800
aaccgaagct ggtacctcac agagaatata caacgctttc tccccaatcc agctggagtg  1860
cagcttgagg atccagagtt ccaagcctcc aacatcatgc acagcatcaa tggctatgtt  1920
tttgatgtt tgcagttgtc agtttgtttg catgaggtgg catactggta cattctaagc  1980
attggagcac agactgactt cctttctgtc ttcttctctg gatatacctt caaacacaaa  2040
atggtctatg aagacacact caccctattc ccattctcag gagaaactgt cttcatgtcg  2100
atggaaaacc caggtctatg gattctgggg tgccacaact cagactttcg gaacagaggc  2160
atgaccgcct tactgaaggt ttctagttgt gacaagaaca ctggtgatta ttacgaggac  2220
agttatgaag atatttcagc atacttgctg agtaaaaaca atgccattga acctaggagc  2280
ttctctcaga atccaccagt cttgaaacgc atcaacgggg aaataactcg tactactctt  2340
cagtcagatc aagaggaaat tgactatgat gataccatat cagttgaaat gaagaaggaa  2400
gattttgaca tttatgatga tgatgaaat cagagccccc gcagctttca aaagaaaaca  2460
cgcacactatt ttattgctgc agtggagagg ctctgggatt atgggatgag tagctcccca  2520
catgttctaa gaaacagggc tcagagtggc agtgtccctc agttcaagaa agttgttttc  2580
caggaattta ctgatggctc ctttactcag cccttatacc gtggagaact aaatgaacat  2640
ttgggactcc tggggccata tataagagca gaagttgaag ataatatcat ggtaactttc  2700
agaaatcagg cctctcgtcc ctattccttc tattctagcc ttattctta cggaatcact  2760
cagaggcaag gagcagaacc tagaaaaaac tttgtcaagc ctaatgaaac caaaacttac  2820
ttttggaaag tgcaacatca tatggcaccc actaaagatg agtttgactg caaagcctgg  2880
gcttatttct ctgatgttga cctggaaaaa gatgtgcact caggcctgat tggacccctt  2940
ctggtctgcc acactaacac gctcaaccct gctcatggga gacaagtgac agtacaggaa  3000
tttgctcttt ttttcaccat ctttgatgag accaaaagct ggtacttcac tgaaaatatg  3060
gaaagaaact gcagggctcc ctgcaatatc cagatggaag atcccacttt taaagagaat  3120
tatcgcttcc atgcaatcaa tggctacata atggatacac tacctggctt agtaatggct  3180
caggatcaaa ggattcgatg gtatctgctc agcatgggca gcaatgaaaa catccattct  3240
attcatttca gtggacatgt gttcactgta cgaaaaaaag aggagtataa aatggcactg  3300
tacaatctct atccaggtgt ttttgagacg agtggaaatg taccatcaa agctggaatt  3360
tggcgggtgg aatgccttat tggcgagcat ctacatgctg ggatgagcac acttttttctg  3420
gtgtacagca ataagtgtca gactcccctg ggaatggctc tggacacat tagagatttt  3480
cagattacag cttcaggaca atatggacag tgggccccaa agctggccag acttcattat  3540
tccgatcaa tcaatgcctg gagcaccaag gagccctttt cttggatcaa ggtggatctg  3600
ttggcaccaa tgattattca cggcatcaag acccagggtg cccgtcagaa gttctccagc  3660
```

```
ctctacatct ctcagtttat catcatgtat agtcttgatg ggaagaagtg gcagacttat 3720
cgaggaaatt ccactggaac cttaatggtc ttctttggca atgtggattc atctgggata 3780
aaacacaata tttttaaccc tccaattatt gctcgataca tccgtttgca cccaactcat 3840
tatagcattc gcagcactct tcgcatggag ttgatgggct gtgatttaaa tagttgcagc 3900
atgccattgg gaatggagag taaagcaata tcagatgcac agattactgc ttcatcctac 3960
tttaccaata tgtttgccac ctggtctcct tcaaaagctc gacttcacct ccaagggagg 4020
agtaatgcct ggagacctca ggtgaataat ccaaaagagt ggctgcaagt ggacttccag 4080
aagacaatga aagtcacagg agtaactact cagggagtaa aatctctgct taccagcatg 4140
tatgtgaagg agttcctcat ctccagcagt caagatggcc atcagtggac tctctttttt 4200
cagaatggca aagtaaaggt ttttcaggga aatcaagact ccttcacacc tgtggtgaac 4260
tctctagacc caccgttact gactcgctac cttcgaattc accccagag ttgggtgcac 4320
cagattgccc tgaggatgga ggttctgggc tgcgaggcac aggacctcta c 4371
```

```
SEQ ID NO: 26          moltype = AA   length = 1467
FEATURE                Location/Qualifiers
REGION                 1..1467
                       note = synthetic HP63/OL aa
source                 1..1467
                       mol_type = protein
                       organism = synthetic construct
SEQUENCE: 26
MQLELSTCVF LCLLPLGFSA IRRYYLGAVE LSWDYRQSEL LRELHVDTRF PATAPGALPL    60
GPSVLYKKTV FVEFTDQLFS VARPRPPWMG LLGPTIQAEV YDTVVVTLKN MASHPVSLHA   120
VGVSFWKSSE GAEYEDHTSQ REKEDDKVLP GKSQTYVWQV LKENGPTASD PPCLTYSYLS   180
HVDLVKDLNS GLIGALLVCR EGSLTRERTQ NLHEFVLLFA VFDEGKSWHS ARNDSWTRAM   240
DPAPARAQPA MHTVNGYVNR SLPGLIGCHK KSVYWHVIGM GTSPEVHSIF LEGHTFLVRH   300
HRQASLEISP LTFLTAQTFL MDLGQFLLFC HISSHHHGGM EAHVRVESCA EEPQLRRKAD   360
EEEDYDDNLY DSDMDVVRLD GDDVSPFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNSRHPST RSQNPPVLKR   780
HQREITRTTL QSDQEEIDYD DTISVEMKKE DFDIYDEDEN QSPRSFQKRT RHYFIAAVEQ   840
LWDYGMSESP RALRNRAQNG EVPRFKKVVF REFADGSFTQ PSYRGELNKH LGLLGPYIRA   900
EVEDNIMVTF KNQASRPYSF YSSLISYPDD QEQGAEPRKN FVKPNETKTY FWKVQHHMAP   960
TEDEFDCKAW AYFSDVDLEK DVHSGLIGPL LICRANTLNA AHGRQVTVQE FALFFTIFDE  1020
TKSWYFTENV ERNCRAPCHL QMEDPTLKEN YRFHAINGYV MDTLPGLVMA QNQRIRWYLL  1080
SMGSNENIHS IHFSGHVFSV RKKEEYKMAV YNLYPGVFET VEMLPSKVGI WRNRCLIGEH  1140
LQAGMSTTFL VYSKKCQTPL GMASGHIRDF QITASGQYGQ WAPKLARLHY SGSINAWSTK  1200
EPFSWIKVDL LAPMIIHGIK TQGARQKFSS LYISQFIIMY SLDGKKWQTY RGNSTGTLMV  1260
FFGNVDSSGI KHNIFNPPII ARYIRLHPTH YSIRSTLRME LMGCDLNSCS MPLGMESKAI  1320
SDAQITASSY FTNMFATWSP SKARLHLQGR SNAWRPQVNN PKEWLQVDFQ KTMKVTGVTT  1380
QGVKSLLTSM YVKEFLISSS QDGHQWTLFF QNGKVKVFQG NQDSFTPVVN SLDPPLLTRY  1440
LRIHPQSWVH QIALRMEVLG CEAQDLY                                      1467
```

```
SEQ ID NO: 27          moltype = DNA   length = 4398
FEATURE                Location/Qualifiers
misc_feature           1..4398
                       note = synthetic HP63/OL NT
source                 1..4398
                       mol_type = other DNA
                       organism = synthetic construct
SEQUENCE: 27
atgcagctag agctctccac ctgtgtcttt ctgtgtctct tgccactcgg ctttagtgcc    60
atcaggagat actacctggg cgcagtggaa ctgtcctggg actaccggca aagtgaactc   120
ctccgtgagc tgcacgtgga caccagattt cctgctacag cgccaggagc tcttccgttg   180
ggcccgtcag tcctgtacaa aaagactgtg ttcgtagagt tcacggatca acttttcagc   240
gttgccaggc ccaggccacc atggatgggt ctgctgggtc ctaccatcca ggctgaggtt   300
tacgacacgg tggtcgttac cctgaagaac atggcttctc atcccgttag tcttcacgct   360
gtcggcgtct ccttctggaa atcttccgaa ggcgctgaat atgaggatca caccagccaa   420
agggagaagg aagacgataa agtccttccc ggtaaaagcc aaacctacgt ctggcaggtc   480
ctgaaagaaa atggtccaac agcctctgac ccaccatgtc ttacctactc atacctgtct   540
cacgtggacc tggtgaaaga cctgaattcg ggcctcattg gagccctgct ggtttgtaga   600
gaagggagtc tgaccagaga aaggacccag aacctgcacg aatttgtact acttttgct   660
gtctttgatg aaggggaaag ttggcactca gcaagaaatg actcctggac acgggccatg   720
gatcccgcac ctgccagggc ccagcctgca atgcacaccg tcaatggcta tgtcaacagg   780
tctctgccag gtctgatcgg atgtcataag aaatcagtct actggcacgt gattggaatg   840
ggcaccagcc cggaagtgca ctccattttt cttgaaggcc acacgtttct cgtgaggcac   900
catcgccagg cttccttgga gatctcgcca ctaacttttcc tcactgctca gacattcctg   960
atggaccttg ccagttcct actgttttgt catatctctt cccaccacca tggtggcatg  1020
gaggctcacg tcagagtaga aagctgcgcc gaggagcccc agctgcggag gaaagctgat  1080
gaagaggaag attatgatga caatttgtac gactcggaca tggacgttgt ccggctcgat  1140
ggtgacgacg tgtctccctt tatccaaatc cgctcagttg ccaagaagca tcctaaaact  1200
tgggtacatt acattgctgc tgaagaggag gactgggact atgctccctt agtcctcgcc  1260
cccgatgaca gaagttataa aagtcaatat ttgaacaatg ccctcagcg gattggtagg  1320
aagtacaaaa aagtccgatt tatggcatac acagatgaaa cctttaagac tcgtgaagct  1380
attcagcatg aatcaggaat cttgggacct ttactttatg gggaagttgg agacacactg  1440
```

```
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatatacctt caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga acctaggagc    2280
ttctcccaga attcaagaca ccctagcact aggtctcaaa acccaccagt cttgaaacgc    2340
catcaacggg aaataactcg tactactctt cagtcagatc aagaggaaat tgactatgat    2400
gataccatat cagttgaaat gaagaaggaa gattttgaca tttatgatga ggatgaaaat    2460
cagagccccc gcagctttca aaagagaacc cgacactatt tcattgctgc ggtggagcag    2520
ctctgggatt acgggatgag cgaatccccc cgggcgctaa gaaacagggc tcagaacgga    2580
gaggtgcctc ggttcaagaa ggtggtcttc cgggaatttg ctgacggctc cttcacgcag    2640
ccgtcgtacc gcgggggaact caacaaacac ttggggctct tgggacccta catcagacg    2700
gaagttgaag acaacatcat ggtaacttc aaaaaaccagg cgtctcgtcc ctattccttc    2760
tactcgagcc ttatttctta tccggatgat caggagcaag gggcagaacc tcgaaaaaac    2820
tttgtcaagc ctaatgaaac caaaaacttac ttttggaaag tgcagcatca catggcaccc    2880
acagaagacg agtttgactg caaagcctgg gcctactttt ctgatgttga cctggaaaaa    2940
gatgtgcact caggcttgat cggcccccctt ctgatctgcc gcgccaacac cctgaacgct    3000
gctcacggta gacaagtgac cgtgcaagaa tttgctctgt ttttcactat ttttgatgag    3060
acaaagagct ggtacttcac tgaaaatgtg gaaaggaact gccgggcccc ctgccatctg    3120
cagatggagg accccactct gaaagaaaac tatcgcttcc atgcaatcaa tggctatgtg    3180
atggatacac tccctggctt agtaatggct cagaatcaaa ggatccgatg gtatctgctc    3240
agcatgggca gcaatgaaaa tatccattcg attcatttta gcggacacgt gttcagtgta    3300
cggaaaaagg aggagtataa aatggccgtg tacaatctct atccgggtgt ctttgagaca    3360
gtggaaatgc taccgtccaa agttggaatt tggcggaata gatgcctgat tggcgagcac    3420
ctgcaagctg ggatgagcac gactttcctg gtgtacagca agaagtgtca gactccccctg    3480
ggaatggctt ctggacacat tagagatttt cagattacag cttcaggaca atatggacag    3540
tgggccccaa agctggccag acttcattat tccggatcaa tcaatgcctg gagcaccaag    3600
gagccctttt cttggatcaa ggtggatctg ttggcaccaa tgattattca cggcatcaag    3660
acccagggtg cccgtcagaa gttctccagc ctctacatct ctcagtttat catcatgtat    3720
agtcttgatg ggaagaagtg gcagacttat cgaggaaatt ccactgaaac cttaatggtc    3780
ttctttggca atgtggattc atctgggata aaacacaata ttttttaaccc tccaattatt    3840
gctcgataca tccgtttgca cccaactcat tatagcattc gcagcactct tcgcatggag    3900
ttgatgggct gtgatttaaa tagttgcagc atgccattgg gaatggagag taaagcaata    3960
tcagatgcac agattactgc ttcatcctac tttaccaata tgtttgccac ctggtctcct    4020
tcaaaagctc gacttcacct ccaagggagg agtaatgcct ggagacctca ggtgaataat    4080
ccaaaagagt ggctgcaagt ggacttccag aagacaatga aagtcacagg agtaactact    4140
cagggagtaa aatctctgct taccagcatg tatgtgaagg agttcctcat ctccagcagt    4200
caagatgcac atcagtggac ttttttttcag aatggcaaag taaaggtttt tcagggaaat    4260
caagactcct tcacacctgt ggtgaactct ctagacccac cgttactgac tcgctacctt    4320
cgaattcacc cccagagttg ggtgcaccag attgccctga ggatggaggt tctgggctgc    4380
gaggcacagg acctctac                                                    4398
```

SEQ ID NO: 28         moltype = DNA   length = 5508
FEATURE              Location/Qualifiers
source                1..5508
                          mol_type = other DNA
                          organism = Homo sapiens
SEQUENCE: 28

```
atgattcctg ccagatttgc cggggtgctg cttgctctgg ccctcatttt gccagggacc      60
ctttgtgcag aaggaactcg cggcaggtca tccacggtcc gatgcagcct tttcggaagt     120
gacttcgtca acacctttga tgggagacatg tacagctttg cgggatactg cagttacctc    180
ctggcagggg gctgccagaa acgctccttc tcgattattg gggacttcca gaatggcaag    240
agagtgagcc tctccgtgta tcttgggaa tttttttgaca tccatttgtt tgtcaatggt    300
accgtgacac aggggaccca aagagtctcc atgcccatg cctccaaagg gctgtatcta    360
gaaactgagg ctgggtacta caagctgtcc ggtgaggcct atggctttgt ggccaggatc    420
gatggcagcg gcaactttca agtcctgctg tcagacagat acttcaacaa gacctgcggg    480
ctgtgtggca actttaacat ctttgctgaa gatgactttta tgacccaaga agggaccttg    540
acctcggacc cttatgactt tgccaactca tgggctctga gcagtggaga acagtggtgt    600
gaacgggcat ctcctcccag cagctcatgc aacatctct ctggggaaat gcagaagggc    660
ctgtggaac agtgccagct tctgaagagc acctcggtgt ttgcccgctg ccaccctctg    720
gtggaccccg agcctttttgt ggccctgtgt gagaagactt tgtgtgagtg tgctggggggg    780
ctggagtgcg cctgccctgc cctcctggag tacgcccgga cctgtgccca ggagggaatg    840
gtgctgtacg gctggaccga ccacagcgcg tgcagcccag tgtgccctgc tggtatggag    900
tataggcagt gtgtgtcccc ttgcgccagg acctgccaga gcctgcacat caatgaaatg    960
tgtcaggagc gatgcgtgga tggctgaggac tgccctgagg gacagctcct ggatgaaggc    1020
ctctgcgtgg agagcaccga gtgtccctgc gtgcattccg gaaagcgcta ccctcccggc    1080
acctccctct ctcgagactg caacacctgc atttgccgaa acagccagtg gatctgcagc    1140
aatgaagaat gtccagggga gtgccttgtc acaggtcaat cacacttcaa gagctttgac    1200
aacagatact tcaccttcag tgggatctgc cagtacctgc tggcccggga ttgccaggac    1260
cactccttct ccattgtcat tgagactgtc cagtgtgctg atgaccgcga cgctgtgtgc    1320
```

-continued

```
acccgctccg tcaccgtccg gctgcctggc ctgcacaaca gccttgtgaa actgaagcat    1380
ggggcaggag ttgccatgga tggccaggac gtccagctcc ccctcctgaa aggtgacctc    1440
cgcatccagc atacagtgac ggcctccgtg cgcctcagct acggggagga cctgcagatg    1500
gactgggatg gccgcgggag gctgctggtg aagctgtccc ccgtctatgc cgggaagacc    1560
tgcggccgct gtgtgggaatta caatggcaac cagggcgacg acttccttac cccctctggg    1620
ctggcggagc cccgggtgga ggacttcggg aacgcctgga agctgcacgg ggactgccag    1680
gacctgcaga agcagcacag cgatccctgc gccctcaacc cgcgcatgac caggttctcc    1740
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggggagagg cgtgcgcgtc    1920
gcgtggcgcg agccaggccg ctgtgagctg aactgcccga aaggccaggt gtacctgcag    1980
tgcgggaccc cctgcaacct gacctgccgc tctctctctt acccggatga ggaatgcaat    2040
gaggcctgcc tggagggctg cttctgcccc ccagggctct acatggatga gagggggggac    2100
tgcgtgccca aggcccagtg cccctgttac tatgacggtg agatcttcca gccagagaac    2160
atcttctcag accatcacac catgtgctac tgtgaggatg gcttcatgca ctgtaccatg    2220
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc cccccgggca tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg gggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtgag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg gaatttttgat    3000
ggcatccaga acaatgacct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga atctccggga gaacgggtat    3420
gagtgtgagt ggcgctataa cagctgtgca cctgcctgtc aagtcacgtg tcagcaccct    3480
gagccactgg cctgccctgt gcagtgtgtg gagggctgcc atgcccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct tgaatcccag tgaccctgag    3660
cactgccaga tttgccactg tgatgttgtc aacctcacct gtgaagcctg ccaggagccg    3720
ggaggcctgg tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg gctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gcctgaagc ctcccgcatc    4140
accctgctcc tgatggccag ccaggagccc caacggatgt cccggaactt tgtccgctac    4200
gtccagggcc tgaagaagaa gaaggtcatt gtgatcccgg tgggcattgg gccccatgcc    4260
aacctcaagc agatccgcct catcgagaag caggcccctg agaacaaggc cttcgtgctg    4320
agcagtgtgg atgagctgga gcagcaaagg gacgagatcg ttagctacct ctgtgacctt    4380
gcccctgaag cccctcctcc tactctgccc cccgacatgg cacaagtcac tgtgggccc    4440
gggctcttgg gggtttcgac cctgggccc aagaggaact ccatggttct ggatgtggcg    4500
ttcgtcctgg aaggatcgga caaaattggt gaagccgact tcaacaggag caaggagttc    4560
atggaggagg tgattcagcg gatggatgtg ggccaggaca gcatccacgt cacggtgctg    4620
cagtactcct acatggtgac tgtggagtac cccttcagcg aggcacagtc caaaggggac    4680
atcctgcagc gggtgcgaga gatccgctac cagggcggca acaggaccaa cactgggctg    4740
gccctgcggt acctctctga ccacagcttc ttggtcagcc agggtgaccg ggagcaggcg    4800
cccaacctgg tctacatggt caccgacaaa cctgcctctg atgagatcaa gaggctgcct    4860
ggagacatcc aggtggtgcc cattggagtg ggccctaatg ccaacgtgca ggagctggag    4920
aggattggct ggcccaatgc ccctatcctc atccaggact ttgagacgct cccccgagag    4980
gctcctgacc tggtgctgca gaggtgctgc tccggagagg ggctgcagat ccccaccctc    5040
tcccctgcac ctcgtgatga gacgctccag gatggctgtg atactcactt ctgcaaggtc    5100
aatgagagag gagagtactt ctgggagaag agggtcaccag cgtgcccacc ctttgatgaa    5160
cacaagtgtc tggctgaggg aggtaaaatt atgaaaattc caggcacctg ctgtgacaca    5220
tgtgaggagc ctgagtgcaa cgacatcact gccaggctgc agtatgtcaa ggtgggaagc    5280
tgtaagtctg aagtagaggt ggatatccac tactgccagg gcaaatgtgc cagcaaagcc    5340
atgtactcca ttgacatcaa cgatgtgcag gaccagtgct cctgctgctc tccgacacgg    5400
acggagaccc tgcaggtggc cctgcactgc accaatggct ctgttgtgta ccatgaggtt    5460
ctcaatgcca tggagtgcaa atgctcccccc aggaagtgca gcaagtga    5508
```

SEQ ID NO: 29     moltype = DNA  length = 6648
FEATURE              Location/Qualifiers
source                1..6648
                      mol_type = other DNA
                      organism = Ovis aries
SEQUENCE: 29

```
atgtttccca ccaggctcgc gaggctgctg cttgctgtgg ccctcacttt gccaggggcc    60
ctttgtggag aaggtgctcc tggcaagtca tcgatggccc ggtgcagcct cttcggagct   120
```

-continued

```
gacttcatca acacctttga tgagagcatg tacagctttg cgggagactg tagttacctc    180
ctggcagggg attgcaagac acactccttt tcaatcgtag gggacttcca agctggtaga    240
agagtgggtc tctctgtgta ccttggggaa tttttcgaca tccatgtgtt tgtcaacggt    300
actgtgctgc aggggggcca gcatgtctcc atgccctatg ccaccagagg gctgtacctg    360
gacaccgagg ctgggtacca caagctgtcc agcgagtctt atggctttgt ggccaggatc    420
gacagcagcg ggaacttcca aatcctgctg tcggacagac acttcaacaa gacctgtggg    480
ctgtgcggtg actttaacat cttcgccgaa gatgacttca ggactcaaga aggaaccctg    540
acctcagacc cctacgactt tgcaaactcc tgggccctga gcagtgagga gcagcggtgt    600
ccacgggtgt cccctcccag cagctcctgc aacatctcct ctgagctgca gaagggcctg    660
tgggagcagt gccagcttct gaagacggcc tccgtgttcg cccgctgcca cgccctggtg    720
gaccccgagc ctttcgtggc cctgtgtgag cggatgctgt gcgcatgcgc ccaggggctg    780
cgctgcccct gcccggtgct cctggagtac gcccgcgcct gcgcccagca agggatgctg    840
ctgtacggct gggcggacca cagctcctgc cgaccggact gccccgcggg catggagtac    900
aaggagtgtg tgtccccatg ccacacaggacc tgccggagcc tgagtatcac cgaagtgtgt    960
cgggagcagt gtgtgggatgg ctgcagctgc cctgagggac agctcctgga tgaaggccgc   1020
tgtgtggaaa gtgccgagtg tccctgtgtg catgctggaa agccataccc tcctggcgcc   1080
tccctctcgc gagactgcaa cacctgcatc tgccgaaaca gccagtgggt ctgcagcaat   1140
gaggactgtc caggagagtg tctcatcaca ggacaatccc acttcaagag ctttgacgac   1200
aggcacttca ccttcagcgg ggtctgccaa tacctgctgg cccaggactg ccaggaccac   1260
tccttctccg tcatcataga gactgttcag tgtgctgacg accctgatgc ggtctgcacc   1320
cgctccgtca ccgtccgcct gcccagcccg caccacggcc tcctgaagct gaagcacggg   1380
ggtggagtcg ccctggatgg ccaggacgtc cagattcccg tacctgcaagg tgacctccgg   1440
atccagcaca ctgtgacggc ctccctgcac ctcatcttcg gggaggacct gcagatagac   1500
tgggacggtc gcgggaggct gctgctgaag ctgtccccgg tctacgcggg gaggacctgc   1560
gggctgtgcg ggaattacaa cggcaaccag agggatgact tcctgacgcc cgcgggcctg   1620
gtcgagcccc tggtggagca cttttggaaac tcctggaagc tacgtgcaga ctgtgaggac   1680
ttgcaggagc agcccagtga cccctgcagc ctcaacccgc gcctgaccaa gttcgcgac   1740
caggcctgcg ccatcctgac gtcccgcaag ttcgaggcct gccacagcgc cgtgggcccg   1800
ctgccctacc tgcgcaactg ccgcttcgac gtgtgcgcct gctccgatgg cagagactgc   1860
ctgtgcgaca cggtggccaa ctacgcggcg gcctgcgcca ggagggggcgt gcacatcggg   1920
tggcgggagc ccagcttctg tgcactgagc tgcccacacg gccaggtgta ccagcagtgt   1980
gggacccccct gcaacctcac ctgccgctca ctctcccacc cggacgagga atgcactgag   2040
gtctgtctgg agggctgctt ctgccctgct gggctcttcc tggatgagac ggggtcctgt   2100
gtgcccaagg cccagtgccc ctgttactat gacgggcgaga tcttccaacc tgaagacatc   2160
ttctcggacc atcacaccat gtgctactgc gaagatggct tcatgcactg ctccacgagc   2220
ggagccccgg ggagcctgct gcctgaagca gtcctcagca gccctctgtc ccaccgcagc   2280
aaaaggagcc tgtcctgccg gccccccatg gtcaagctgg tgtgccctgc tgacaacccg   2340
agggccgaag ggctcgaatg caccaagacc tgccagaact atgacctgga atgcgtgagc   2400
acgggctgtg tgtccggctg cctctgcccc ccgggcatgg tccggcatga gaacaggtgt   2460
gtggccctgg aaaggtgccc ctgcttccac cagggcagag agtacgcccc cggagacagg   2520
gtgaaggccg actgcaacac ctgcgtctgt caggaccgga agtggaactg tacggaccgc   2580
gtgtgtgatg ctggctgctc tgccgtgggc ctggctcact acttcacctt tgatgggctc   2640
aagtacctgt tcccggggga gtgccagtac gtcctggtac aggaccactg cggtagtaac   2700
cctgggacct tccgggtcct ggtggggaat gaggggtgca gcgctcccctc cctgaagtgc   2760
aggaagcgca tcaccatcct ggtggggga ggagagatcg agctgtttga cggggaggtg   2820
aacgtgaaga agcccatgaa ggatgagacg cacttcgagg tggtggaatc tggccggtac   2880
atcactgtgc tgctgggcaa ggccctctct gtggtctgga acgggcacct ggccatctct   2940
gtgttcctga agcggatgta ccaggagcgg gtatgcggcc tgtgtgggaa tttcgatggc   3000
gtccagaaca atgacctcac cagtagcagc ctccaagtgg aggaagaccc tgtggacttt   3060
gggaattcct ggaaagtgag cccgcattgc gctgacaccc agaaagtgcc gctggactcg   3120
gcccctgcca cctgccacaa gaacgtcatg aagcagacca tggtggattc ctcctgcagg   3180
gtcctcacca gtgatgtttt ccgggagtgc aacaggctgg tgaaccccga gccgtacctg   3240
gatgtttgca tctacgacag ctgctcctgc gagtccatcg gggactgcgc ctgcttctgt   3300
gacaccatcg ccgcctacgc ccacgagtgt gcccagcacg gcgaagtggt gacctggagg   3360
acagccacac tgtgccccca gaattgtgag gagcggaacc tgaaggagag tgggtaccaa   3420
tgtgagtggc gctacaacag ctgtgctccc gcctgtccag tcacgtgcca gcacccagag   3480
ccectggcct gccccgtgca gtgcgtggag ggctgccacg cacactgccc gcctgggaaa   3540
atcctggacg agcttttgca gacctgtgtc aaccccgagg actgccctgt gtgccaggtg   3600
gagggccggc gcttagcctc cgggaagaaa gtgaccctga accctgggga ccctgagcat   3660
tgccagctct gtcactgtga tggtgtcagc ctcacttgtg aagcctgcag ggagccagga   3720
ggcctgcccg tgccccccac cgaaggcccg gtcagcccca caaccccgta cgtgaggac   3780
accccggagc caccctgca cgacttcttc tgcagcaaac tgctggacct ggtcttcctg   3840
ctggacggct cctccaagct gtctgaggcc gacttcgaga cgctgaaggc gttcgtggtg   3900
ggcatgatgg agcgtctgca catttcccag aaacgcatcc gtgtggccgt gggtgagtac   3960
cacgatggct cccatgccta ccttgcactg caagaccgga agcggccatc cgagctgcgg   4020
cgcattgccg ggcaggtgaa gtacgcgggc agcgaggtgg cttccaccag cgaggtcttg   4080
aagtacacgc tcttccagat cttcggcagg attgaccggc ccgaggcctc tcgcgtggcc   4140
ctgctgctta cggccagcca ggagcccctg aggctggccc ggaacttggt ccgctacctc   4200
cagggcctga agaagaagaa ggtctccgtg gtcccggtgg gcatcgggcc ccacgtcagc   4260
ctcaagcaga tccgcctcat cgagaagcag gcgtctgaga acaaagcctt tgtgctaagc   4320
ggtgtgcacg agctggagca gcggatgaac gagattgtcg gctacctctg tgacctcgcc   4380
cccgaggtgc ctgccccgac cccgacgcga catcctctca ttgcgcaggt cactgtggcg   4440
ccgcagctcc tgggtccttc gccaccagga cccaagagga gctctgtggt cctggatgtg   4500
gcattcctcc tggaaggctc ggatgaggta ggcgagagca ccttcaacag gagcgcagag   4560
tttgtggagg aggtgatccg acgcatggac gttggccggg acggcatcca tgtcacggtg   4620
ctgcagtact cgtacacggt gaccgtggag cactcgttca gggagccaca gtccaaggag   4680
gtggtcctgc agcgactcca tgaagtccgc taccggggtg gcaaccagac gaacacgggg   4740
ctggccctgc agtacctgtc ggagcacagc ttctccgcca gccagggggga ccgggagcag   4800
gcgcccaacc tggtctacat ggtgacgggc agcccggcct cggacaagat ccagcggatg   4860
```

-continued

```
ccaggagaca tccagctcgt gcccatcggc gtgggccccc gtgtggacgt gcaggagctg  4920
gagagggtca gctggcccca gacccccatc ttcatccagg acttcgagag gctcccccga  4980
gaagctccgg atctggtgct gcagcggtgc tgctccgaag acggcccgca cctccccacc  5040
ctcgccctg ccccagactg cagccagccc ctggatgtag tcctcctcct ggatggctcc  5100
tccaccccctc cagcctctta ctttgacgaa atgaagagtt tcgccaaggc tttcatctca  5160
aaagccaacc taggccctca gcttacccag gtgtcagtcc tgcagtacgg gagcatcacc  5220
aacgtcgacg tatcctggaa tgtgcacgtg gacaaagccc acctgctgag ccttgtggac  5280
cccatgcagc gcgagggagg ccccagccga gtcggggagg cgttgtcctt cgcggtgcgc  5340
tacatcacgt cccaagtcca cggtgccagg cccggggcct ccaaggtggt ggtgatcctg  5400
gtcacaggct cctccatgga ctcagtggag gcggccgccg ctgctgccag atccaaccga  5460
gtggctgtgt tccccatcgg gatcggggac cagtatgacg cagcccagct gagggtcttg  5520
gcgggccgg gggccagctc caatgtggca gagctccagc ggattgaaga cctccccagc  5580
atggttgccc ttggcaactc cttcttccag aggctatgct ctgggttcgt cagtgtttgc  5640
gtggatgagg acgggaatga gaggaggcct ggggacgtct ggaccttgct ggatcagtgc  5700
cacacagtga cttgcctgcc agatggccag accttgctga agagtcaccg ggtcaactgt  5760
gatcaggggc cacagccatc atgccccgac ggccagatcc cgctcaggat ggaggaagcc  5820
tgtgtggctgcc gctgggcctg tccctgtgtg tgcacaggca gctccactcg gcacatcgtg  5880
acctttgatg gacggaattt caagctgacc ggcaactgct catacgttct gtttcacaac  5940
aaggagcagg acttggaggt gattctccat aacggattct gcagcgctgg ggcgaggcag  6000
gcctgcatga aatctgtgga ggtgaagcac agcggcctct cggttgagct ccgcagcaac  6060
atggaggtga tggtgaatgg gagactggtc tctgtcccctt acctgggtgg ggacatggag  6120
gtcagagtct atggtaccat catgttcgag gtcagattca accttctggg ccacatcctc  6180
tccttcaccc cacgtgatga gacactccag gatggctgtg acagtcactt ctgcaaagtc  6240
aacaagagag gagagttcat ttgggagaag agggtcatgg gctgcccgcc cttcaacgaa  6300
cacaaatgtc tggctgaggg ggggaaagtc atgaaaattc ctggcacgtg ctgtgacaca  6360
tgtgaggagc ccgagtgcaa ggacatcaca gccagggtgc agtacatcaa ggtggggagc  6420
tgcaaatctg aagaggaagt ggacattaac tactgccagg gaagatgcac cagcaaagcc  6480
ctgtactcca tcgacacgga ggacgtgcaa gaccagtgtt cctgctgctc gcccacgcgc  6540
acggagccca tgtcagtgcc cctgcgctgc accaacggct ccatcattca ccatgtgatc  6600
ctcaacgccc tgcagtgcaa gtgctcatcc aggaagtgcc gcccgtga              6648
```

```
SEQ ID NO: 30              moltype = AA  length = 24
FEATURE                    Location/Qualifiers
REGION                     1..24
                           note = synthetic porcine-derived linker sequence
source                     1..24
                           mol_type = protein
                           organism = synthetic construct
SEQUENCE: 30
SFAQNSRPPS ASAPKPPVLR RHQR                                         24

SEQ ID NO: 31              moltype = AA  length = 14
FEATURE                    Location/Qualifiers
REGION                     1..14
                           note = synthetic human linker sequence
source                     1..14
                           mol_type = protein
                           organism = synthetic construct
SEQUENCE: 31
SFSQNPPVLK RHQR                                                    14

SEQ ID NO: 32              moltype = AA  length = 6
FEATURE                    Location/Qualifiers
REGION                     1..6
                           note = synthetic 6-His tag
source                     1..6
                           mol_type = protein
                           organism = synthetic construct
SEQUENCE: 32
HHHHHH                                                             6

SEQ ID NO: 33              moltype = DNA  length = 4350
FEATURE                    Location/Qualifiers
misc_feature               1..4350
                           note = Synthetic truncated ovine (sheep) gene
source                     1..4350
                           mol_type = other DNA
                           organism = synthetic construct
SEQUENCE: 33
atgcacatca agctctgtac ctgcctcttt ctgtgcctct ggccatgcag cttcagtgcc  60
atcagaaagat actacctggg tgcagtggaa ctgtcctggg actatacgcg aagtgaactg  120
ctcagtgagc tgcatgtgaa cacgaggttt cctcccagag tgcccaaacc ttttccattc  180
aacacatcag tcatgtacag aaagactgtg tttgtagagt tcacggatca acttttaac  240
atcgccaagc ccaggccacc atggatgggt ctgctgggtc cagctatcca ggctgaggtt  300
tatgacaccg tggtcattac atttaagaat atggcttctc atcctgttag tcttcatgct  360
attggcgtat cctactggaa atcttctgaa ggtgctgcat ataaggatga aaccagccaa  420
agggagaagg aagatgacaa agtcattcct ggtaaaagtc atacctacgt ctggcatatc  480
ctgaaagaaa acggtccaac agcctctgac ccaccatgtc tcacctactc atatctttct  540
catgtggacc tggtgaaaga cgtgaactca ggtctcatcg gagccctgct aatttgtagg  600
```

-continued

```
gaagggactc tgatcaaaga aaggacacag accttgcaca aattcgtact actgtttgct  660
gtatttgatg aagggaaaag ttggcactcg ggaaaaaatg agtccttgac acatgttatg  720
gattctgcct ctgtactgca caccatcaat ggctatataa acaggtctct gccaggtctg  780
attggatgtc ataagaaatc agtctattgg catgtgattg gaatgggcac caccccagaa  840
gtgcactcaa ttttcctcga aggccacaca tttctcgtg ggaaccatcg ccaggcttcc  900
ttggagatct caccaataac tttccttacc gctcagacag tcctgatgga ctgtggccag  960
tttctactgt tttgtcgtat ctcttcccac caacatgatg gtatggaagc ttatgtcaaa  1020
gtagatagtt gcccagagga accccgacta tggatgaaaa ataaccaaga agaagattac  1080
gatgatggtt tggatgactc tgacatggat gtggtcaggt tcgatggtga cagtgtgcct  1140
ccctttatcc aaatgcgctc agttgcaaag aagcatccta aaacctgggt ccactacatt  1200
gctgctgaag aggatgactg ggactatgcc ccctcggtcc tcacctccaa tgacagaagt  1260
tataaaagtc tgtatctgaa ccacggtcct cagcggattg gtaggaagta cagaaaagta  1320
cgatttatag cttacacaga tggaacattt aagactcgtg aagctattca gcatgaatca  1380
gggatcctgg ggcctttact ttatggagaa gttggagaca cacttttgat tatatttaag  1440
aatcaagcaa gccggccata taacatctac cctcatggaa tcactgatgt cagtcctttg  1500
cactcaggga gatttccaaa aggtgtgaaa catttgaaag acatgccaat tctgccagga  1560
gaagtgttca agtataaatg gacagtgact gtagaagatg ggccaactaa atcagatcct  1620
cggtgtctga cccgatatta ctcgagtttc attaacttag agaaagatct agcttcagga  1680
ctcattggcc ccctcctcat ctgttacaaa gaatctgtag atcaaagagg aaaccagatg  1740
atgtcagaca agagaaatgt catcctgttt tctgtatttg atgaaaacaa aagttggtac  1800
ctcacagaga atattcaacg cttcctcccc agtggagtac agccccagga tccagagttc  1860
caagtctcca atgtcatgca cagcatcaat ggctatgttt ttgatagctt gcagctgtcg  1920
gtttgtttgc atgaggtggc gtactggtac attctaagtg ttggagccca aattgacttc  1980
ctctctgtct tcttctctgg atataccttc aaacacaaaa tggtctatga agacacactc  2040
accctattcc ccttctcggg agaaactgtc ttcatgtcaa tggaaaatcc aggtctgtgg  2100
gttctggggt gccacaactc agactttcga aacagaggca tgacagcctt actgaaggtt  2160
gatagttgtg acaggaacgt tggcgattat tatgacacat atgaagctat tccaaccttc  2220
ctgctgagtg aaaacaatgt cattgaaccc agaagcttct cccagaatcc accaagcttg  2280
aaacgccatc aaagggagat aaccccttact acttttcagc cagagccaga caaaactgac  2340
tatgatgata ctttgtcgat tgaaacaaag agagaagatt ttgacattta tggtgaagat  2400
gaaaatcagg accccgcag ctttcaaaag agaacacgcc actattttat tgctgcagtg  2460
gagcggctct gggattatgg gatgagtaga tcccccccacg cactaagaaa caggtctcag  2520
aatggaggag tccctcagtt caaaaaggtg gtgttcgagg aatttactga tggctccttt  2580
actcaggccg tataccgtgg acaattaaat gaacacctgg gactcttggg accatatata  2640
agagcagaag tggaagacaa tatcatggta actttcaaaa accaggcctc tcgtccctac  2700
tccttctatt ctagccttat ttcttataac ggagatcaga gacaaggagc agaacctcga  2760
aaaaagtttg tcaagcctaa tgaaacccaa agctactttt ggaaagtgca gcaccatatg  2820
gcacccacca aagatgagtt tgactgcaaa gcctgggctt acttttctga tgttgatctg  2880
gaaaaagatg tgcactcagg cttgattggc cccattctga tctgccgtgt gacacgctg  2940
agtgctgctc atgggagaca agtgacagta caggaattcg ctctgttttt caccattttt  3000
gatgagacca agagctggta ctttgccgaa aacatggcaa ggaactgcgt ggcaccctgc  3060
catgtccagc cagaggaccc tactttccaa gaaaagtatc gcttccatgc aatcaatggc  3120
tacgtgatgg atacactccc tggcttagtc atggctccaa atcaaaggat taggtggtat  3180
ctgctcagca tgggcagcaa tgaaaatatc cattccattc atttcagtgg ccatgtgttc  3240
actgtgagaa aaacgggagg gtataaaatg gcggtctaca atctctaccc aggtgtcttt  3300
gagaccgtgg aaatgctacc atccaaggtt gggacttggc ggatagaatg tcttattggc  3360
gagcacctac aagctgggat gagcactctc ttcctggtgt acagcaagga gtgtcaaatt  3420
ccactgggaa tggcttctgg acgcattaga gattttcaga ttacagcttc aggacaatat  3480
ggacagtggg ccccaaagct ggccagactt cattattctg gatcaatcaa tgcctggagc  3540
accaaggatc cctctccttg gatcaaggtg gatctgttgg cgccgatgat tattcacagc  3600
atcctgactc agggtgcccg gcagaagttc tccagcctgt acatctctca gtttatcatc  3660
atgtacagcc tcgatggaca gcggtggcag ggttatcggg ggaactccac tgggactttta  3720
atggtgttct ttggcaatgt ggattcatct ggagtaaaac acaatatttt taaccctcca  3780
attattgcta gatatatccg tttgcaccca acgcattaca gcatccgcag cactcttcgc  3840
atggagttga tgggctgtga cttaaatagt tgcaacatgc cactgggaat ggagaataaa  3900
gctatatcag atacacagat tactgcctca tcccacttaa gcaacatgtt tgccacctgg  3960
tctccttcac aagcccgact taaccttcaa gggaggacaa atgcctggag accccaggtg  4020
aataatccaa aagagtggct acaagtggac ttccagaaga caatgagagt tacaggaata  4080
accactcaag gggtgaaatc tctgcttacc agcatgtatg tgaaggagtt ccttatatcc  4140
agtagtcaag agggccataa ctggactcca tttcttcaga atggcaaagt gaaggttttt  4200
cagggaaatc aagactcctt cacccccgtg tgtaatactc tagaccccccc actgtttacc  4260
cgcttccttc ggattcaccc gcagagctgg gtgcaccata tcgccctgag gctggagttt  4320
tggggttgtg aggcacagca gcagtactag                                    4350
```

POST-NATAL TRANSPLANTATION OF FACTOR VIII-EXPRESSING CELLS FOR TREATMENT OF HEMOPHILIA

CROSS REFERENCE TO RELATED APPLICATION

This application is a continuation of U.S. Nonprovisional application Ser. No. 16/638,379, filed Feb. 11, 2020, which is a 371 National Stage of PCT Application No. PCT/US2018/047747, filed Aug. 23, 2018, which claims the benefit of U.S. Provisional Application Ser. No. 62/549,280, filed Aug. 23, 2017, and the contents of these applications are herein incorporated by reference in their entirety.

STATEMENT AS TO RIGHTS TO INVENTIONS MADE UNDER FEDERALLY SPONSORED RESEARCH AND DEVELOPMENT

This invention was made with government support under grant number 1R01HL130856-01A1 awarded by the U.S. National Institutes of Health (NIH). The government has certain rights in the invention.

REFERENCE TO A SEQUENCE LISTING SUBMITTED AS AN XML FILE VIA PATENT CENTER

The official copy of the sequence listing is submitted electronically via Patent Center as an XML formatted sequence listing with a file named SEQ_WFIRM_17_908.xml, created on Jul. 6, 2023, and having a size of 132 KB. The sequence listing contained in this XML formatted document is part of the specification and is herein incorporated by reference in its entirety.

BACKGROUND

Factor VIII is an essential blood clotting factor. The protein circulates in the bloodstream in an inactive form, bound to another molecule called von Willebrand factor, until an injury that damages blood vessels occurs. In response to injury, coagulation factor VIII is activated and separates from von Willebrand factor. The active protein interacts with another coagulation factor called Factor IX. This interaction sets off a chain of additional chemical reactions that form a blood clot.

Hemophilia A (HA) is the most common inheritable coagulation deficiency, affecting 1 in 5000 boys, approximately 60% of whom present with the severe form of the disease. Mutations in the Factor VIII gene that result in decreased or defective Factor VIII protein give rise to HA, a recessive X-linked disorder. Individuals with severe HA experience recurrent hematomas of subcutaneous connective tissue/muscle, internal bleeding, and frequent hemarthrosis, leading to chronic debilitating arthropathies. Current treatment is frequent infusions of Factor VIII (plasma-derived or recombinant) to maintain hemostasis, which greatly improves quality of life for many HA patients. While current therapeutic products for HA offer reliable prophylactic and therapeutic efficacy, they are very expensive and do not cure the underlying disease, thus requiring administration for the entire life of the patient. In addition, more than 30% of patients with severe HA develop inhibitory antibodies to the infused Factor VIII therapeutic, placing them in danger of treatment failure. This is a significant and serious complication/challenge in the clinical management/treatment of HA. While protein-based immune tolerance induction (ITI) therapy has been used with some success in this patient group, its cost extends into the millions of dollars per patient, it is only effective in about 60% of patients, and its mechanism of action is largely unknown. These shortcomings with existing therapy for patients who develop inhibitors highlight the need for innovative approaches to surmount this immunological hurdle.

BRIEF SUMMARY

In one aspect, provided are methods of treating a subject diagnosed with hemophilia A, the method involving the steps of (a) modifying mesenchymal stem/stromal cells (MSC) to express high levels of Factor VIII protein thereby generating modified MSC, the MSC comprising bone-marrow MSC isolated from the subject; (b) generating an expanded modified MSC population by in vitro culturing the modified MSC; and (c) injecting MSC from the expanded modified MSC population into the subject.

In another aspect, provided are methods of treating a subject prenatally diagnosed as having hemophilia A, the method involving the steps of (a) modifying mesenchymal stem/stromal cells (MSC) to express high levels of Factor VIII protein thereby generating modified MSC, the MSC comprising MSC isolated from at least one of amniotic fluid, placental tissue, or umbilical cord tissue obtained at the time of the subject's birth or prenatally from the subject's mother; (b) generating an expanded modified MSC population by in vitro culturing the modified MSC; and (c) injecting MSC from the expanded modified MSC population into the subject.

The above described and many other features and attendant advantages of embodiments of the present disclosure will become apparent and further understood by reference to the following detailed description when considered in conjunction with the accompanying drawings.

BRIEF DESCRIPTION OF THE DRAWINGS

These figures are intended to be illustrative, not limiting. Although the aspects of the disclosure are generally described in the context of these figures, it should be understood that it is not intended to limit the scope of the disclosure to these particular aspects.

FIG. 5 shows endogenous expression of Factor VIII in MSC isolated from amniotic fluid according to some aspects of the disclosure.

FIG. 6 shows endogenous expression of vWF in MSC isolated from amniotic fluid according to some aspects of the disclosure.

FIG. 7 shows exogenous expression of Factor VIII in MSC isolated from amniotic fluid and transduced with a lentivector encoding Factor VIII according to some aspects of the disclosure.

FIG. 8A shows assessment of phenotypic markers in PLCs according to some aspects of the disclosure.

FIG. 8B shows flow cytometric analysis of PLC constitutively expressed levels of FVIII protein according to some aspects of the disclosure.

FIG. 8C shows assessment of normalized levels of PLC constitutively expressed levels of FVIII protein according to some aspects of the disclosure.

DETAILED DESCRIPTION

Figure 1:
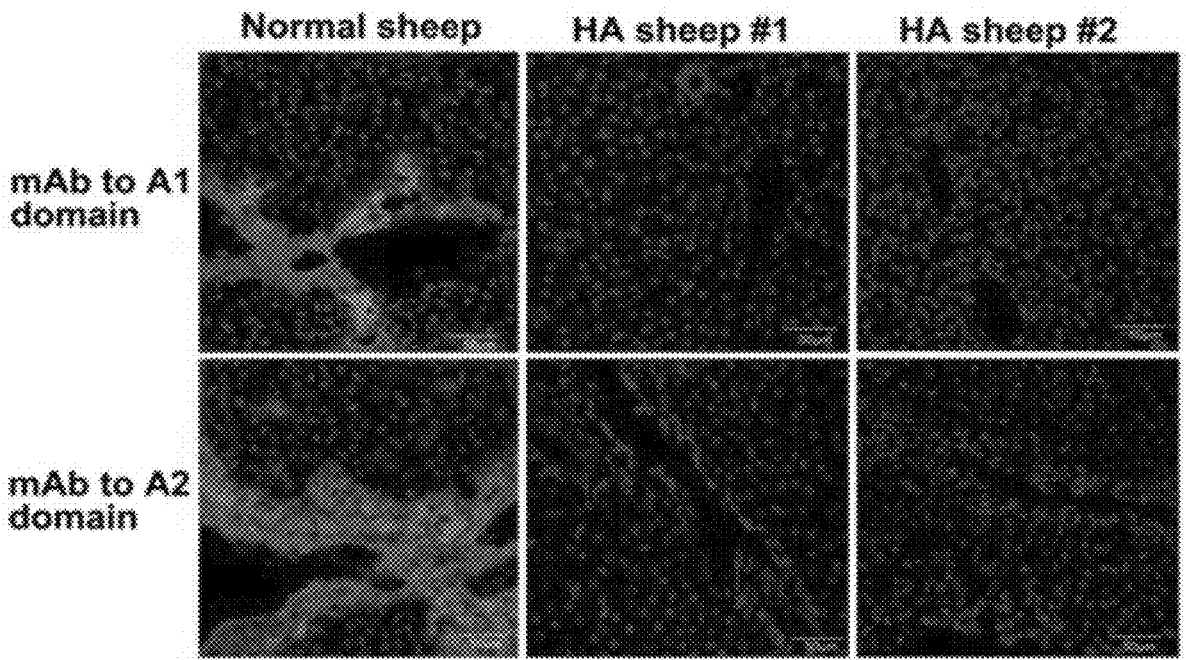
FIG. 1 shows the complete absence of any FVIII antigen/cross-reactive material (CRM) in the hemophilia A sheep according to some aspects of the disclosure.

Provided in this disclosure are methods of treatment for subjects having hemophilia A. The methods are post-natal therapies comprising administering to a subject with hemophilia A autologous mesenchymal stem/stromal cells (MSC) that have been modified to express Factor VIII. Provided methods are effective as first-line therapies for subjects that have been diagnosed prenatally or at an early age and who have not received Factor VIII therapy. Provided methods are also effective as second-line therapies for the treatment of subjects that have been receiving Factor VIII therapy and, in some instances, have developed an immune response to standard infusion therapy of exogenous Factor VIII. The MSC used in the methods are isolated from biological samples obtained prenatally or after the subject's birth. The MSC are modified to express high levels of Factor VIII protein. In some instances, the MSC are modified to express high levels of Factor VIII and high levels of another protein, such as von Willebrand factor. The MSC may be modified by the introduction of a transgene (for example, using a viral vector) or via genome-editing (for example, using the CRISPR/Cas9 system). Administering the modified MSC to the subject results in engraftment of the modified cells. The engrafted cells produce Factor VIII on a continuing basis in the subject and provide long-lasting (ideally lifelong) therapeutic benefit to the subject by promoting blood coagulation.

In one aspect, provided is a method of treating a subject diagnosed clinically or genetically with hemophilia A comprising: (a) modifying mesenchymal stem/stromal cells (MSC) to express high levels of Factor VIII protein thereby generating modified MSC, the MSC comprising bone marrow MSC isolated from the subject; (b) generating an expanded modified MSC population by in vitro culturing the modified MSC; and (c) injecting MSC from the expanded modified MSC population into the subject. The bone marrow MSC express at least one of Stro-1 or CD146. In some instances, the bone marrow MSC may be isolated based on expression of at least one of Stro-1 or CD146.

In another aspect, provided is a method of treating a subject prenatally diagnosed as having hemophilia A comprising: (a) modifying mesenchymal stem/stromal cells (MSC) to express high levels of Factor VIII protein thereby generating modified MSC, the MSC comprising MSC isolated from at least one of amniotic fluid, placental tissue, or umbilical cord tissue obtained at the time of the subject's birth or prenatally; (b) generating an expanded modified MSC population by in vitro culturing the modified MSC; and (c) injecting MSC from the expanded modified MSC population into the subject. In some instances, the MSC are amniotic fluid MSC. In some instances, the MSC are placental MSC (PLC). In some instances, the MSC are umbilical cord tissue MSC.

As used herein the terms treatment, treat, or treating refer to a method of reducing one or more symptoms of a disease or condition. In some instances, treatment results in a 5%, 10%, 20%, 30%, 40%, 50%, 60%, 70%, 80%, 90%, or 100% reduction in the severity of one or more symptoms of the disease or condition. In some instances, treatment results in at least a 60%, 65%, 70%, 75%, 80%, 85%, 90%, or 95% reduction in the severity of one or more symptoms of the disease or condition. In some instances, treatment results in a 100% reduction in the severity of one or more symptoms of the disease or condition. For example, a method for treating a disease is considered to be a treatment if there is a 5% reduction in one or more symptoms or signs. As used herein, control refers to the untreated condition. In some instances, the reduction can be a 5%, 10%, 20%, 30%, 40%, 50%, 60%, 70%, 80%, 90%, 100%, or any percent reduction in between 10% and 100% as compared to native or control levels. In some instances, the reduction can be at least a 65%, 70%, 75%, 80%, 85%, 90%, or 95% reduction as compared to native or control levels. In some instances, the reduction can be a 100% reduction. It is understood that treatment does not necessarily refer to a cure or complete ablation of the disease, condition, or symptoms of the disease or condition. As used herein, references to decreasing, reducing, or inhibiting include a change of 5%, 10%, 20%, 30%, 40%, 50%, 60%, 70%, 80%, 90% or greater as compared to a control level. Such terms can include, but do not necessarily include, complete elimination.

The subject on which the method is performed has been diagnosed with hemophilia A. The subject is mammalian, including humans; non-human primates, such as apes and monkeys; cattle; horses; sheep; rats; dogs; cats; mice; pigs; and goats. In some embodiments, the subject is a human, a dog, a horse, a sheep, a cow, or a cat. The subject may be male or female. The subject may be a juvenile subject or an adult subject. As a recessive X-linked disorder, a male subject will carry an X chromosome that has a mutation in the Factor VIII gene. A female subject that has hemophilia A will either have a mutated Factor VIII allele on both X chromosomes or will have a mutant Factor VIII allele on one X chromosome and have an inactive Factor VIII allele on the other X chromosome. In some instances, the subject may be a female carrier of hemophilia A that has a mutant Factor VIII allele on one X chromosome and a normal Factor VIII gene on the other X chromosome. Subjects may be diagnosed via prenatal genetic testing, particularly in instances where there is a family history of hemophilia. The DNA from biological samples obtained from amniocentesis, chorionic villi sampling, or cell-free fetal DNA present in the maternal peripheral blood may be analyzed for abnormalities on the X chromosome or mutations in the Factor VIII gene. Alternatively, subjects may be diagnosed after birth by assessing the ability of the subject's blood to clot properly. For example, screening tests include activated partial thromboplastin time (APTT) test, prothrombin time (PT) test, and fibrinogen test. Diagnosis of hemophilia A (type and severity) can also be performed with antigen-based tests that assess the amount of Factor VIII protein in the subject's blood. In some instances, the subject may have received therapy with infused Factor VIII protein. Where the subject has received such therapy, in some instances the subject may have developed an immune response to Factor VIII protein (developed inhibitory antibodies that impair the effectiveness of the therapy). In some embodiments, the subject has received prior treatment with exogenous Factor VIII and has developed an inhibitory immune response that diminishes the effectiveness of the exogenous Factor VIII treatment.

MSC, referred to in the field as mesenchymal stem cells, mesenchymal stromal cells, and, when isolated from bone marrow, also marrow stromal progenitors (MSP), are multipotent stromal cells that can differentiate into a variety of cell types, including: osteoblasts, chondrocytes, myocytes, and adipocytes. MSC do not have the capacity to reconstitute an entire organ. The term encompasses multipotent cells derived from other non-marrow tissues, such as placenta, umbilical cord blood, adipose tissue, or the dental pulp of deciduous baby teeth. MSC are heterogeneous and different subsets of MSC may have different capabilities. Different methods of isolation will result in different populations of MSC. Such different populations may express different protein markers. MSC subpopulations with different marker expression profiles have been found to have different capabilities. See, for example, Thierry, D., et al., Stro-1 Positive and Stro-1 Negative Human Mesenchymal Stem Cells Express Different Levels of Immunosuppression, Blood 104(11): 4964 (2004). The extent to which a MSC population isolated using one method and having a particular marker profile will share properties with a MSC population isolated using a different method and having a different marker profile has not been determined.

In some instances, the MSC used in the method are bone marrow-derived MSC—that is, the MSC are isolated from bone marrow. Specifically, the bone marrow-derived MSC are isolated from bone marrow obtained from the subject (autologous MSC). In some instances, the bone marrow-derived MSC used in the method express Stro-1, CD146, or both Stro-1 and CD146. Flow cytometry methods may be used to isolate MSC expressing these markers such as described, for example, in Sanada C., et al., Mesenchymal stem cells contribute to endogenous FVIII:c production. J Cell Physiol. 2013; 228(5):1010-1016 and Chamberlain J. L., et al., Efficient generation of human hepatocytes by the intrahepatic delivery of clonal human mesenchymal stem cells in fetal sheep. Hepatology. 2007; 46(6):1935-1945. Isolating MSC based on Stro-1 and/or CD146 results in a distinct cell population from that isolated using the traditional approach in which bulk unpurified bone marrow or Ficoll-purified bone marrow mononuclear cells are plated directly into plastic cell culture plates or flasks to which the adherent MSC population binds.

In some instances, the MSC used in the method are MSC isolated from a birth tissue or birth fluid. Specifically, the MSC may be isolated from amniotic fluid, placental tissue, chorionic villi, or umbilical cord tissue. In some instances, the MSC used in the method express c-kit. Methods of isolating such cells are described in U.S. Pat. Nos. 7,968,336 and 8,021,876, which are incorporated herein by reference in their entirety. In some instances, the MSC express at least one of c-kit, CD34, CD90, or CD133. In some instances, the MSC express c-kit and at least one of CD34, CD90, or CD133. In some instances, the MSC are isolated based on expression of c-kit.

For juvenile patients for whom prenatal biological samples are available, the MSC may be isolated from such samples (such as amniotic fluid, placental, cord tissue). Such samples may be available where the subject is diagnosed with hemophilia prior to birth. In some instances, appropriate biological samples may be obtained at the time of the subject's birth (such as amniotic fluid, placental, cord tissue). For adult patients, or juvenile patients for which prenatal biological samples are not available, the MSC used in the method may be bone marrow derived mesenchymal stem/stromal cells (MSC), also referred to as bone marrow stromal cells.

The MSC used in the method are modified to express high levels of Factor VIII. In some instances, the MSC may be modified to also express high levels of von Willebrand factor (vWF).

In some instances, an exogenous gene sequence encoding one or both of these proteins may be introduced into the MSC via one or more vectors. In some instances, the MSC may be modified to express high levels of Factor VIII protein via introduction into the MSC of a vector comprising a Factor VIII gene sequence operatively linked to a constitutively active promoter. In some instances, the MSC may be modified to express high levels of vWF protein via introduction into the MSC of a vector comprising a vWF gene sequence operatively linked to a constitutively active promoter. In some instances, the MSC may be modified to express high levels of Factor VIII protein and vWF protein via introduction into the MSC of a vector comprising a Factor VIII gene sequence operatively linked to a constitutively active promoter and a vector encoding a vWF gene sequence operatively linked to a constitutively active promoter. In some instances, the Factor VIII gene sequence and the vWF gene sequence may be operatively linked to the same constitutively active promoter. Alternatively, the Factor VIII gene sequence and the vWF gene sequence may be operatively linked to different constitutively active promoters.

Exemplary vectors include, for example, plasmids and viral vectors (including but not limited to adenoviral, adeno-associated viral (AAV), or retroviruses such as lentiviruses. In preferred embodiments, the vector is a viral vector. In some instances, the vector may be a vector that integrates into the genome of transduced cells. For example, the vector may be a lentivirus vector. In preferred embodiments, the vector is a lentivirus vector. In some instances, the lentivirus vector contains a 3'-modified long terminal repeat (LTR), resulting in a self-inactivating (SIN) lentivector. A lentivirus vector may integrate into the genome of dividing or non-dividing cells. The lentivirus genome in the form of RNA is reverse-transcribed to DNA when the virus enters the cell, and is then inserted into the genome by the viral integrase enzyme. The lentivirus vector, now called a provirus, remains in the genome and is passed on to the progeny of the cell when it divides. In another example, the vector may be an adeno-associated virus (AAV) vector, which, in contrast to wild-type AAV, only rarely integrates into the genome of the cells it transduces. In one example, the vector may be an adenoviral vector. An adenoviral vector does not integrate into the genome. In another instance, the vector may be a murine retrovirus vector. In another example, the vector may be a foamy virus vector, which may have a larger capacity for inserts than lentiviral vectors. In another example, the vector may be Sendai virus vector.

The exogenous gene sequences are operatively linked to one or more promoter sequences within the vector. The term "promoter sequence" or "promoter element" refers to a nucleotide sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for a gene therapy vector is derived from the native gene of the target protein (e.g., a Factor VIII promoter). In some embodiments, the promoter is a constitutive promoter, which drives substantially constant expression of protein from the exogenous gene sequence. Non-limiting examples of well-characterized promoter elements include the cytomegalovirus immediate-early promoter (CMV), the β-actin promoter, the methyl CpG binding protein 2 (MeCP2) promoter, the simian virus 40 early (SV40) promoter, human Ubiquitin C promoter (UBC), human elongation factor 1α promoter (EF1α), the phosphoglycerate kinase 1 promoter (PGK), or the CMV immediate early enhancer/chicken beta actin (CAG) promoter. The vector will generally also contain one or more of a promoter regulatory region (e.g., one conferring constitutive expression), a transcription initiation start site, a ribosome binding site, an RNA processing signal, a transcription termination site, and/or a polyadenylation signal.

In some instances, the Factor VIII transgene is operably linked to a promoter. A number of promoters can be used in the practice of the invention. The promoters can be selected based on desired outcome. The nucleic acids can be combined with constitutive, inducible, tissue-preferred, or other promoters for expression in the organism of interest. See, for example, promoters set forth as SEQ ID NOs: 1-6 as described in Brown et al. (2018) Target-Cell-Directed Bioengineering Approaches for Gene Therapy of Hemophilia A. *Mol. Ther. Methods Clin. Dev.,* 2018. 9:57-69, which is herein incorporated by reference in its entirety for all purposes.

Where the MSC are modified to express high levels of Factor VIII via transduction with an exogenous Factor VIII gene sequence, the exogenous Factor VIII gene sequence may be human Factor VIII gene sequence, porcine Factor VIII gene sequence, or a hybrid transgene comprising portions of human Factor VIII gene sequence and portions of porcine Factor VIII gene sequence. In some instances, the gene sequence comprises all or a portion of the human Factor cDNA as set forth in GenBank Accession No. 192448441 as updated Jul. 17, 2017, wherein said portion would encode a function portion of the human Factor VIII protein. In some instances, the gene sequence comprises a sequence that is at least 99%, 98%, 97%, 96%, 95%, 94%, 93%, 92%, 90%, 89%, 88%, 87%, 86%, 85%, 84%, 83%, 82%, 81%, or 80% identical to all or a portion of the human Factor cDNA as set forth in GenBank Accession No. 192448441 as updated Jul. 17, 2017, wherein said portion would encode a functional portion of the human Factor VIII protein. In some instances, the gene sequence may encode all or a functional portion of the human Factor VIII protein as set forth in GenBank Accession No. 192448441 as updated Jul. 17, 2017, reflecting the protein transcribed from transcript variant 1 of the Factor VIII gene. This protein is approximately 300 kDa and contains a series of homology-defined domains designated A1-A2-B-ap-A3-$C_1$-$C_2$. In some instances, the exogenous Factor VIII gene sequence is modified relative to wild-type protein sequence to result in increased protein expression, increased protein stability, reduced immunogenicity, or a combination of one or more thereof.

In some instances, the sequence of one or more of the Factor VIII protein domains may be deleted. In one example, the B domain of Factor VIII is deleted. The B domain of Factor VIII has no known function and can be deleted without loss of coagulant activity. Deletion of the B-domain has been shown to increase factor VIII protein production in heterologous systems (Toole et al. (1986) *Proc. Natl. Acad. Sci. U.S.A.* 83:5939-5942). In addition, wildtype porcine Factor VIII protein having the B-domain deleted may have 10-100-fold higher expression and secretion than the human Factor FVIII gene sequence, both in vitro and in vivo. (See, for example, Dooriss, K. L., et al., Comparison of factor VIII transgenes bioengineered for improved expression in gene therapy of hemophilia A. Hum Gene Ther. 20:465-478 (2009). A B-domain deleted form of human Factor VIII protein (Lind et al. (1995) *Eur. J. Biochem.* 232:19-27) has been approved for clinical use.

In some instances, the exogenous Factor VIII gene sequence may include protein modifications to reduce immunogenicity of the protein thereby reducing the risk of an immune response due to therapy. For example, alanine substitutions may be included as described in Healey, J. F., et al., The comparative immunogenicity of human and porcine factor VIII in haemophilia A mice. Thromb Haemost. 102:35-41 (2009) and Lubin, I. M., et al., Analysis of the human factor VIII A2 inhibitor epitope by alanine scanning mutagenesis. J Biol Chem. 272:30191-30195 (1997), which are incorporated by reference herein in their entirety.

In some instances, one or more of the human Factor VIII protein domain sequences may be substituted with the sequence of the corresponding porcine Factor VIII protein domain sequences. For example, one or more porcine Factor VIII domains may be substituted for one or more human Factor VIII domains. For example, inclusion of the porcine Factor VIII domains A1 and ap-A3 may increase expression of the expressed Factor VIII protein. See, for example, Doering, C. B., et al., Identification of porcine coagulation factor VIII domains responsible for high level expression via enhanced secretion. J Biol Chem. 279:6546-6552 (2004). In some embodiments, the exogenous Factor VIII gene sequence may comprise the human Factor VIII A2 and C2 domains and the porcine Factor VIII A1, A3, and C1 domains.

In some instances, the exogenous Factor VIII gene sequence may comprise a modified Factor VIII sequence comprising a B domain-deleted (BDD) Factor VIII transgene having the sequence of the human A2 and C2 domains and the porcine A1, A3, and C1 domains, and also include three alanine substitutions in the A2 domain to reduce immunogenicity, as described in Lubin, I. M., et al., Analysis of the human factor VIII A2 inhibitor epitope by alanine scanning mutagenesis. J Biol Chem. 1997; 272(48):30191-5. This modified Factor VIII protein is referred to as the ET3 transgene in this disclosure, including in the Examples below. In some instances, the ET3 transgene is expressed at a comparable level to that of wild-type porcine Factor VIII protein while having 91% identity to the amino acid sequence of wild-type human Factor VIII protein. In one example, the exogenous Factor VIII gene sequence may comprise a human/porcine Factor VIII transgene as described in Doering, C. B., et al., Directed engineering of a high-expression chimeric transgene as a strategy for gene therapy of hemophilia A, Mol. Ther. 17(7):1145-1154 (2009), which is incorporated herein by reference in its entirety.

In some instances, the Factor VIII transgene sequence may comprise one of the modified Factor VIII sequences described in Brown et al. (2018) Target-Cell-Directed Bioengineering Approaches for Gene Therapy of Hemophilia A. *Mol. Ther. Methods Clin. Dev.,* 2018. 9:57-69, which is incorporated herein by reference in its entirety for all purposes. Factor VIII polypeptides, including tissue-specific codon optimized variants, are described therein. Modified Factor VIII transgene sequences used in the methods described herein can be any one of SEQ ID NOs: 7-16 (as described in Brown et al.). For example, Factor VIII transgene sequences that can be used in the methods described herein include a B-domain deleted (BDD) human Factor VIII polypeptide (HSQ) as set forth in SEQ ID NO: 15, a BDD chimeric human/porcine Factor VIII polypeptide (ET3) as set forth in SEQ ID NO: 11, or an ancestral Factor VIII polypeptide (An53) as set forth in SEQ ID NO: 7.

sequences described in U.S. Pat. No. 7,635,763, which is incorporated herein by reference in its entirety for all purposes. Regions of the porcine Factor VIII polypeptide that comprises the A1 and ap-A3 regions, and variants and fragments thereof, are described therein that impart high-level expression to both the porcine and human Factor VIII polypeptide. The exogenous Factor VIII gene sequence encoded by the viral vector of the provided methods may be the polynucleotides set forth in any one of SEQ ID NOs: 19, 21, 23, 25, or 27 (SEQ ID NOs: 15, 17, 19, 13, or 21 as described in U.S. Pat. No. 7,635,763). The modified Factor VIII protein expressed at high levels in the modified MSC may comprise the amino acid sequences set forth in any one of SEQ ID NOs: 18, 20, 22, 24, or 26 (SEQ ID NOs: 14, 16, 18, 12, or 20 as described in U.S. Pat. No. 7,635,763). Such sequences are summarized in Table 1 below. In some instances, these sequences may be used to construct an exogenous Factor VIII gene sequence encoding a modified factor VIII polypeptide that results in a high level of expression of the encoded modified Factor VIII protein.

TABLE 1

| Exemplary Modified Factor VIII Proteins | | |
|---|---|---|
| Modified Factor VIII Protein | SEQ ID NO. | Description |
| HP44/OL | aa: SEQ ID NO: 18<br>nt: SEQ ID NO: 19 | $A1_P$-$A2_P$-$ap_P$-$A3_P$-$C1_H$-$C2_H$<br>porcine A1, A2, ap-A3 domains, porcine-derived linker sequence S F A Q N S R P P S A S A P K P P V L R R H Q R (SEQ ID NO: 30), and human C1 and C2 domains |
| HP46/SQ | aa: SEQ ID NO: 20<br>nt: SEQ ID NO: 21 | $A1_P$-$A2_H$-$ap_H$-$A3_H$-$C1_H$-$C2_H$<br>porcine A1 domain, human A2, ap-A3, C1 and C2 domains, and human S F S Q N P P V L K R H Q R linker sequence |
| HP47/OL | aa: SEQ ID NO: 22<br>nt: SEQ ID NO: 23 | $A1_P$-$A2_H$-$ap_P$-$A3_P$-$C1_H$-$C2_H$<br>porcine A1, ap-A3 domains, porcine-derived linker sequence S F A Q N S R P P S A S A P K P P V L R R H Q R (SEQ ID NO: 31), and human A2, C1 and C2 domains |
| B-domain deleted | aa: SEQ ID NO: 24<br>nt: SEQ ID NO: 25 | Human Factor VIII protein sequence minus B-domain |
| HP63/OL | aa: SEQ ID NO: 26<br>nt: SEQ ID NO: 27 | porcine A1 domain and a partially humanized ap-A3 domain that comprises porcine amino acids from about 1690 to about 1804 and from about 1819 to about 2019 |

In some instances, the exogenous Factor VIII gene sequence may be modified for expression in a particular organ or tissue type. For example, the gene sequence may be optimized for expression in myeloid tissue. In some embodiments, the Factor VIII transgene may comprise myeloid codon optimized ET3 (mcoET3) as set forth in SEQ ID NO: 12 or myeloid codon optimized HSQ (mcoHSQ) as set forth in SEQ ID NO: 16. Alternatively, the Factor VIII transgene may be optimized for expression in liver tissue. In some embodiments, the Factor VIII transgene may comprise liver codon optimized ET3 (lcoET3) as set forth in SEQ ID NO: 10; liver codon optimized An53 as set forth in SEQ ID NO: 8; or liver codon optimized (lcoHSQ) as set forth in SEQ ID NO: 14.

In some instances, the exogenous Factor VIII gene sequence may comprise one of the modified Factor VIII As discussed above, in some instances, the MSC are also modified to express high levels of vWF protein via introduction into the MSC of a vector. In some embodiments coding sequences for vWF can be any one of SEQ ID NOs: 28 or 29. In some instances, the vWF gene sequence in the vector may encode all or a functional portion of the human vWF protein set forth in GenBank Accession No. 1023301060 as updated Aug. 21, 2017. However, in some instances, the vWF gene sequence may include one or more modifications to the wild-type vWF gene sequence to increase protein expression, increase protein stability, reduce immunogenicity, or a combination of one or more thereof, of the vWF protein. For example, the full cDNA sequence of the vWF gene may be too large to be packaged efficiently in certain vectors, such as, for example, a lentiviral vector. Thus, in some instances, one or more exons of the vWF gene may be deleted while still retaining biological function of the expressed protein. In some instances, exons 24-46 of the vWF gene may be deleted as described in U.S. Patent Application Publication No. 2010/0183556. In some instances, the vWF gene sequence may be codon-optimized for efficient expression in the MSC. In some instances, the exogenous vWF gene sequence may modified for expression in a particular organ or tissue type. For example, the gene sequence may be optimized for expression in the liver. Thus, in some instances, the vWF gene sequence may comprise at least 99%, 98%, 97%, 96%, 95%, 94%, 93%, 92%, 90%, 89% 88%, 87%, 86%, 85%, 84%, 83%, 82%, 81%, or 80% identity to the corresponding wild-type vWF gene sequence and comprise modifications to improve expression. In some instances, the vWF gene sequence comprises the truncated human vWF sequence set forth below in this disclosure or a sequence at least 99%, 98%, 97%, 96%, 95%, 94%, 93%, 92%, 90%, 89% 88%, 87%, 86%, 85%, 84%, 83%, 82%, 81%, or 80% identical thereto while retaining biological activity of the expressed protein. In some instances, the vWF gene sequence comprises the truncated sheep vWF sequence set forth below in this disclosure or a sequence at least 99%, 98%, 97%, 96%, 95%, 94%, 93%, 92%, 90%, 89% 88%, 87%, 86%, 85%, 84%, 83%, 82%, 81%, or 80% identical thereto while retaining biological activity of the expressed protein.

In some instances, gene-editing may be performed on the MSC to insert, delete, or replace the genomic sequence of one or both of the endogenous genes using engineered nucleases (molecular scissors). Gene-editing nucleases belong to one of three known categories: zinc-finger nucleases (ZFN), transcription activator-like effector nucleases (TALEN), and clustered regularly interspaced short palindromic repeats (CRISPR) and their associated proteins (Cas) tools. All operate on the same principle; they are all capable of inducing a double-strand break at a defined genomic sequence that is subsequently corrected by endogenous DNA repair mechanisms. Double-strand breaks can be repaired through homology-driven repair (HDR), in the presence of donor homologous DNA sequences, resulting in gene-editing events.

In some instances, the MSC may be modified to express high levels of the Factor VIII protein via gene-editing of an endogenous Factor VIII gene sequence of the MSC, wherein the gene-editing introduces one or more modifications to an endogenous Factor VIII gene sequence that increase protein expression, increase protein stability, reduce immunogenicity, or a combination of one or more thereof, of the Factor VIII protein. In some instances, the MSC are modified to express high levels of an exogenous FVIII protein via genome-editing, wherein the gene-editing introduces an exogenous FVIII gene, under the control of a constitutive promoter, into a "safe harbor" region within the genome, such as the AAVS1 site. In some instances, the MSC are modified to express high levels of the vWF protein via gene-editing of an endogenous vWF gene sequence of the MSC, wherein the gene editing introduces one or more modifications to the endogenous vWF gene sequence that increase protein expression, increase protein stability, reduce immunogenicity, or a combination of one or more thereof, of the vWF protein. In some instances, the MSC are modified to express high levels of an exogenous vWF protein via genome-editing, wherein the gene-editing introduces an exogenous vWF gene, under the control of a constitutive promoter, into a "safe harbor" within the genome, such as the AAVS1 site. Exemplary "safe harbor" regions are described in Cerbini, T., et al., Transfection, selection, and colony-picking of human induced pluripotent stem cells TALEN-targeted with a GFP gene into the AAVS1 safe harbor. J Vis Exp. 2015 Feb. 1; (96):52504 and Hong, S. G., et al., Rhesus iPSC Safe Harbor Gene-Editing Platform for Stable Expression of Transgenes in Differentiated Cells of All Germ Layers. Mol Ther. 2017; 25(1):44-53.

In some instances, the endogenous Factor VIII gene sequence may be modified by gene-editing to have the type of modifications described above for embodiments where an exogenous Factor VIII gene sequence is introduced via transduction. The discussion of the various modifications described above is thus also applicable to embodiments where the endogenous Factor VIII gene sequence is modified. For example, in some instances, the sequence of one or more protein domains of the endogenous Factor VIII gene sequence may be deleted. In some instances, the B domain of Factor VIII is deleted. In some instances, the endogenous Factor VIII gene sequence may be modified to reduce immunogenicity of the protein thereby reducing the risk of an immune response due to therapy. For example, alanine substitutions may be introduced as described in Healey, J. F., et al., The comparative immunogenicity of human and porcine factor VIII in haemophilia A mice. Thromb Haemost. 102:35-41 (2009) and Lubin, I. M., et al., Analysis of the human factor VIII A2 inhibitor epitope by alanine scanning mutagenesis. J Biol Chem. 272:30191-30195 (1997), which are incorporated by reference herein in their entirety.

In some instances, the endogenous Factor VIII gene sequence may be modified to substitute one or more of the Factor VIII protein domain sequences with the sequence of the corresponding Factor VIII protein domain sequences from another species. For example, for human subjects, the endogenous Factor VIII gene sequence may be modified to substitute one or more of the human Factor VIII protein domain sequences with the sequence of the corresponding porcine Factor VIII protein domain sequences. For example, substitution with the porcine Factor VIII domains A1 and ap-A3 may increase expression of the expressed Factor VIII protein. See, for example, Doering, C. B., et al., Identification of porcine coagulation factor VIII domains responsible for high level expression via enhanced secretion. J Biol Chem. 279:6546-6552 (2004). In some embodiments, the endogenous Factor VIII gene sequence may be modified to comprise the porcine Factor VIII A1, A3, and C1 domains, while retaining the human Factor VIII A2 and C2 domains.

In some instances, the endogenous Factor VIII gene sequence may be modified to include a B domain deletion, the porcine A1, A3, and C1 domains, and also include three alanine substitutions in the A2 domain to reduce immunogenicity, as described above for the exogenous Factor VIII gene sequence embodiments. In one example, the endogenous Factor VIII gene sequence may be modified to have the sequence of a human/porcine Factor VIII transgene as described in Doering, C. B., et al., Directed engineering of a high-expression chimeric transgene as a strategy for gene therapy of hemophilia A, Mol. Ther. 17(7):1145-1154 (2009), which is incorporated herein by reference in its entirety. In some instances, the modified endogenous Factor VIII gene sequence results in expression of a modified Factor VIII protein at a level comparable to that of wild-type porcine Factor VIII protein while having 91% identity to the amino acid sequence of wild-type human Factor VIII protein.

In some instances, the endogenous Factor VIII gene sequence may be modified to comprise one of the modified Factor VIII sequences described in U.S. Pat. No. 7,635,763, which is incorporated herein by reference in its entirety for all purposes. In some instances, the endogenous Factor VIII gene sequence may comprise the polynucleotides set forth in any one of SEQ ID NOs: 19, 21, 23, 25, or 27 (SEQ ID NOs: 15, 17, 19, 13, or 21 as described in U.S. Pat. No. 7,635, 763). The modified Factor VIII protein expressed at high levels in the modified MSC may comprise the amino acid sequences set forth in any one of SEQ ID NOs: 18, 20, 22, 24, or 26 (SEQ ID NOs: 14, 16, 18, 12, or 20 as described in U.S. Pat. No. 7,635,763). Such sequences are summarized in Table 1 above.

As discussed above, in some instances, the MSC are also modified to express high levels of vWF protein via gene-editing. In some instances, the vWF gene sequence may include one or more modifications to the wild-type vWF gene sequence to increase protein expression, increase protein stability, reduce immunogenicity, or a combination of one or more thereof, of the vWF protein. For example, in some instances, one or more exons of the vWF gene may be deleted while still retaining biological function of the expressed protein. In some instances, exons 24-46 of the vWF gene may be deleted as described in U.S. Patent Application Publication No. 2010/0183556. In some instances, the vWF gene sequence may be codon-optimized for efficient expression in the MSC. In some instances, the exogenous vWF gene sequence may modified for expression in a particular organ or tissue type. For example, the gene sequence may be optimized for expression in the liver. Thus, in some instances, the vWF gene sequence may be modified to comprise at least 99%, 98%, 97%, 96%, 95%, 94%, 93%, 92%, 90%, 89% 88%, 87%, 86%, 85%, 84%, 83%, 82%, 81%, or 80% identity to the corresponding wild-type vWF gene sequence and comprise modifications to improve expression. In some instances, the vWF gene sequence may be modified to comprise the truncated human vWF sequence set forth below in this disclosure or a sequence at least 99%, 98%, 97%, 96%, 95%, 94%, 93%, 92%, 90%, 89% 88%, 87%, 86%, 85%, 84%, 83%, 82%, 81%, or 80% identical thereto while retaining biological activity of the expressed protein. In some instances, the vWF gene sequence may be modified to comprise the truncated sheep vWF sequence set forth below in this disclosure or a sequence at least 99%, 98%, 97%, 96%, 95%, 94%, 93%, 92%, 90%, 89% 88%, 87%, 86%, 85%, 84%, 83%, 82%, 81%, or 80% identical thereto while retaining biological activity of the expressed protein.

Where the MSC are modified to express high levels of both Factor VIII and vWF, the same method of modification may be used to achieve high expression of both proteins or different methods could be used for each protein. For example, in some instances, the MSC may be modified to express high levels of both Factor VIII and vWF protein via introduction of exogenous gene sequences for both proteins. In another example, the MSC may be modified to express high levels of both Factor VIII and vWF protein via gene-editing of the endogenous gene sequences of both proteins. In some instances, the MSC may be modified to express high levels of Factor VIII via transduction of an exogenous Factor VIII gene sequence and modified to express high levels of vWF via gene-editing of the endogenous vWF gene sequences. In other instances, the MSC may be modified to express high levels of vWF via transduction of an exogenous vWF gene sequence and modified to express high levels of Factor VIII via gene-editing of the endogenous Factor VIII gene sequences.

A "high level of expression" means that the production/expression of the modified Factor VIII protein or vWF protein is at an increased level as compared to the expression level of the corresponding native Factor VIII protein or vWF protein expressed under the same conditions. An increase in protein expression levels (considered a high level of expression) comprises at least about 0.5, 1, 2, 3, 4, 5, 6, 7, 8, 9, 10, 11, 12, 13, 14, 15, 20-fold or greater expression of the modified Factor VIII protein or vWF protein compared to the expression levels of the corresponding Factor VIII protein or vWF protein. Alternatively, "high-level expression" can comprise an increase in protein expression levels of at least 1-25 fold, 1-5 fold, 5-10 fold, 10-15 fold, 15-20 fold, 20-25 fold or greater expression levels of the modified Factor VIII protein or vWF protein when compared to the corresponding Factor VIII protein or vWF protein. Methods for assaying protein expression levels are routine in the art. By "corresponding" Factor VIII protein or vWF protein is intended a Factor VIII protein or vWF protein that comprises an equivalent amino acid sequence. In one example, expression of a modified human Factor VIII protein comprising the A1-A2-ap-A3-$C_1$-$C_2$ domains is compared to a human Factor VIII protein containing corresponding domains A1-A2-ap-A3-$C_1$-$C_2$. In another example, for a fragment of a modified human Factor VIII protein containing domains A1-A2-ap-A3, expression is compared to a fragment of human Factor VIII protein having the corresponding domains A1-A2-ap-A3. Alternatively, in certain instances, expression of a modified Factor VIII protein or vWF protein may be compared to the full-length corresponding proteins. In one example, for a fragment of a modified human Factor VIII protein containing domains A1-A2-ap-A3, expression is compared to human Factor VIII protein having the A1-A2-ap-A3-$C_1$-$C_2$ domains.

The modified MSC are cultured in vitro to generate an expanded modified MSC population. The expanded modified MSC population provides sufficient numbers of modified MSC for therapeutic use. Culture conditions may be selected based on the type of MSC used in the method. For example, MSC isolated from placental tissue may be grown in culture medium optimized for placental cells. In another example, MSC isolated from amnion tissue may be grown in culture medium optimized for amniotic cells. In another example, MSC isolated from umbilical cord or bone marrow may be grown in culture medium optimized for MSC cells. The modified cells may be grown on plastic culture dishes for at least 2, 3, 4, 5, or 6 passages to generate the expanded modified MSC population. In some instances, all or a portion of the expanded modified MSC population may be cryopreserved.

Following culturing of the modified MSC to generate expanded modified MSC population, modified MSC from expanded modified MSC population are injected into the subject. The injection may be made at least one of intraperitoneal injection, intravenous injection, or intra-articular injection. Each injection comprises about $10^5$ to about $10^9$ MSC from the expanded modified MSC population per kilogram weight of the subject. For example, the injection may comprise $10^5$ MSC, $10^6$ MSC, $10^7$ MSC, $10^8$ MSC, or $10^9$ MSC. The number of cells injected into the subject is based on the amount of protein expressed per cell. This metric is determined empirically for the expanded modified MSC population. In some instances, this metric may be generally predictable based on the nature of the modified MSC (for example, method of modification, Factor VIII gene sequence, vWF gene sequence, vector and vector components).

In some instances, modified MSC are injected into the subject once, twice, 3 times, 4 times, 5 times, 6 times, 7 times, 8 times, 9 times, or 10 times. In some instances, modified MSC are injected into the subject at least once, at least twice, at least 3 times, at least 4 times, at least 5 times, at least 6 times, at least 7 times, at least 8 times, at least 9 times, or at least 10 times. For example, the modified MSC may injected as multiple injections on the same day. In some instances, the modified MSC may be injected into the subject on multiple days. In some instances, the subject is injected with modified MSC on a first day and then the subject may be monitored over a period of time (days or weeks) to determine if there is sufficient protein expression to provide the desired therapeutic benefit. In some instances, the amount of protein expression in the subject's blood of Factor VIII protein, vWF protein, or both, may be monitored. In some instances, the efficiency of the subject's blood to clot may be assessed using routine blood clotting tests known in the art. In some instances, the subject's symptoms relating to joint pain and/or inflammation may be assessed. Where monitoring indicates that the amount of expression of Factor VIII protein alone, or the amount of expression of Factor VIII protein and vWF protein, is insufficient, the subject's disease symptoms are not alleviated, or both, the subject may be injected with modified MSC on a second day. Again, the subject may be monitored over a period of time to determine if there is sufficient protein expression to provide the desired therapeutic benefit. These steps may be repeated for a fourth, fifth, sixth, seventh, eighth, ninth, or tenth injection as needed to achieve the desired therapeutic benefit of alleviating the subject's disease symptoms.

In some instances, the use of MSC as cellular vehicles to deliver a Factor VIII gene sequence, a vWF gene sequence, or both, to a subject (as opposed to administration of vector directly) may overcome limitations/risks observed to-date in AAV-based clinical trials for hemophilia: 1) the possibility of off-target transduction of troubling cell types, such as germline cells; 2) the inability to treat patients with pre-existing antibodies to the serotype of AAV being employed as a vector; and 3) the transient hepatotoxicity induced by the AAV capsid, that triggers subsequent immune/inflammatory destruction of many of the transduced cells. Although early studies in vitro and in normal and hemophilia A mice, have used unselected stromal cells (isolated based solely upon plastic adherence) as cellular vehicles for delivering exogenous Factor VIII, no attempts have yet been made to use phenotypically-defined MSC/pericytes to deliver FVIII in vivo in any preclinical model of hemophilia A.

In some instances, the use of MSC as cellular vehicles to deliver a therapeutic gene is also an improvement over the use of hematopoietic stem cells (HSC), as have been used in most cell-based gene therapy trials. The use of MSC eliminates the possibility of insertional leukemogenesis, which is the most serious adverse event seen to-date in clinical gene therapy trials. A successful outcome of the proposed studies targeting hemophilia A thus promises to open the door to safe correction of a variety of congenital disorders using MSC to deliver the therapeutic gene.

EXAMPLES

Example 1. Animal Model

Applicant re-established a line of sheep that emulates the genetics, inhibitor formation, and clinical symptoms of the severe form of human hemophilia A (HA), including the development of frequent, spontaneous hematomas and crippling hemarthroses, making them unique among the HA models. See Porada, C. D., et al., Clinical and molecular characterization of a re-established line of sheep exhibiting hemophilia A. *J Thromb Haemost,* 2010. 8(2): 276-285. Using unique antibodies developed to various regions of the ovine FVIII protein, it was determined that these sheep do not produce any FVIII antigen (FIG. 1), as demonstrated by the complete lack of any staining within the liver of two of the HA sheep, which is in marked contrast to the widespread bright staining that is seen in the liver from a normal/healthy sheep. As such, they should be an excellent model of severe, cross-reacting material (CRM)-negative hemophilia A patients. Additionally, sheep are close in size to humans, their immune system is quite similar to that of humans, and their long lifespan allows long-term efficacy and safety to be addressed.

Example 2. Preliminary Pilot Study—Allogeneic Cells

A pilot study on 2 pediatric subjects from the HA sheep model described in Example 1. See Porada, et al., Phenotypic correction of hemophilia A in sheep by postnatal intraperitoneal transplantation of FVIII-expressing MSC. Exp Hematol, 2011. 39(12):1124-1135. During the first 3-5 months of life, both animals had received frequent, on-demand infusions of human FVIII (hFVIII) for multiple hematomas and chronic, progressive, debilitating hemarthroses of the leg joints which had resulted in severe defects in posture and gait, rendering them nearly immobile. Thus, for these subjects, FVIII was presented in the context of "danger signals", which is known to trigger a robust host immune response to FVIII and other proteins.

Haploidentical MSC from the ram that had sired the two HA lambs were used for the therapy. The MSC were modified to introduce via transduction a B domain-deleted, wild-type porcine FVIII cDNA as described in Porada et al., Phenotypic correction of hemophilia A in sheep by postnatal intraperitoneal transplantation of FVIII-expressing MSC. *Exp Hematol.* 2011; 39(12):1124-1135. MSC were simultaneously transduced with 2 lentivectors; one encoded eGFP for in vivo tracking of donor cells, and the second encoded an expression/secretion optimized porcine FVIII (pFVIII) transgene previously shown to be expressed/secreted from human cells at 10-100 times higher levels than hFVIII or sheep (ovine) FVIII (oFVIII). See Gangadharan et al., High-level expression of porcine factor VIII from genetically modified bone marrow-derived stem cells. *Blood,* 2006. 107(10):3859-64; Doering et al., Directed Engineering of a High-expression Chimeric Transgene as a Strategy for Gene Therapy of Hemophilia A. *Mol Ther,* 2009. 17(7): 1145-54; Doering et al., Identification of porcine coagulation factor VIII domains responsible for high level expression via enhanced secretion. *J Biol Chem,* 2004. 279(8): 6546-52; Dooriss et al., Comparison of Factor VIII Transgenes Bioengineered for Improved Expression in Gene Therapy of Hemophilia A. *Hum Gene Ther,* 2009. 20(5): 465-78; Ide, L. M., et al., Hematopoietic stem-cell gene therapy of hemophilia A incorporating a porcine factor VIII transgene and nonmyeloablative conditioning regimens. *Blood,* 2007. 110(8):2855-63; and Johnston et al., Generation of an optimized lentiviral vector encoding a high-expression factor VIII transgene for gene therapy of hemophilia A. *Gene Ther,* 2013. 20(6):607-15.

FVIII/GFP-expressing MSC were then expanded and transplanted by IP injection ($30 \times 10^6$), in the absence of any preconditioning, into the first lamb. Following transplant, this animal's clinical picture improved dramatically, and he enjoyed an event-free clinical course, devoid of spontaneous bleeds, obviating the need for hFVIII infusions. Even more remarkably, the animal's existing hemarthroses resolved, his joints recovered fully, and he regained normal posture and gait, resuming a normal activity level. To the inventors' knowledge, this represents the first report of phenotypic correction of severe HA in a large animal model following transplantation of cells modified to express FVIII, and is the first time that reversal of chronic debilitating hemarthroses has been achieved in any setting.

Based on this remarkable clinical improvement, the modified MSC were transplanted into the second animal using an identical procedure, but a higher cell dose ($125 \times 10^6$). In similarity to the first animal, hemarthroses present in this second animal at the time of transplant resolved, he resumed normal activity shortly after transplantation, and became factor-independent.

Interestingly, despite the marked phenotypic improvement in both these animals, no circulating FVIII activity was detectable following the transplant, most likely due to the presence of high-titer inhibitors in these animals. These findings are remarkable, since despite the high titers of antibodies/inhibitors present in these animals, the transplanted allogeneic (haploidentical) MSC persisted and were not eliminated by the recipient's immune system, and the therapeutic effect of the treatment was maintained, i.e., the animals' symptoms of spontaneous joint bleeds, hematomas, and bleeding upon needle stick all improved.

Example 3. Mechanistic Study—Autologous Cells

Twenty female HA carriers will be artificially inseminated (AI) via laparoscopy, as done in Example 2, with the support of the North Carolina State Theriogenology/Ruminant Medicine team. At 50-70 days of gestation (term: 150 days), amniotic fluid will be collected, and fetal cells from the amniotic fluid will be isolated, cultured, and expanded, using standard methods in our lab. Given the severe phenotype of these animals, we will perform a PCR-based RFLP (see Porada, C. D., et al., J Thromb Haemost, 2010. 8(2):276-85) to identify affected fetuses, allowing us to plan for their subsequent delivery. Following amniocentesis, the animals will be allowed to complete term. When the sheep have nearly completed gestation, the pregnant ewes carrying affected fetuses will be placed under close observation, and ewes will either be induced into labor using intramuscular dexamethasone for natural delivery, or the lambs will be delivered by Caesarian section, with clinical veterinarians assisting in either case. Both approaches have been used previously with success.

Affected lambs will be treated immediately with recombinant full-length or B-domain deleted ovine FVIII (oFVIII) produced as described in Zakas, P. M., et al., Development and characterization of recombinant ovine coagulation factor VIII. PLoS One, 2012. 7(11):e49481. Although we have found that oFVIII is not a very high-expressing FVIII variant when compared to FVIII from other species, oFVIII protein for transfusion and an oFVIII transgene in the vectors are being used because the consensus in the hemophilia field is that the use of "same-species" FVIII is essential in preclinical gene therapy-based studies to accurately model the potential immune response in the clinical arena.

While human cells may be needed to perform definitive clinical studies, human cells are not appropriate for these mechanistic studies because using human cells would not allow us to address the critical issue of whether the use of autologous cells results in higher levels of long-term engraftment than we achieved in our pilot study with allogeneic cells, and whether the use of autologous cells may reduce the incidence of inhibitor formation. For this reason, sheep MSC will be used throughout this study.

It is our goal to treat HA with this MSC-based delivery system during the first 18 months of postnatal human life, since this is the time by which most HA patients would be diagnosed. Sheep develop much faster than humans, and are weaned at 60-90 days of age. We thus know this corresponds to the first 12-18 months for a human, so we will test the MSC-based treatment during the first 2-3 months of life in the sheep.

Figure 2:
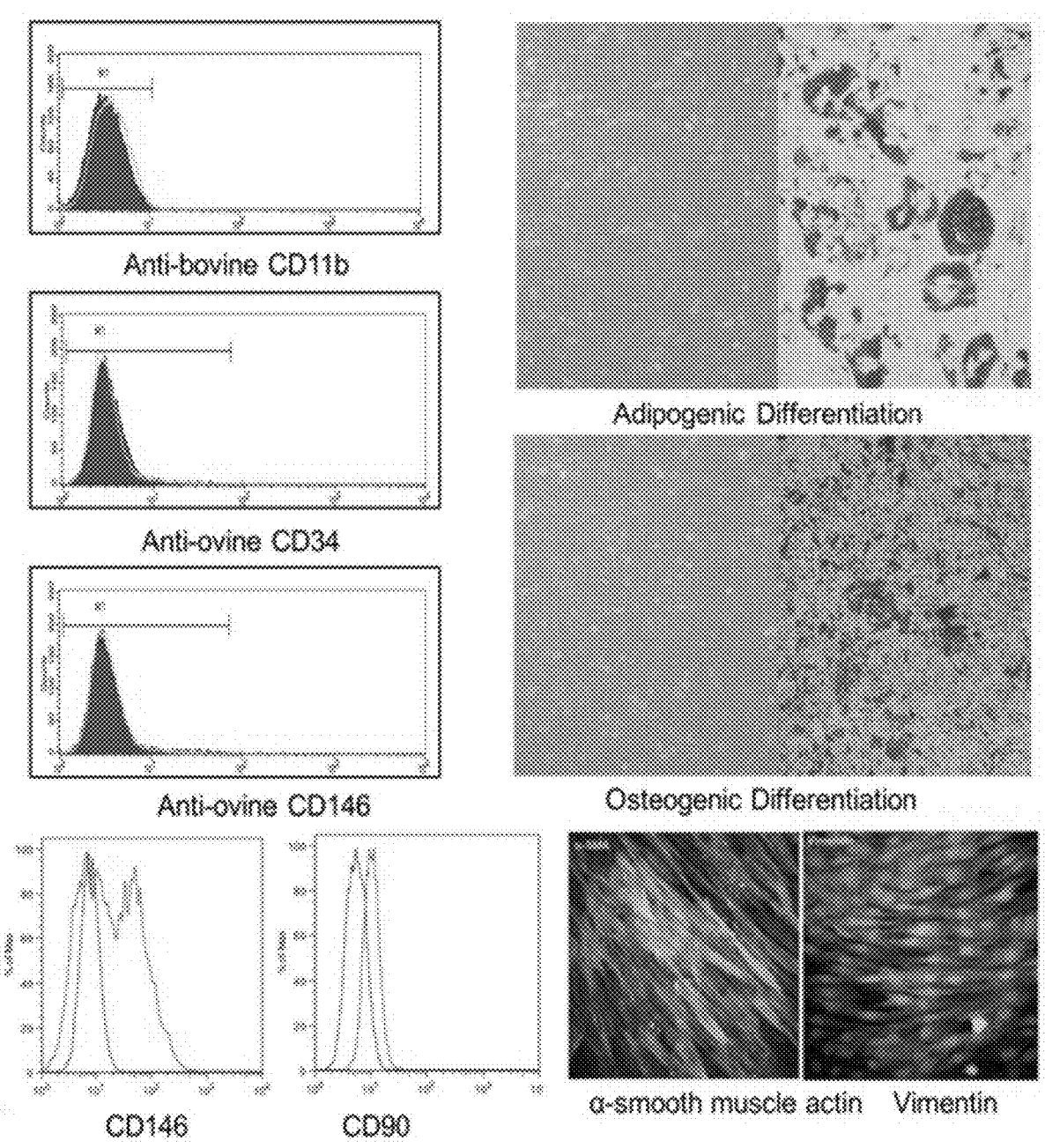
FIG. 2 shows assessment of phenotypic markers in MSC isolated from sheep according to some aspects of the disclosure.

Starting at birth, HA lambs will be treated prophylactically 2-3 times per week with recombinant oFVIII. At 4-5 weeks of age, we will collect bone marrow (under oFVIII coverage), and isolate MSC from each affected lamb, as we have done previously. These methods enable us to successfully establish primary sheep MSC that are phenotypically and functionally similar to their human counterparts; these sheep MSC are devoid of hematopoietic cells (they lack CD11b, CD34, and CD45), but they express the MSC markers CD146 and CD90. See FIG. 2. Anti-ovine antibodies to other antigens routinely used to identify MSC, such as CD44, CD105, and CD73, are not commercially available. Immunofluorescence microscopy demonstrated expression of vimentin and α-smooth muscle actin, known MSC cytoskeleton proteins, and we verified the ability of these sheep MSC were able to differentiate into adipocytes (by Oil-red-o staining) and osteocytes (by calcium deposition and alkaline phosphatase). See FIG. 2.

Figure 3:
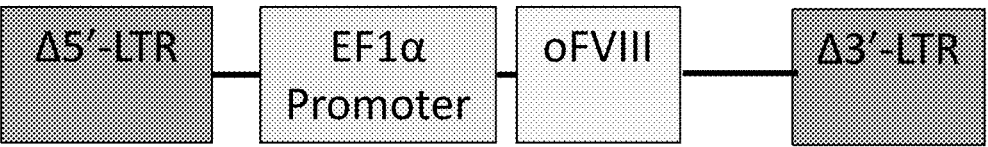
FIG. 3 shows a schematic diagram of an ovine Factor VIII transgene expression vector according to some aspects of the disclosure.
Figure 4:
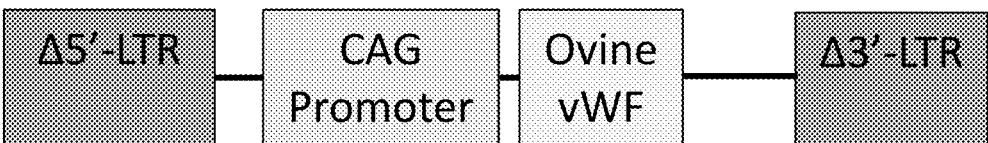
FIG. 4 shows a schematic diagram of an ovine vWF transgene expression vector according to some aspects of the disclosure.

We will then subject the isolated MSC to 2-3 rounds of transduction with either the EF1α-[oFVIII] lentivirus vector (FIG. 3) alone, or simultaneously with the EF1α-[oFVIII] lentivirus vector and the CAG-[vWF] lentivirus vector (FIG. 4). See De Meyer, S. F., et al., Phenotypic correction of von Willebrand disease type 3 blood-derived endothelial cells with lentiviral vectors expressing von Willebrand factor. Blood, 2006. 107(12): 4728-36. The EF1α-[oFVIII] lentivirus vector contains a B-domain deleted oFVIII gene having the polynucleotide sequence set forth in SEQ ID NO: 33. The CAG-[vWF] lentiviral vector contains a truncated vWF having the polynucleotide sequence set forth in SEQ ID NO: 29. From the pilot study described in Example 2, we know that 2-3 rounds of simultaneous exposure to two different lentivirus vectors results in transduction of 90-95% of sheep MSC with both vectors. The lentivirus vectors for these studies both contain the 3'-modified LTR to produce SIN lentivirus vectors, and the constitutive EF1α promoter will drive FVIII expression. Due to packaging constraints, it is not possible to utilize the EF1α promoter in the vWF lentivirus vector. Prior studies have established the ability of vWF to be packaged within a lentivirus vector and expressed at high levels. See De Meyer, S. F., et al., 2006 (above). However, if any difficulties arise packaging vWF-encoding lentivirus vectors, we will utilize truncated vWF cassettes as described in this disclosure, or switch to foamy virus vectors, as they possess a much larger packaging capacity.

We are including a group in which autologous MSC are transduced with vectors encoding both oFVIII and vWF (ovine vWF; GI:426227037) for two reasons: 1) binding to vWF stabilizes FVIII and prolongs its half-life and, thus, delivery of MSC secreting FVIII complexed with vWF may produce a more pronounced therapeutic effect; and 2) vWF may reduce the immunogenicity of exogenously administered FVIII by preventing both its uptake and presentation by dendritic cells, and its recognition by immune effector cells. We predict that delivering the two proteins in the same vector will result in the release of FVIII:vWF as a complex from the transduced MSC. We will confirm co-localization/complex formation of vector-derived oFVIII and vWF in transduced MSC populations by confocal microscopy prior to performing the proposed transplants. Although MSC do not endogenously produce any vWF, we will add a 6-His tag (SEQ ID NO:32) to the vWF transgene, making it readily distinguishable from any trace endogenous vWF for these in vitro studies.

Following transduction, the FVIII-expressing MSC will be expanded until the animals have reached 2-3 months of age, at which point the MSC be transplanted autologously into their respective donor HA lamb, via IP injection under ultrasound guidance, with no preconditioning (as in our pilot study [23]), using a dose of 5-10×10 6 cells/kg. An aliquot of each cell type will be reserved to determine vector copy number by qPCR and to perform integration site analysis by LM-PCR. Methods described in Porada, C. D., et al., *Phenotypic correction of hemophilia A in sheep by postnatal intraperitoneal transplantation of FVIII-expressing MSC.* Exp Hematol, 2011. 39(12):1124-1135 (qPCR) and Russo-Carbolante, E. M., et al., *Integration pattern of HIV-1 based lentiviral vector carrying recombinant coagulation factor VIII in Sk-Hep and 293T cells.* Biotechnol Lett, 2011. 33(1):23-31 and Tellez, J., et al., *High Incidence of Vector Integration Near Cancer Related Genes within Primitive Hematopoietic Stem Cells (HSC) After Fetal Gene Transfer with γ-Retroviral Vectors.* Molecular Therapy, 2010. 18(Suppl. 1): p. 5331 (LM-PCR). Two experimental groups will be included: 1) autologous MSC transduced with the EF1α-[oFVIII] lentivector (n=2-3 HA lambs); and 2) autologous MSC transduced with both the EF1α-[oFVIII] and CAG-vWF lentivectors (n=2-3 HA lambs).

Following transplantation, prophylactic oFVIII infusions will be discontinued, and any benefit as a result of this MSC-based approach should be readily apparent, given the severe, life-threatening phenotype of these animals. The sheep will be continually monitored for bleeds, and platelet-deficient plasma will be collected monthly until at least 1.5 years of age for coagulation assays, to quantify the plasma levels of oFVIII by chromogenic assay and/or ELISA. The formation/presence of inhibitors will be assessed at each time point by performing the Nijmegen modification of the Bethesda assay (as described in Verbruggen, B., et al., The Nijmegen modification of the Bethesda assay for factor VIII:C inhibitors: improved specificity and reliability. Thromb Haemost, 1995. 73(2):247-51) and a commercially available kit (Technoclone/DiaPharma Group, Inc.) on an aliquot of plasma collected from the animals. Once we have obtained these values, we will compare the HA lambs that received MSC transduced with the lentivector encoding oFVIII alone to those that received MSC transduced with both the oFVIII and vWF lentivectors, and compare each of these to the historic values from untransplanted HA sheep, and to a reference panel of normal unaffected males. These studies will allow us to: 1) establish what levels of vector-encoded oFVIII are expressed as a result of this postnatal approach; 2) determine the duration of the therapeutic effect of this approach; 3) assess whether using autologous MSC and a lentivector that lacks eGFP avoids the inhibitors seen in the pilot study of Example 2; and 4) establish whether including vWF improves the therapeutic effect of this MSC-based treatment and/or reduces the incidence/titer of inhibitor formation.

At 1.5 years of age (or sooner, if we see that FVIII levels are dropping), the HA lambs will be euthanized, and all major organs will be harvested. All tissues will be fixed in 4% paraformaldehyde, processed through a sucrose gradient, embedded and frozen in OCT, and sectioned at 5 μm. 8-10 slides/tissue will be stained with an antibody specific to oFVIII and analyzed/quantitated by confocal microscopy for the presence of engrafted MSC to precisely determine the levels and localization (parenchymal vs. perivascular) of engrafted cells that are expressing FVIII, and are therefore providing therapeutic benefit. We will also collect plasma from each of these recipients at the time of euthanasia, and quantitate the circulating levels of vector-derived oFVIII in these sheep using an ELISA specific for oFVIII, correlating levels and patterns of engraftment with circulating FVIII levels. Based on ease of access to the circulation, we hypothesize that maximal plasma FVIII levels will be obtained when MSC lodge in perivascular regions of the engrafted tissues.

While confocal analysis should provide us with a fairly accurate estimate of the levels of oFVIII+ MSC within each tissue, the slides selected for quantitation may or may not be representative of the engraftment levels within the organ as a whole. Therefore, we will also use an ELISA to precisely quantitate the amount of oFVIII within tissue homogenates. A standard curve will be created with known numbers of oFVIII+ MSC, thereby establishing how much oFVIII is present on a per-cell basis. Protein extracts will then be prepared from the tissues from each animal and analyzed using this ELISA, comparing the tissue values to that of the standard curve, to precisely quantitate the number of MSC that have engrafted within each tissue and are expressing oFVIII. We will then compare the levels of donor MSC in each tissue with the resultant plasma FVIII levels to determine in which tissues engraftment produces the highest circulating levels of FVIII.

Example 4. Study Assessing Treatment in Subjects with Pre-Existing Inhibitors The findings of the study described in Example 3 will be used to determine the ability of this autologous cell-based approach to mediate clinical/phenotypic improvement in recipients with pre-existing inhibitors as a result of on-demand FVIII treatment.

Three to four HA lambs will be treated on-demand with oFVIII beginning at birth. We expect, based on the pilot study of Example 2, that treating on-demand with FVIII products will result in the formation of inhibitors in almost all HA sheep by 4-5 months of age. We will collect bone marrow and isolate MSC at 4-5 weeks of age, and transduce these cells with either the EF1α-[oFVIII] lentivector alone, or with both the EF1α-[oFVIII] and CAG-vWF lentivectors (depending which approach yields the best outcome in the preceding studies), and expand the transduced cells to obtain adequate numbers for transplant.

Beginning at birth, we will draw blood from these animals every other week to obtain plasma and perform the Nijmegen modification of the Bethesda assay (as above) (Technoclone/DiaPharma Group, Inc.) to assess the development of inhibitors. Once inhibitors have developed, we will transplant the transduced autologous MSC into each animal by ultrasound-guided IP injection, as in Exp. Set #1.1, at a dose of 5-10×10⁶ cells/kg.

Following transplantation, we will analyze the animals as detailed in Example 3, continually monitoring them for bleeds, and collecting platelet-deficient plasma monthly until at least 1 year of age for coagulation assays, to quantify the plasma levels of oFVIII by chromogenic assay and/or ELISA, and to quantitate the levels of inhibitors present, to ascertain whether the MSC-based treatment impacts upon the levels of the pre-existing inhibitors. We will then compare the results obtained with these HA lambs with pre-existing inhibitors to those in Example 3 in which the HA lambs lacked inhibitors at the time of MSC infusion.

Example 5. First Line Therapy Study

We hypothesize that previously untreated patients (PUPS) represent the ideal group to initially target with this MSC-based treatment, because their immune systems are completely naïve to exogenous FVIII, and will be exposed to it for the first time when it is released by the transplanted MSC; we anticipate this will reduce/eliminate the risk of inhibitor formation in this population.

In families with no prior history, HA is normally diagnosed during the first 18 months of life, after the child exhibits abnormal bruising/bleeding after a minor trauma. In families with a history of HA, diagnosis can be made at birth, or even prior to birth [148-158]. Regardless of when diagnosis is made, however, it would not be possible to collect bone marrow MSC from these patients without treating with factor to prevent hemorrhage during the procedure. This same issue exists with the HA sheep, since they present with a severe phenotype and spontaneous bleeding from birth. However, in similarity to patients with a family history of HA, the affected sheep can be diagnosed in utero by amniocentesis (as can be done in human patients), making it possible to collect autologous cells from the amniotic fluid part way through gestation, transduce these cells, expand them, and have them ready to transplant as the first-line therapy at birth, or shortly thereafter. We recently found that MSC-like cells present within the amniotic fluid, "AF-MSC", are readily transduced with lentivirus vectors, they endogenously produce low levels of FVIII (FIG. 5) and vWF (FIG. 6), and they express very high levels of FVIII following lentivector transduction (FIG. 7). These findings suggest that amniotic fluid can replace marrow as a source of autologous MSC for delivering a FVIII transgene, enabling us to test the MSC-based treatment's efficacy as first-line therapy in PUPs.

To test the efficacy of the MSC-based treatment in PUPs, HA carrier ewes will be bred or artificially inseminated as detailed in Example 3. At 50-60 days of gestation (term: 150 days), amniotic fluid will be collected, AF-MSC isolated, and a PCR-based RFLP performed to detect the HA mutation, as detailed in Example 3. AF-MSC from the affected fetuses will then be subjected to 2-3 rounds of transduction with the EF1α-[oFVIII] comprising the polynucleotide sequence set forth in SEQ ID NO: 33 (FIG. 3) and expanded. At near term, labor will be induced in the ewes with affected lambs, or a C-section performed to deliver the lambs. Immediately after birth, the HA lamb "PUPs" (n=3-4) will be injected IP with the transduced autologous AF-MSC at a dose of 5-10×10$^6$ cells/kg, as described for the BM-MSC in Example 3.

Following transplantation, we will analyze the animals as detailed in Example 3 and 4, continually monitoring them for bleeds, and collecting platelet-deficient plasma monthly until at least 1 year of age for: 1) coagulation assays; 2) to quantify the plasma levels of oFVIII by chromogenic assay and/or ELISA; and 3) to perform the Nijmegen modified Bethesda assay to assess the development of inhibitors. We will then compare the results obtained by using this MSC-based treatment as a first-line therapy in these HA lamb "PUPS" to the results obtained in the HA lambs treated prophylactically (Example 3) and to those treated on-demand (Example 4) prior to MSC infusion.

Example 6. Study to Assess Induction of Immune Tolerance to Factor VIII

We hypothesize that the continued delivery of FVIII to the circulation by the lentivector-modified MSC can serve as a much-needed novel method of inducing immune tolerance to FVIII.

The aim of this study is to test the ability of this MSC-based approach as a novel method of inducing immune tolerance through the continued delivery of FVIII to the circulation by the genetically-modified MSC. To accomplish this objective, 2-3 HA lambs (more will be added if initial data are not clear-cut) will be treated on-demand with oFVIII, beginning at birth, as we know that treating on-demand with FVIII products results in the formation of inhibitors in almost all HA sheep by 4-5 months of age. As in Example 4, we will isolate BM-MSC at 4-5 weeks of age, and transduce these cells with both the EF1α-[oFVIII] and CAG-vWF lentivectors, as clinical data indicate that the inclusion/presence of vWF may facilitate ITI [123, 159, 160]. The transduced cells will then be expanded to obtain adequate numbers for subsequent transplant.

Beginning at birth, we will draw blood from these animals every other week to obtain plasma and perform the Nijmegen modified Bethesda assay (as above) to assess inhibitor induction. Once inhibitors have developed, we will transplant transduced autologous MSC, at a dose of 10' cells/kg, into the peritoneal cavity of each animal, as in Example 3. This procedure will be repeated each 4-5 days until we observe a drop in inhibitor titer (as detailed below); a maximum of 10 infusions will be given initially.

Following transplantation, we will analyze the animals as in Example 3, continually monitoring for bleeds (as the repeated MSC-based treatment should produce clinical/phenotypic improvement), and collecting platelet deficient plasma bi-weekly for ≥3 months, to perform coagulation assays, to quantify the oFVIII plasma levels by chromogenic assay and/or ELISA, and to quantitate the levels of inhibitors present, to ascertain whether the repeated infusion of MSC expressing high levels of FVIII can break the existing inhibitors and induce tolerance to FVIII. To further confirm that this cell-based ITI has overcome the existing inhibitors, we will assess the restoration of normal FVIII pharmacokinetics, using well-established methodology (plasma FVIII recovery ≥66% of expected and a ≥6 h half-life, determined following a 72-hour FVIII-exposure-free period).

Example 7. Comparison of Recombinant Factor VIII Infusion Therapy with MSC-Based Tolerance Induction One of the only clinical options for HA patients who develop inhibitors is immune tolerance induction (ITI), which involves the long—term administration of high doses of FVIII protein. ITI is extremely expensive, is only effective in a percentage of patients with inhibitors, and the mechanism for its success is unknown. To-date, no preclinical HA model has been used to study and/or optimize ITI. Given the high incidence of inhibitor formation in the HA sheep and their lack of any cross-reactive material, they represent an excellent model in which to investigate ITI. We propose to perform a head-to-head comparison of traditional ITI, using repeated high-dose recombinant oFVIII to the MSC-based ITI protocol developed/tested in Example 6.

To achieve these goals, 2-3 HA lambs will be treated on-demand with oFVIII, beginning at birth, as described in Example 6, until inhibitors develop. We will then commence a clinically employed, protein-based ITI regimen, infusing the inhibitor animals with a dose of 100 IU/kg/day for 3 months (as described in Oldenburg, J., et al., Primary and rescue immune tolerance induction in children and adults: a multicentre international study with a VWF-containing plasma-derived FVIII concentrate. Haemophilia, 2014. 20(1):83-91). During the course of this ITI protocol, we will analyze the animals as detailed in Example 6, collecting platelet-deficient plasma weekly, to: 1) perform coagulation assays; 2) quantify the plasma levels of oFVIII by chromogenic assay and/or ELISA; and 3) quantitate the levels of inhibitors present, to assess the ability of the protein-based ITI to break existing inhibitors, and define the kinetics with which this happens. To further confirm that ITI has overcome existing inhibitors, we will assess the restoration of normal FVIII pharmacokinetics, as detailed above. The success rate and kinetics of tolerance induction with the protein-based ITI will be compared to those of the cell-based protocol in Example 6, to determine whether the cell-based method is a viable alternative to the time consuming and expensive protein-based method that represents the current state-of-the-art in clinical ITI.

Example 8. Transduction Efficiency with Different Vectors

Figures 10A, 10B, 10C:
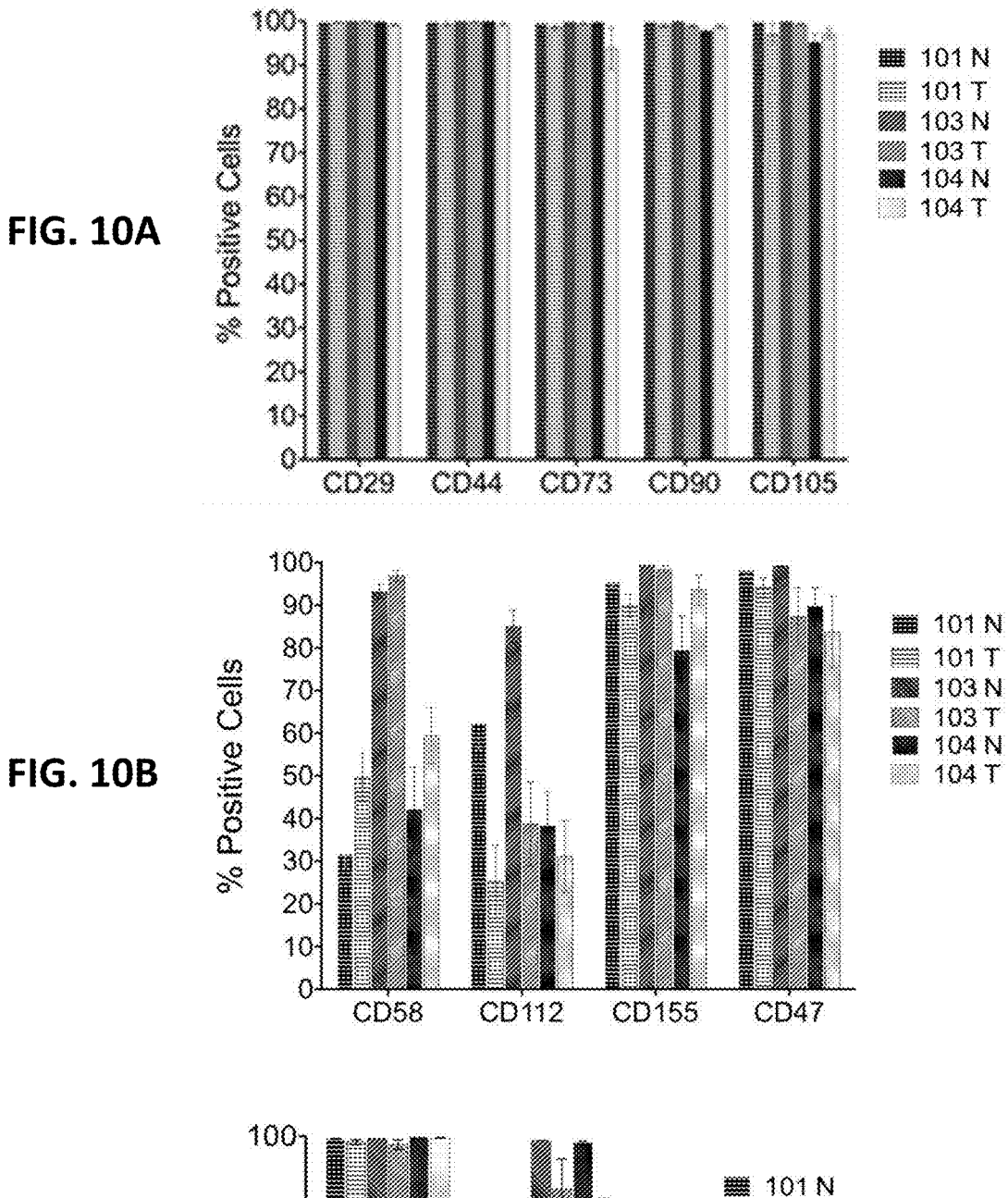
FIGS. 10A-10C show assessment of phenotypic markers in transduced as compared to non-transduced PLCs according to some aspects of the disclosure.

The transduction efficiency, FVIII production, and FVIII secretion from human PLC following transduction at an identical multiplicity of infection (MOI) of 7.5 with an identical lentiviral vector (LV) encoding one of the following four different FVIII transgenes: (1) a bioengineered human-porcine hybrid FVIII (ET3) having the polynucleotide sequence set forth in SEQ ID NO: 11; (2) a liver codon-optimized ET3 (lcoET3) having the polynucleotide sequence set forth in SEQ ID NO: 10; (3) a liver codon-optimized human FVIII (lcoHSQ) having the polynucleotide sequence set forth in SEQ ID NO: 14; and (4) a myeloid-codon optimized ET3 (mcoET3) having the polynucleotide sequence set forth in SEQ ID NO: 12 were compared. Brown et al. (2018) *Mol. Ther. Methods Clin. Dev.* 9:57-69, demonstrated that vectors encoding FVIII, when codon-optimized to the target cells, or tissue, result in a dramatically increase FVIII expression of functional FVIII. Following transduction, PLCs were analyzed by flow cytometry and confocal microscopy to measure transduction efficiency and FVIII production. Conditioned media of PLCs were assayed by aPTT to quantitate FVIII activity. Analysis of the culture supernatants by aPTT demonstrated FVIII activity was readily detectable in supernatants of all transduced cells lines. It also revealed marked differences in the secretion of functional FVIII following transduction with each of these vectors. Specifically, PLCs transduced with mcoET3 (SEQ ID NO: 12), ET3 (SEQ ID NO: 11), lcoET3 (SEQ ID NO: 10), and lcoHSQ (SEQ ID NO: 14) LV secreted 25±9, 19±8, 11±2, and 1±0.1 IU of FVIII/24 h/10^6 cells, respectively (FIG. 10). PLC population doubling time was not affected by transduction with any of the vectors; nor were phenotype or expression of signaling molecules involved in innate immunity. Importantly, at passage 3 following transduction with any of the 4 lentiviral vectors, PLCs continued to produce and secrete FVIII at similar levels to those observed shortly after transduction, demonstrating stable vector integration and durability/longevity of FVIII expression. The relative levels of FVIII expression by PLCs following transduction with each lentiviral vector were also assessed by immunofluorescence microscopy with an antibody specific to a region of FVIII that is conserved in all 4 FVIII transgenes. These analyses confirmed the results of the aPTT analyses on the supernatants from these cells, with mcoET3-PLC exhibiting the brightest/highest intensity staining for FVIII, followed by PLC transduced with ET3 (SEQ ID NO: 11), then those transduced with lcoET3 (SEQ ID NO: 10) and with lcoHSQ (SEQ ID NO: 14) (data not shown).

The gene transfer efficiency of these gene-modified cells was assessed by determining the final proviral/vector copy number (VCN) using a commercially available qPCR-based kit (Lenti-X Provirus Quantitation Kit, Takara Bio USA, Inc., Mountain View, CA). To ensure that only integrated copies were detected by the assay, qPCR for VCN was performed in PLCs that had been passaged at least three times after transduction. After transducing the cells at the same MOI (7.5) with each lentiviral vector, the VCNs for mcoET3-PLC, lcoHSQ-PLC, lcoET3-PLC, and ET3-PLC were all around 1.

Example 9. Optimizing Factor VIII Expression in Placental Cells

The aim of this study was to investigate the suitability of placental cells (PLC) as cellular delivery vehicles for FVIII. The expression of phenotypical markers was determined in three different master cells banks (101, 103, and 104) of placental cells (PLCs), each of which was derived from a different human donor by the Regenerative Medicine Clinical Core (RMCC) at WFIRM following GMP-compliant standard operating procedures (SOPs) established by the RMCC for PLC. Expression of CD29, CD44, CD73, CD90, CD105, HLA-ABC, HLA-E, CD31, CD34, CD35, CD144, HLA-G, HLA-DR/DP/DQ, and ABO blood group were determined using flow cytometric analysis. These markers were selected to confirm that the PLC isolated possessed a phenotype characteristic of MSC from other tissues (CD29, CD44, CD73, CD90, CD105), to assess their potential for stimulating an immune response upon transplantation (HLA-ABC, HLA-E, CD35, CD144, HLA-G, HLA-DR/DP/DQ, and ABO blood group), and to discern whether they expressed markers indicative of endothelial properties (CD31, CD34). No statistically significant differences (p<0.05) were found in expression of phenotypic markers between PLCs derived from three different master cell banks (101, 103, and 104). PLCs from each of the master cell banks expressed CD29, CD44, CD73, CD90, CD 105, HLA-ABC, and HLA-E (FIG. 8A); had negligible amounts (<1%) of CD31, CD34, CD35, CD144, HLA-G, and HLA-DR/DP/DQ (data not shown); and were devoid of ABO blood group (data not shown). Collectively, these findings support the conclusion that PLC are an MSC-like population and that they should exhibit minimal immunogenicity upon transplantation.

PLCs derived from each of the master cell banks [MCBs] (101, 103, and 104) were assessed for their ability to express FVIII protein constitutively. Immunofluorescence microscopy with a primary antibody specific to hFVIIIc and a fluorochrome-conjugated secondary antibody and flow cytometric analysis with fluorochrome-conjugated antibodies to were used to determine the levels of constitutively expressed FVIII protein and define the phenotype of the PLCs, respectively. As shown in FIG. 8A, these cells expressed markers characteristic of MSC from bone marrow and other tissues. All three MCBs endogenously expressed detectable amounts of FVIII by immunofluorescence microscopy, and MCB 103 expressed the highest levels, as indicated by the brightest fluorescence intensity (data not shown). The fold increase of FVIII expression over isotype control for PLCs derived from each of the MCBs is presented as relative mean fluorescence intensity (MFI) as shown in FIG. 8B.

The activated partial thromboplastin time (aPTT or PTT) assay is a functional measure of the intrinsic and common pathways of the coagulation cascade (i.e. it characterizes blood coagulation). The aPTT assay was used to quantitate levels of functional FVIII secreted by PLCs. PLCs were plated at the same density and cultured for 24 hours in Phenol Red-free alpha-MEM AmnioMax Complete Medium (ThermoFisher Scientific, Raleigh, NC). Supernatants were collected and the number of cells present counted, and then the levels of secreted functional FVIII were measured by the Clinical Hematology Laboratory at Wake Forest Baptist Health using a commercial aPTT assay. Levels of FVIII were normalized by adjusting to account for the number of cells present at the time of supernatant collection, and expressing FVIII activity on a per cell basis. The data from this analysis is shown in FIG. 8C FVIII mRNA levels in the PLCs derived from three different master cell banks (101, 103, and 104) were evaluated by qPCR using primers specific to human FVIII. Relative expression of endogenous mRNA for FVIII was calculated by comparing the threshold cycle (CT) value for FVIII with the CT of each master cell bank's respective internal reference gene, GAPDH. The relative expression of endogenous FVIII mRNA was $0.01\pm0.0005$, $0.075\pm0.007$, and $0.011\pm0.0002$, for PLCs 101, 103, and 104, respectively.

Example 10. Suitability of PLCs as a Transgenic FVIII Production Platform

Figure 9A:
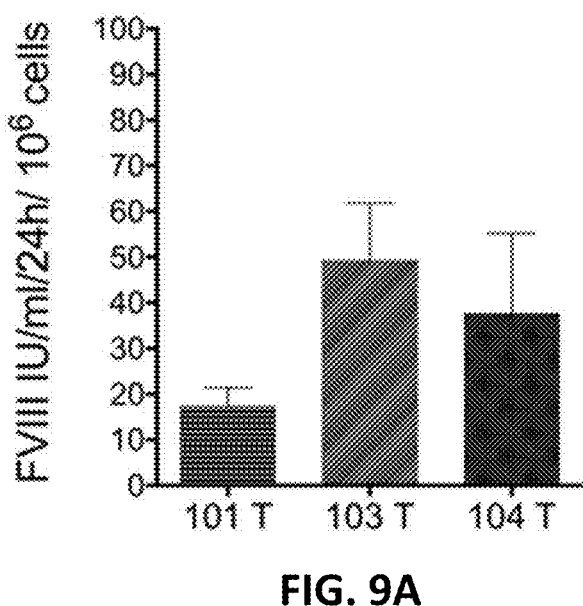
FIG. 9A shows assessment of normalized levels of secretion of FVIII protein by PLC engineered/transduced to express high levels of FVIII according to some aspects of the disclosure.
Figure 9B:
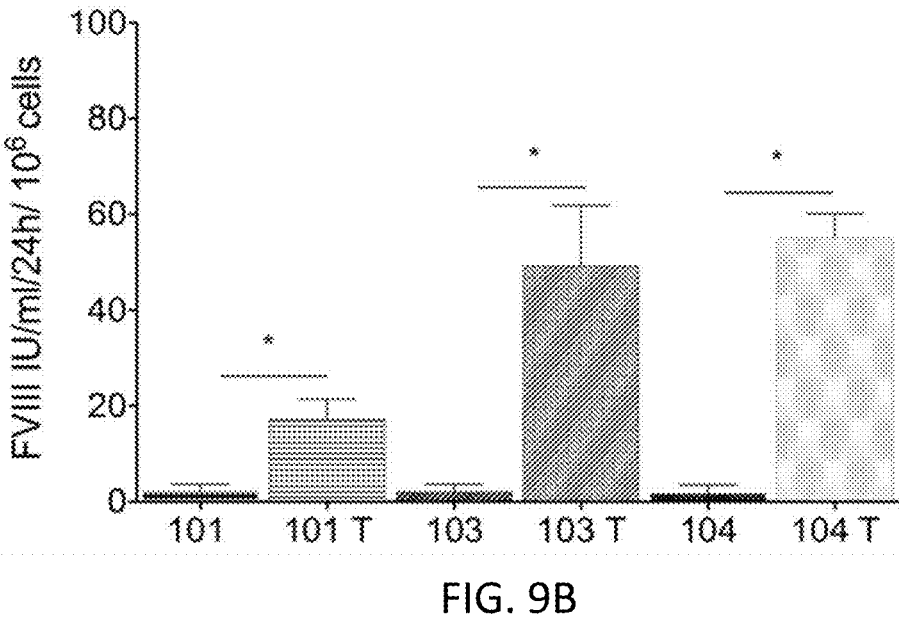
FIG. 9B shows assessment of secretion of FVIII protein by transduced as compared to non-transduced PLCs according to some aspects of the disclosure.

PLC 101, 103, and 104 were transduced at the same MOI (7.5) using a lentiviral vector-(LV) encoding mcoET3 (mcoET3-PLC) as described in Example 4 above. Vector copy number (VCN) was determined, as described in detail above. The VCN was found to be similar between the three different PLC MCBs (0.71-0.75). After transduction, the relative levels of expression of FVIII by the 3 MCB PLCs were assessed by immunofluorescence microscopy after staining with a primary antibody specific to hFVIIIc and a fluorochrome-conjugated secondary antibody. All 3 MCBs expressed high levels of FVIII after transduction with the mcoET3 lentiviral vector, but MCB 103 exhibited the highest levels of FVIII protein, as evidence by the brightest/highest fluorescence intensity (data not shown). The secretion of FVIII was determined using aPTT performed on 24-hour culture supernatants harvested from PLCs that were plated at the same density and normalized for the number of cells present at the time of the supernatant collection, as described in detail in the preceding paragraphs (FIG. 9A). Levels of FVIII in the culture supernatant increased significantly ($p<0.05$) in PLCs derived from all 3 MCBs (101, 103, and 104) when compared with respective non-transduced PLC counterparts (FIG. 9B). No significant differences were found between the different transduced cells.

The effect of transduction of PLCs with LV encoding mcoET3 on phenotype or molecules involved in immunity was assessed. Expression of CD29, CD44, CD73, CD90, CD 105, CD58, CD112, CD155, CD47, HLA-ABC, HLA-E, HLA-G, and HLA-DR/DP/DQ, were determined by flow cytometric analysis, as described above. No statistically significant differences ($p<0.05$) were found between transduced and non-transduced cells (FIGS. 8A-8C). Additionally, PLC population doubling time was not affected by transduction (data not shown). Both non-transduced and transduced PLCs expressed CD47, a molecule involved in immune evasion (FIG. 8B). Transduced cells did not significantly upregulate the expression of HLA-DR/DP/DQ (FIG. 8C).

Figure 11A:
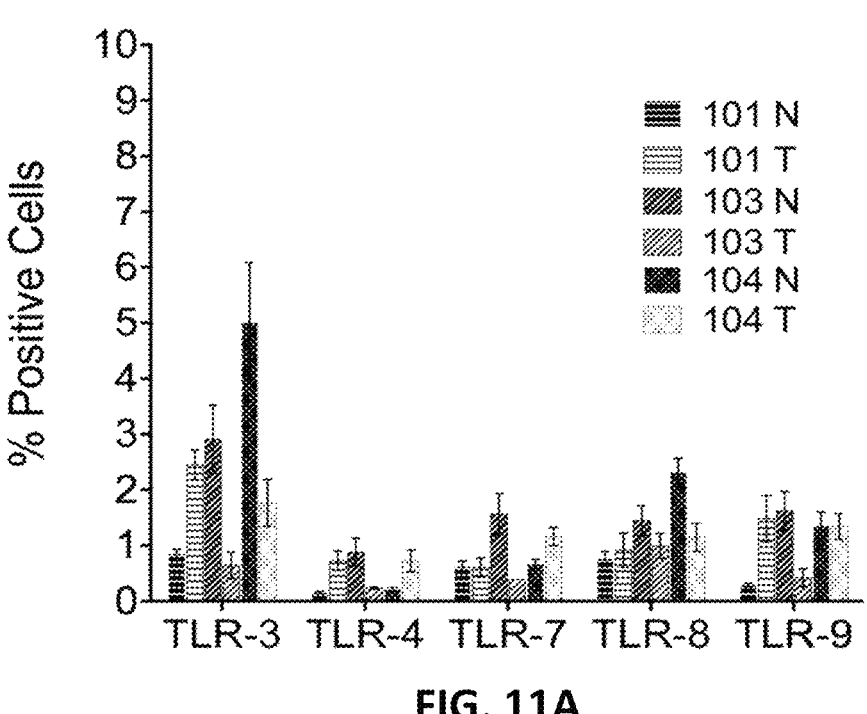
FIG. 11A shows assessment of expression of Toll-like receptors (TLRs) in mcoET3-transduced PLCs as compared to non-transduced PLCs according to some aspects of the disclosure.

To further examine whether transduction of the PLC with the mcoET3 lentiviral vector had the potential to alter the immunogenicity of these cells, we examined the levels of expression of various Toll-like Receptors (TLRs) on the PLC prior to and following transduction, as these molecules play a key role in innate immunity, and their upregulation could potentially trigger an immune response to the transduced cells upon transplantation. To address this possibility, the effect of PLC transduction with the mcoET3 lentiviral vector on TLR-3, TLR-4, TLR-7, TLR-8, and TLR-9 expression was assessed. TLR expression on transduced (t) and non-transduced (n) PLCs (101, 103, and 104) was determined using flow cytometric analysis. No significant differences in expression of TLR molecules was detected in the PLC populations. As shown in FIG. 11A, there was no difference in the levels of expression of any of these TLRs in transduced vs. non-transduced PLCs, confirming that transduction of these 3 MCB PLCs with the mcoET3 lentiviral vector did not lead to upregulation of any of these immune-stimulating molecules.

Figure 11B:
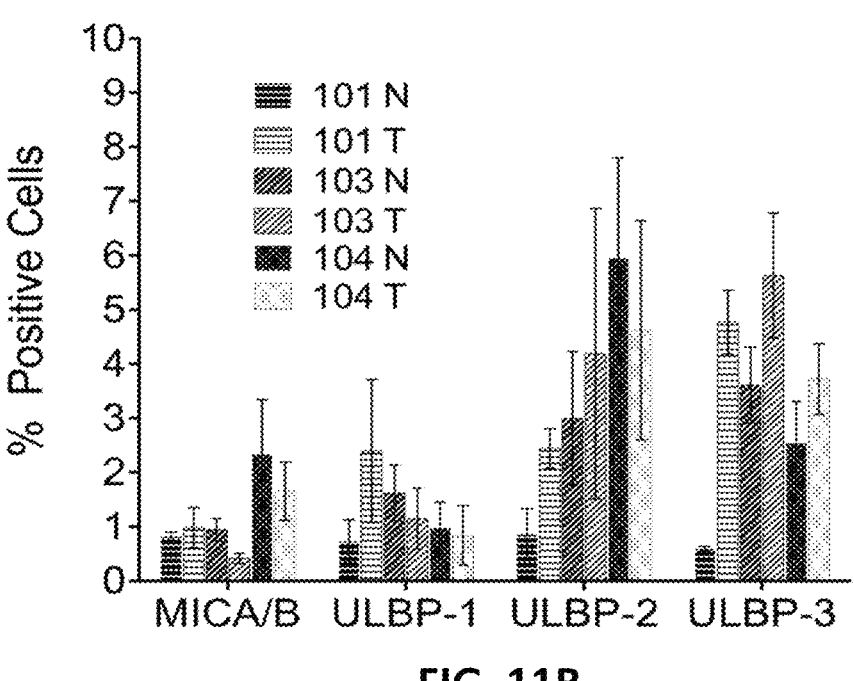
FIG. 11B shows assessment of expression of stress molecules in mcoET3-transduced PLCs as compared to non-transduced PLCs according to some aspects of the disclosure.
Figure 12:
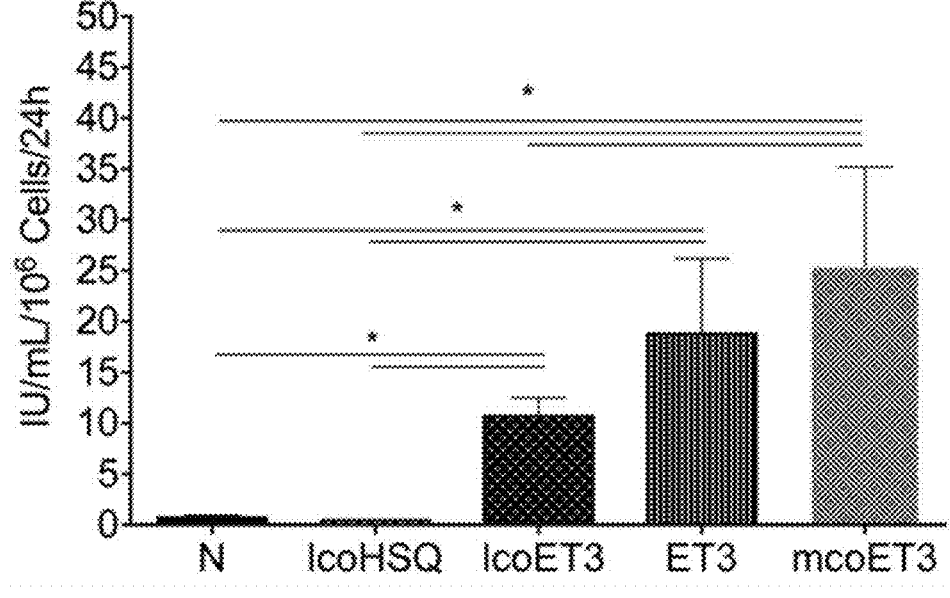
FIG. 12 shows assessment of normalized levels of PLC secretion of FVIII protein by non-transduced-PLC, lcoHSQ-PLC, lcoET3-PLC, ET3-PLC, and mcoET3-PLC according to some aspects of the disclosure.

In order to evaluate the demands of PLC transduction with mcoET3 and increased Factor VIII expression on the secretory and endoplasmic reticulum pathways, expression of stress molecules MICA/B, ULBP-1, ULBP-2, and ULBP-3 was determined in transduced (t) and non-transduced (n) PLCs (101, 103, and 104). Flow cytometric analysis demonstrated that no significant expression or alteration/upregulation of MICA/B or ULBP-1 were found before or after transduction with mcoET3 lentiviral vector (FIG. 11B).

The production of interferon-gamma (IFN-γ) by mcoET3 transduced and non-transduced PLCs was measured using a high-sensitivity ELISA (assay range: 0.16-10.0 pg/mL). PLCs were cultured for 24 hours in AmnioMax Complete Medium (ThermoFisher). Supernatants were collected and IFN-γ production was determined. No IFN-γ was detected in any of the culture supernatants of mcoET3-transduced or non-transduced PLCs (data not shown).

All features of the described systems are applicable to the described methods mutatis mutandis, and vice versa.

All patents, patent publications, patent applications, journal articles, books, technical references, and the like discussed in the instant disclosure are incorporated herein by reference in their entirety for all purposes.

It is to be understood that the figures and descriptions of the disclosure have been simplified to illustrate elements that are relevant for a clear understanding of the disclosure. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments, such substitution is considered within the scope of the disclosure.

The examples presented herein are intended to illustrate potential and specific implementations of the invention. It can be appreciated that the examples are intended primarily for purposes of illustration for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Aspects and embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A method of post-natally treating a subject diagnosed with hemophilia A, comprising:

(a) providing isolated c-kit⁺ mesenchymal stem/stromal cells (MSC), wherein the MSC have been isolated for positive expression of c-kit;

(b) modifying the isolated c-kit⁺ MSC of step (a) to express high levels of Factor VIII protein thereby generating modified MSC, wherein the modified MSC comprise at least one of modified amniotic fluid MSC, modified placental tissue MSC, or modified umbilical cord tissue MSC, wherein the isolated c-kit⁺ MSC are modified to comprise a codon-optimized Factor VIII gene sequence comprising one or more genetic modifications that increase Factor VIII protein expression, Factor VIII protein stability, or both, and wherein the Factor VIII protein comprises human Factor VIII A2 and C2 domains and porcine Factor VIII A1, A3, and C1 domains, and wherein the codon-optimized Factor VIII gene sequence comprises SEQ ID NO:12;

(c) generating an expanded modified MSC population by in vitro culturing the modified MSC; and (d) injecting the expanded modified MSC population into the subject.

2. The method of claim 1, wherein the subject has received prior treatment with exogenous Factor VIII and has developed an inhibitory immune response that diminishes effectiveness of the exogenous Factor VIII treatment.

3. A method of post-natally treating a subject prenatally diagnosed as having hemophilia A, comprising:

(a) providing isolated c-kit⁺ mesenchymal stem/stromal cells (MSC), wherein the MSC have been isolated for positive expression of c-kit, wherein the MSC are isolated from at least one of amniotic fluid, placental tissue, or umbilical cord tissue obtained at the subject's birth or prenatally from the subject's mother;

(b) modifying the isolated c-kit⁺ MSC of step (a) to express high levels of Factor VIII protein thereby generating modified c-kit⁺ MSC, wherein the modified c-kit⁺ MSC comprise a codon-optimized Factor VIII gene sequence comprising one or more genetic modifications that increase Factor VIII protein expression, Factor VIII protein stability, or both, and wherein the Factor VIII protein comprises human Factor VIII A2 and C2 domains and porcine Factor VIII A1, A3, and C1 domains, and wherein the codon-optimized Factor VIII gene sequence comprises SEQ ID NO:12;

(c) generating an expanded modified MSC population by in vitro culturing the modified MSC; and (d) injecting the expanded modified MSC population into the subject.

4. The method of claim 3, wherein the isolated MSC express CD90.

5. The method of claim 1, wherein the MSC are modified by introducing into the MSC:

a viral vector comprising the Factor VIII gene sequence operatively linked to a constitutively active promoter, at least two viral vectors, wherein a first viral vector comprises the Factor VIII gene sequence operatively linked to a constitutively active promoter and a second viral vector comprises a von Willebrand (vWF) gene sequence operatively linked to a constitutively active promoter, or a viral vector comprising the Factor VIII gene sequence operatively linked to a constitutively active promoter and a vWF gene sequence operatively linked to a constitutively active promoter.

6. The method of claim 5, wherein the MSC are modified by introducing into the MSC the viral vector comprising the Factor VIII gene sequence operatively linked to a first constitutively active promotor and a vWF gene sequence operatively linked to a second constitutively active promoter, wherein the Factor VIII gene sequence and the vWF gene sequence are operatively linked to the same constitutively active promoter.

7. The method of claim 1, wherein the MSC from the expanded modified MSC population are injected into the subject via at least one of intraperitoneal injection, intravenous injection, or intra-articular injection.

8. The method of claim 1, wherein the expanded modified MSC population are injected into the subject at least once, at least twice, or at least three times.

9. The method of claim 1, wherein the expanded modified MSC population are injected into the subject in an amount of about 107 to about 109 MSC per kilogram weight of the subject.

10. The method of claim 3, wherein the MSC are modified by introducing into the MSC a viral vector comprising the Factor VIII gene sequence operatively linked to a constitutively active promoter, at least two viral vectors, wherein a first viral vector comprises the Factor VIII gene sequence operatively linked to a constitutively active promoter and a second viral vector comprise a vWF gene sequence operatively linked to a constitutively active promoter, or a viral vector comprising the Factor VIII gene sequence operatively linked to a constitutively active promoter and a vWF gene sequence operatively linked to a constitutively active promoter.

11. The method of claim 10, wherein the MSC are modified by introducing into the MSC the viral vector comprising the Factor VIII gene sequence operatively linked to a first constitutively active promotor and a vWF gene sequence operatively linked to a second constitutively active promoter, wherein the Factor VIII gene sequence and the vWF gene sequence are operatively linked to the same constitutively active promoter.

12. The method of claim 3, wherein the MSC from the expanded modified MSC population are injected into the subject via at least one of intraperitoneal injection, intravenous injection, or intra-articular injection.

13. The method of claim 3, wherein the expanded modified MSC population are injected into the subject at least once, at least twice, or at least three times.

14. The method of claim 3, wherein the expanded modified MSC population are injected into the subject in an amount of about $10^7$ to about $10^9$ MSC per kilogram weight of the subject.

15. The method of claim 1, wherein the isolated MSC are allogeneic.

16. The method of claim 1, wherein the isolated MSC express CD47.

17. The method of claim 3, wherein the isolated MSC express CD47.

18. The method of claim 5, wherein the MSC are modified by introducing into the MSC the viral vector comprising the Factor VIII gene sequence operatively linked to a constitutively active promoter and a vWF gene sequence operatively linked to a constitutively active promoter, wherein the Factor VIII gene sequence and the vWF gene sequence are operatively linked to different constitutively active promoters.

19. The method of claim 10, wherein the MSC are modified by introducing into the MSC the viral vector comprising the Factor VIII gene sequence operatively linked to a constitutively active promoter and a vWF gene sequence operatively linked to a constitutively active promoter, wherein the Factor VIII gene sequence and the vWF gene sequence are operatively linked to different constitutively active promoters.

* * * * *